United States Patent
Kesteleyn et al.

(10) Patent No.: US 12,172,959 B2
(45) Date of Patent: *Dec. 24, 2024

(54) MONO- OR DI-SUBSTITUTED INDOLE DERIVATIVES AS DENGUE VIRAL REPLICATION INHIBITORS

(71) Applicants: Janssen Pharmaceuticals, Inc., Titusville, NJ (US); Katholieke Universiteit Leuven, Leuven (BE)

(72) Inventors: Bart Rudolf Romanie Kesteleyn, Beerse (BE); Jean-François Bonfanti, Issy-les-Moulineaux (FR); Tim Hugo Maria Jonckers, Beerse (BE); Pierre Jean-Marie Bernard Raboisson, Beerse (BE); Dorothée Alice Marie-Eve Bardiot, Leuven (BE); Arnaud Didier M Marchand, Leuven (BE)

(73) Assignees: Janssen Pharmaceuticals, Inc., Titusville, NJ (US); Katholieke Universiteit Leuven, Leuven (BE)

(*) Notice: Subject to any disclaimer, the term of this patent is extended or adjusted under 35 U.S.C. 154(b) by 0 days.

This patent is subject to a terminal disclaimer.

(21) Appl. No.: 18/490,072

(22) Filed: Oct. 19, 2023

(65) Prior Publication Data
US 2024/0182414 A1    Jun. 6, 2024

Related U.S. Application Data

(63) Continuation of application No. 17/139,703, filed on Dec. 31, 2020, now Pat. No. 11,827,602, which is a continuation of application No. 15/930,738, filed on May 13, 2020, now Pat. No. 10,919,854, which is a continuation of application No. 15/571,930, filed as application No. PCT/EP2016/059975 on May 4, 2016, now Pat. No. 10,696,632.

(30) Foreign Application Priority Data

May 8, 2015    (EP) .................................... 15166900
Mar. 31, 2016    (EP) .................................... 16163342

(51) Int. Cl.
| C07D 209/14 | (2006.01) |
| A61K 31/404 | (2006.01) |
| A61K 45/06 | (2006.01) |
| A61P 31/14 | (2006.01) |
| C07D 209/04 | (2006.01) |
| C07D 471/08 | (2006.01) |
| C07D 487/08 | (2006.01) |
| C07D 513/08 | (2006.01) |

(52) U.S. Cl.
CPC .......... *C07D 209/14* (2013.01); *A61K 31/404* (2013.01); *A61K 45/06* (2013.01); *A61P 31/14* (2018.01); *C07D 209/04* (2013.01); *C07D 471/08* (2013.01); *C07D 487/08* (2013.01); *C07D 513/08* (2013.01)

(58) Field of Classification Search
CPC .. C07D 209/14; C07D 209/04; C07D 471/08; C07D 487/08; C07D 513/08
See application file for complete search history.

(56) References Cited

U.S. PATENT DOCUMENTS

| | | | |
|---|---|---|---|
| 7,601,735 B2 | 10/2009 | Tyms et al. | |
| 8,143,259 B2 | 3/2012 | Colburn et al. | |
| 8,299,056 B2 | 10/2012 | Bahmanyar et al. | |
| 8,324,217 B2 | 12/2012 | Colburn et al. | |
| 8,524,764 B2 | 9/2013 | Canales et al. | |
| 8,884,030 B2 | 11/2014 | Canales et al. | |
| 8,993,604 B2 | 3/2015 | Byrd et al. | |
| 9,029,376 B2 | 5/2015 | Byrd et al. | |
| 9,522,923 B2 | 12/2016 | Richards et al. | |
| 9,944,598 B2 | 4/2018 | Kesteleyn et al. | |
| 10,029,984 B2 | 7/2018 | Kesteleyn et al. | |
| 10,064,870 B2 | 9/2018 | Rajagopalan et al. | |
| 10,071,961 B2 | 9/2018 | Vandyck et al. | |
| 10,117,850 B2 | 11/2018 | Griffioen et al. | |
| 10,206,902 B2 | 2/2019 | Kesteleyn et al. | |
| 10,323,026 B2 | 6/2019 | Ikeda et al. | |

(Continued)

FOREIGN PATENT DOCUMENTS

| CN | 102026992 A | 4/2011 |
| CN | 102186833 A | 9/2011 |

(Continued)

OTHER PUBLICATIONS

Prasad L. Polavarapu et al., "Intrinsic Rotation and Molecular Structure," Chirality 15: S143-S149 (2003).

(Continued)

*Primary Examiner* — Rebecca L Anderson
(74) *Attorney, Agent, or Firm* — Ice Miller LLP

(57) ABSTRACT

The present invention relates to mono- or di-substituted indole compounds, methods to prevent or treat dengue viral infections by using the compounds and also relates to use of the compounds as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

27 Claims, No Drawings

Specification includes a Sequence Listing.

(56) References Cited

U.S. PATENT DOCUMENTS

| | | | |
|---|---|---|---|
| 10,696,632 | B2 | 6/2020 | Kesteleyn et al. |
| 10,919,854 | B2 | 2/2021 | Kesteleyn et al. |
| 11,827,602 | B2 * | 11/2023 | Kesteleyn ............ C07D 487/08 |
| 2005/0239821 | A1 | 10/2005 | Neyts et al. |
| 2006/0194835 | A1 | 8/2006 | Dugourd et al. |
| 2006/0211698 | A1 | 9/2006 | Botyanszki et al. |
| 2008/0318338 | A1 | 12/2008 | Kamal et al. |
| 2013/0023532 | A1 | 1/2013 | Casillas et al. |
| 2014/0213586 | A1 | 7/2014 | Bardiot et al. |
| 2016/0297810 | A1 | 10/2016 | Bardiot et al. |
| 2017/0002006 | A1 | 1/2017 | Corte et al. |
| 2017/0096429 | A1 | 4/2017 | Corte et al. |
| 2017/0281633 | A1 | 10/2017 | Boylan et al. |
| 2017/0281766 | A1 | 10/2017 | Wiltzius |
| 2017/0283500 | A1 | 10/2017 | Wiltzius et al. |
| 2017/0298017 | A1 | 10/2017 | Kesteleyn et al. |
| 2018/0256544 | A1 | 9/2018 | Kesteleyn et al. |
| 2018/0256545 | A1 | 9/2018 | Kesteleyn et al. |
| 2018/0346419 | A1 | 12/2018 | Kesteleyn et al. |
| 2019/0104738 | A1 | 4/2019 | Narine et al. |
| 2019/0112266 | A1 | 4/2019 | Kesteleyn et al. |
| 2019/0183931 | A1 | 6/2019 | Bakker et al. |

FOREIGN PATENT DOCUMENTS

| | | | |
|---|---|---|---|
| CN | 104024223 | A | 9/2014 |
| JP | 2012206959 | A | 10/2012 |
| JP | 2014527978 | A | 10/2014 |
| JP | 2017531619 | A | 10/2017 |
| JP | 2017531638 | A | 10/2017 |
| JP | 2018503642 | A | 2/2018 |
| WO | 1999021559 | A1 | 5/1999 |
| WO | 02089780 | A2 | 11/2002 |
| WO | 03050295 | A2 | 6/2003 |
| WO | 2006076529 | A1 | 7/2006 |
| WO | 2009149054 | A1 | 12/2009 |
| WO | 2010021878 | A1 | 2/2010 |
| WO | 2010027500 | A1 | 3/2010 |
| WO | 2010091413 | A1 | 8/2010 |
| WO | 2011037643 | A2 | 3/2011 |
| WO | 2011088303 | A1 | 7/2011 |
| WO | 2011120025 | A1 | 9/2011 |
| WO | 2013045516 | A1 | 4/2013 |
| WO | 2014154682 | A1 | 10/2014 |
| WO | 2015187815 | | 12/2015 |
| WO | 2015188009 | | 12/2015 |
| WO | 2016050831 | A1 | 4/2016 |
| WO | 2016050841 | A1 | 4/2016 |
| WO | 2016053455 | A1 | 4/2016 |
| WO | 2016057905 | | 4/2016 |
| WO | 2016180696 | A1 | 11/2016 |
| WO | 2017013265 | | 1/2017 |
| WO | 2017046255 | A1 | 3/2017 |
| WO | 2017046258 | A1 | 3/2017 |
| WO | 2017079216 | A1 | 5/2017 |
| WO | 2017167832 | A1 | 10/2017 |
| WO | 2017167950 | A1 | 10/2017 |
| WO | 2017167951 | A1 | 10/2017 |
| WO | 2017167953 | A1 | 10/2017 |
| WO | 2017171100 | A1 | 10/2017 |
| WO | 2017173206 | A1 | 10/2017 |
| WO | 2017173256 | A1 | 10/2017 |
| WO | 2017173384 | A1 | 10/2017 |
| WO | 2017173410 | A1 | 10/2017 |
| WO | 2018167952 | A1 | 10/2017 |
| WO | 2018178238 | A1 | 10/2018 |
| WO | 2018178240 | A1 | 10/2018 |
| WO | 2018215315 | A1 | 11/2018 |
| WO | 2018215316 | A1 | 11/2018 |

OTHER PUBLICATIONS

Prevention of Dengue, Centers for Disease Control and Prevention, retrieved from the internet at https://www.cdc.gov/dengue/prevention/index.html, page last updated Sep. 27, 2012, retrieved from the internet on Jan. 8, 2019, 2 pages.

Lidia Moreira Lima et al., "Bioisosterism: A Useful Strategy for Molecular Modification and Drug Design," Current Medicinal Chemistry, Bentham Science Publishers Ltd. (2005), vol. 12, pp. 23-49.

Ian Stansfield et al., "Development of carpoxylic acid replacements in indole-N-acetamide inhibitors of hepatitis C virus NS5B polymerase," Bioorganic & Medicinal Chemistry Letters, vol. 17 (2007) 5143-5149, ScienceDirect (2007), www.sciencedirect.com, internet.

Boltromeyuk V.V., Obshchaya khimiya (General Chemistry), Minsk, Vysheyshaya shkola, 2012, p. 65 (translation).

Wolff et al., Burger's Medicinal Chemistry and Drug Discovery, 5th Ed., vol. 1: Principles and Practice, pp. 975-977 (1995).

Banker et al., (1996) Modern Pharmaceuticals, 3rd Edition, Revised and Expanded, p. 596.

N.C.B.I.: "qHTS for inhibitors of binding or entry into cells for Marburg Virus," Pubchem Bioassay Record AID 540276, Jul. 2011, 13 pages, XP55641386, Retreved from the Internet: https://pubchem.ncbi.nlm.nih.gov/bioassay/540276.

EP Search Report dated Nov. 19, 2019 from European Patent Appln No. EP 19183201.3.

"Solvation," Wikipedia, at internet address: https://en.wikipedia.org/wiki/Solvation, web page last edited on Mar. 13, 2019, 6 pages.

Examination Report dated Jan. 7, 2020, from Indian Patent Appln. No. 201727014547.

Japanese Office Action dated Jun. 2, 2020, from Japanese Patent Appln. No. JP2017-243354 (English language translation).

ACS on STN Registry No. 931079-09-3, Apr. 20, 2007.
ACS on STN Registry No. 931079-09-3, Apr. 19, 2007.
ACS on STN Registry No. 930910-25-1, Apr. 19, 2007.
ACS on STN Registry No. 930724-99-5, Apr. 18, 2007.
ACS on STN Registry No. 930463-83-5, Apr. 17, 2007.
ACS on STN Registry No. 925399-60-6, Mar. 7, 2007.
ACS on STN Registry No. 920950-24-9, Feb. 14, 2007.
ACS on STN Registry No. 920926-40-5, Feb. 14, 2007.
ACS on STN Registry No. 920888-80-8, Feb. 14, 2007.
ACS on STN Registry No. 920870-55-9, Feb. 14, 2007.
ACS on STN Registry No. 920827-69-6, Feb. 14, 2007.
ACS on STN Registry No. 920696-97-5, Feb. 13, 2007.
ACS on STN Registry No. 920694-81-1, Feb. 13, 2007.
ACS on STN Registry No. 920668-38-8, Feb. 13, 2007.
ACS on STN Registry No. 879164-92-8, Apr. 4, 2006.
ACS on STN Registry No. 878462-38-5, Mar. 29, 2006.
ACS on STN Registry No. 853320-15-7, Jun. 30, 2005.

International Search Report and Written Opinion dated Aug. 22, 2016, for International Patent Application No. PCT/EP2016/059975.

Opposition filed on Dec. 3, 2021 in Ecuadorian Patent Application No. SENADI-2019-83621 (English language translation).

Opposition filed on Dec. 3, 2021 in Ecuadorian Patent Application No. SENADI-2019-83640 (English language translation).

WHO publication, "Dengue Guidelines for Diagnosis, Treatment, Prevention and Control" 2009.

Kaptein et al., Nature, vol. 598, pp. 504-509 and method extended data and reporting summary, 2021.

https://www.cdc.gov/dengue/vaccine/parents/eligibility/need-to-know.html, accessed Oct. 14, 2022.

* cited by examiner

MONO- OR DI-SUBSTITUTED INDOLE DERIVATIVES AS DENGUE VIRAL REPLICATION INHIBITORS

RELATED APPLICATIONS

This application is a continuation of U.S. patent application Ser. No. 17/139,703, filed Dec. 31, 2020, which is a continuation of U.S. patent application Ser. No. 15/930,738, filed May 13, 2020, which is a continuation of U.S. patent application Ser. No. 15/571,930, filed Nov. 6, 2017, which is a 35 U.S.C. § 371 nationalization of PCT application PCT/EP2016/059975 filed May 4, 2016, which claims priority to European Patent Application 15166900.9 filed May 8, 2015 and European Patent Application 16163342.5 filed Mar. 31, 2016.

INCORPORATION BY REFERENCE

The contents of the text file named "56570-03031_SequenceListing_ST26.txt" which was created on Oct. 19, 2023, and is 19 KB in size, are hereby incorporated by reference in their entirety.

The present invention relates to mono- or di-substituted indole compounds, methods to prevent or treat dengue viral infections by using said compounds and also relates to said compounds for use as a medicine, more preferably for use as a medicine to treat or prevent dengue viral infections. The present invention furthermore relates to pharmaceutical compositions or combination preparations of the compounds, to the compositions or preparations for use as a medicine, more preferably for the prevention or treatment of dengue viral infections. The invention also relates to processes for preparation of the compounds.

BACKGROUND OF THE INVENTION

Flaviviruses, which are transmitted by mosquitoes or ticks, cause life-threatening infections in man, such as encephalitis and hemorrhagic fever. Four distinct, but closely related serotypes of the flavivirus dengue are known, so-called DENV-1, -2, -3, and -4. Dengue is endemic in most tropical and sub-tropical regions around the world, predominantly in urban and semi-urban areas. According to the World Health Organization (WHO), 2.5 billion people of which 1 billion children are at risk of DENV infection (WHO, 2002). An estimated 50 to 100 million cases of dengue fever [DF], half a million cases of severe dengue disease (i.e. dengue hemorrhagic fever [DHF] and dengue shock syndrome [DSS]), and more than 20,000 deaths occur worldwide each year. DHF has become a leading cause of hospitalization and death amongst children in endemic regions. Altogether, dengue represents the most common cause of arboviral disease. Because of recent large outbreaks in countries situated in Latin America, South-East Asia and the Western Pacific (including Brazil, Puerto Rico, Venezuela, Cambodia, Indonesia, Vietnam, Thailand), numbers of dengue cases have risen dramatically over the past years. Not only is the number of dengue cases increasing as the disease is spreading to new areas, but the outbreaks tend to be more severe.

To prevent and/or control the disease associated with dengue viral infection, the only available methods at present are mosquito eradication strategies to control the vector. Although progress is being made in the development of vaccines against dengue, many difficulties are encountered. These include the existence of a phenomenon referred to as antibody-dependent enhancement (ADE). Recovery from an infection by one serotype provides lifelong immunity against that serotype but confers only partial and transient protection against a subsequent infection by one of the other three serotypes. Following infection with another serotype, pre-existing heterologous antibodies form complexes with the newly infecting dengue virus serotype but do not neutralize the pathogen. Instead, virus entry into cells is believed to be facilitated, resulting in uncontrolled virus replication and higher peak viral titers. In both primary and secondary infections, higher viral titers are associated with more severe dengue disease. Since maternal antibodies can easily pass on to infants by breast feeding, this might be one of the reasons that children are more affected by severe dengue disease than adults.

In locations with two or more serotypes circulating simultaneously, also referred to as hyper endemic regions, the risk of serious dengue disease is significantly higher due to an increased risk of experiencing a secondary, more severe infection. Moreover, in a situation of hyper-endemicity, the probability of the emergence of more virulent strains is increased, which in turn augments the probability of dengue hemorrhagic fever (DHF) or dengue shock syndrome.

The mosquitoes that carry dengue, including *Aedes aegypti* and *Aedes albopictus* (tiger mosquito), are moving north on the globe. According to the United States (US) Centers for Disease Control and Prevention (CDC), both mosquitoes are currently omnipresent in southern Texas. The spread north of dengue-carrying mosquitoes is not confined to the US, but has also been observed in Europe.

Recently (December 2015), the dengue vaccine produced by Sanofi Pasteur was first approved in Mexico. The vaccine has also been approved in Brazil, The Philippines and El Salvador. Regulatory review processes are continuing in other countries where dengue is a public health priority. Nevertheless, the vaccine leaves considerable room for improvement due to limited efficacy, especially against DENV-1 and -2, low efficacy in flavivirus-naïve subjects and the lengthy dosing schedule.

Despite these shortcomings, the vaccine is a game changer in endemic settings as it will offer protection to a large part of the population, but likely not to very young infants, who bear the largest burden of dengue. In addition, the dosing schedule and very limited efficacy in flavivirus-naïve subjects make it unsuitable and likely not worthwhile/cost-effective for travelers from non-endemic areas to dengue-endemic areas. The above mentioned shortcomings of the dengue vaccines are the reason why there is a need for a pre-exposure prophylactic dengue antiviral.

Furthermore, today, specific antiviral drugs for the treatment or prevention of dengue fever virus infection are not available. Clearly, there is still a great unmet medical need for therapeutics for the prevention or treatment of viral infections in animals, more in particular in humans and especially for viral infections caused by Flaviviruses, more in particular Dengue virus. Compounds with good anti-viral potency, no or low levels of side-effects, a broad spectrum activity against multiple Dengue virus serotypes, a low toxicity and/or good pharmacokinetic or -dynamic properties are highly needed.

The present invention now provides compounds, mono- or di-substituted indole derivatives, which show high potent activity against all four (4) serotypes of the Dengue virus. Also the compounds according to the invention possess a good pharmacokinetic profile and surprisingly these specific compounds show an improved chiral stability.

SUMMARY OF THE INVENTION

The present invention is based on the unexpected finding that at least one of the above-mentioned problems can be solved by the current compounds of the invention.

The present invention provides compounds which have been shown to possess potent antiviral activity against all four (4) serotypes currently known. The present invention furthermore demonstrates that these compounds efficiently inhibit proliferation of Dengue virus (DENV). Therefore, these compounds constitute a useful class of potent compounds that can be used in the treatment and/or prevention of viral infections in animals, mammals and humans, more specifically for the treatment and/or prevention of infections with Dengue viruses.

The present invention furthermore relates to the use of such compounds as medicines and to their use for the manufacture of medicaments for treating and/or preventing viral infections, in particular with viruses belonging to the family of the Dengue viruses in animals or mammals, more in particular in humans. The invention also relates to methods for the preparation of all such compounds and to pharmaceutical compositions comprising them in an effective amount.

The present invention also relates to a method of treatment or prevention of dengue viral infections in humans by the administration of an effective amount of one or more such compounds, or a pharmaceutically acceptable salt thereof optionally in combination with one or more other medicines, like another antiviral agent or dengue vaccine or both, to a patient in need thereof.

One aspect of the invention is the provision of compounds of formula (I)

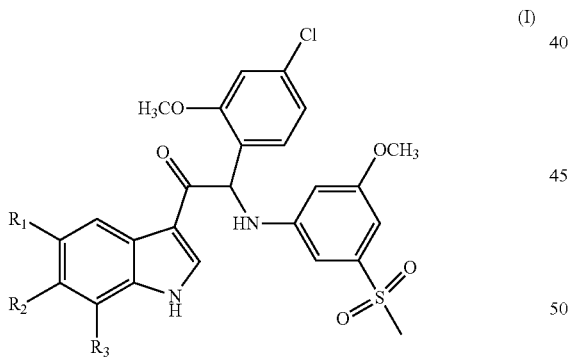

(I)

a stereo-isomeric form, a pharmaceutically acceptable salt, solvate or polymorph thereof comprising a mono- or di-substituted indole group; said compound is selected from the group wherein:

$R_1$ is H, $R_2$ is F and $R_3$ is H or $CH_3$,
$R_1$ is H, $CH_3$ or F, $R_2$ is $OCH_3$ and $R_3$ is H,
$R_1$ is H, $R_2$ is $OCH_3$ and $R_3$ is $CH_3$,
$R_1$ is $CH_3$, $R_2$ is F and $R_3$ is H,
$R_1$ is $CF_3$ or $OCF_3$, $R_2$ is H and $R_3$ is H,
$R_1$ is $OCF_3$, $R_2$ is $OCH_3$ and $R_3$ is H and
$R_1$ is $OCF_3$, $R_2$ is H and $R_3$ is $CH_3$.

In particular the compounds of the invention or their stereo-isomeric form, a is pharmaceutically acceptable salt, solvate or polymorph thereof are selected from the group:

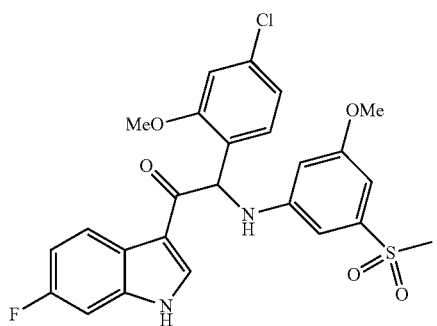

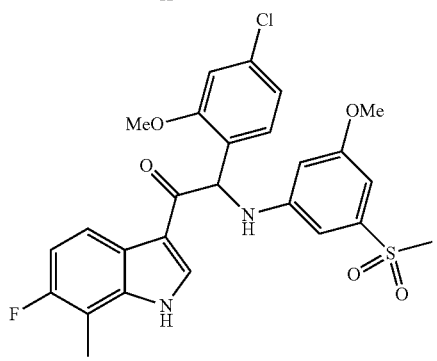

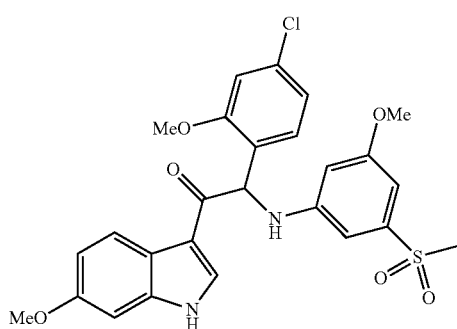

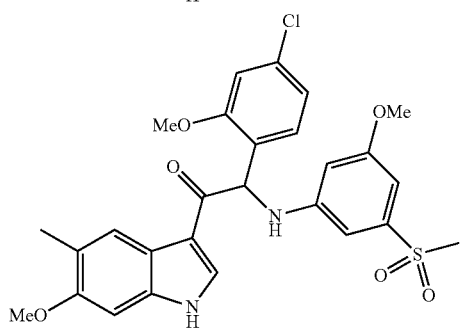

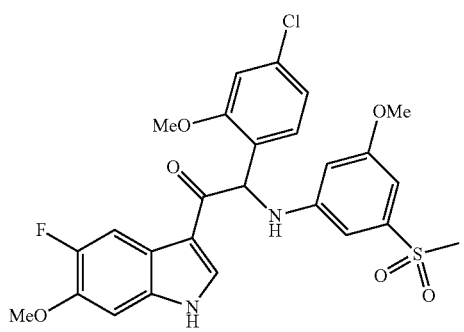

-continued

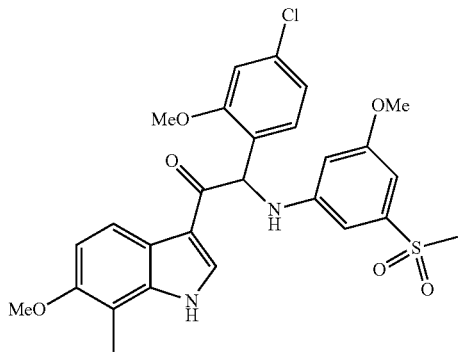

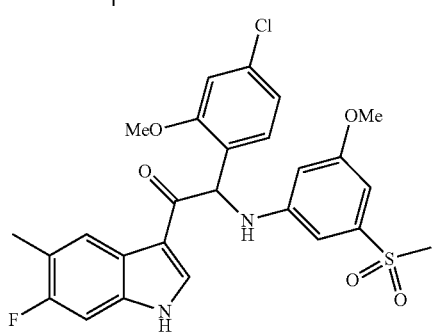

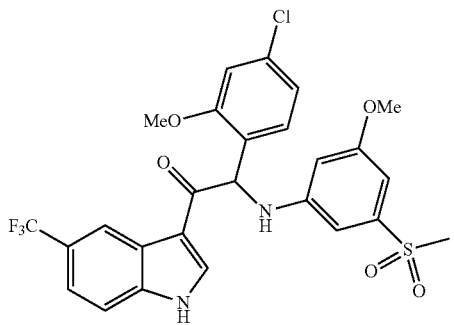

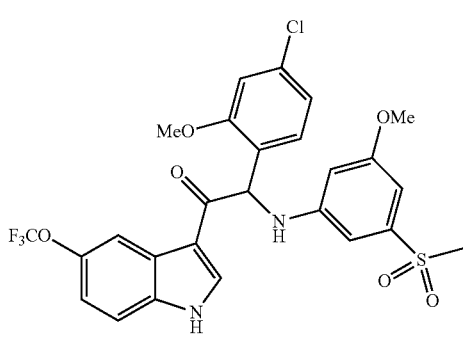

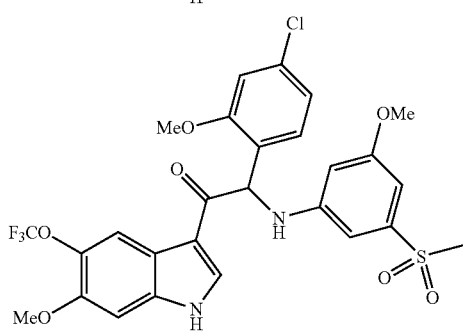

-continued

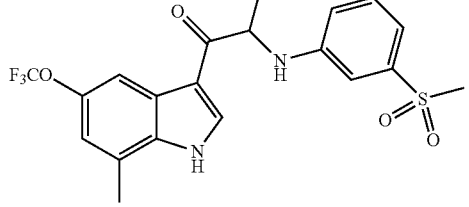

Another aspect of the invention is the use of a compound represented by the following structural formula (I)

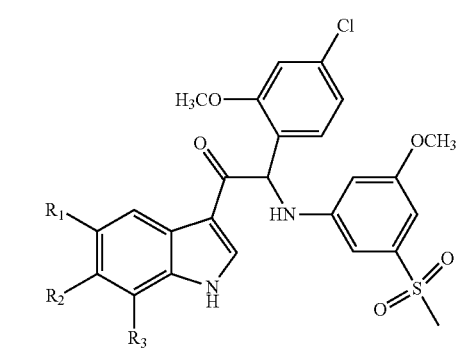

(I)

a stereo-isomeric form, a pharmaceutically acceptable salt, solvate or polymorph thereof comprising a mono- or di-substituted indole group; said compound is selected from the group wherein:

$R_1$ is H, $R_2$ is F and $R_3$ is H or $CH_3$,
$R_1$ is H, $CH_3$ or F, $R_2$ is $OCH_3$ and $R_3$ is H and
$R_1$ is H, $R_2$ is $OCH_3$ and $R_3$ is $CH_3$,
$R_1$ is $CH_3$, $R_2$ is F and $R_3$ is H,
$R_1$ is $CF_3$ or $OCF_3$, $R_2$ is H and $R_3$ is H,
$R_1$ is $OCF_3$, $R_2$ is $OCH_3$ and $R_3$ is H and
$R_1$ is $OCF_3$, $R_2$ is H and $R_3$ is $CH_3$ for inhibiting the replication of dengue virus(es) in a biological sample or patient.

Part of the current invention is also a pharmaceutical composition comprising a compound of formula (I) or a stereo-isomeric form, a pharmaceutically acceptable salt, solvate or polymorph thereof together with one or more pharmaceutically acceptable excipients, diluents or carriers.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in un-solvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral or rectal administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

The present disclosure is also intended to include any isotopes of atoms present in the compounds of the invention. For example, isotopes of hydrogen include tritium and deuterium and isotopes of carbon include C-13 and C-14. The present compounds used in the current invention may also exist in their stereo-chemically isomeric form, defining all possible compounds made up of the same atoms bonded by the same sequence of bonds but having different three-dimensional structures, which are not interchangeable. Unless otherwise mentioned or indicated, the chemical designation of compounds encompasses the mixture of all possible stereo-chemically isomeric forms, which said compounds might possess.

Said mixture may contain all dia-stereomers and/or enantiomers of the basic molecular structure of said compound. All stereo-chemically isomeric forms of the compounds used in the present invention either in pure form or in admixture with each other are intended to be embraced within the scope of the present invention including any racemic mixtures or racemates.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of compounds and intermediates used in this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

General Synthetic Approaches

The synthesis of compounds of general formula I can be performed as outlined in Scheme 1. 2-(4-Chloro-2-methoxyphenyl)acetic acid (II) can be converted to the corresponding 2-(4-chloro-2-methoxyphenyl)acetyl chloride (III) with a chlorination reagent like for example thionyl chloride. The Friedel-Crafts reaction of the acid chloride III with a substituted indole of general formula IV can be performed using a Lewis acid reagent like for example $Et_2AlCl$ or $TiCl_4$ in a suitable solvent like for example $CH_2Cl_2$ or 1,2-dichloroethane, and under suitable reaction conditions that typically (but not exclusively) involve cooling, to provide the 3-acylated indole of general formula V. The introduction of an aniline moiety in alpha position to the carbonyl moiety of the compounds of general formula V can be accomplished by a reaction sequence that involves for example bromination of V with a reagent like for example phenyltrimethylammonium tribromide in a suitable solvent like for example THF, to provide the compounds of general formula VI, and subsequent reaction of the compounds of general formula VI with 3-methoxy-5-(methyl-sulfonyl)aniline (VII) in a suitable solvent like for example $CH_3CN$, and typically using a base like for example TEA or DIPEA, to provide the compounds of general formula I as racemic mixtures. Chiral separation of the compounds of general formula I can be performed by for example chiral chromatography to provide the Enantiomers A and B of general formula I.

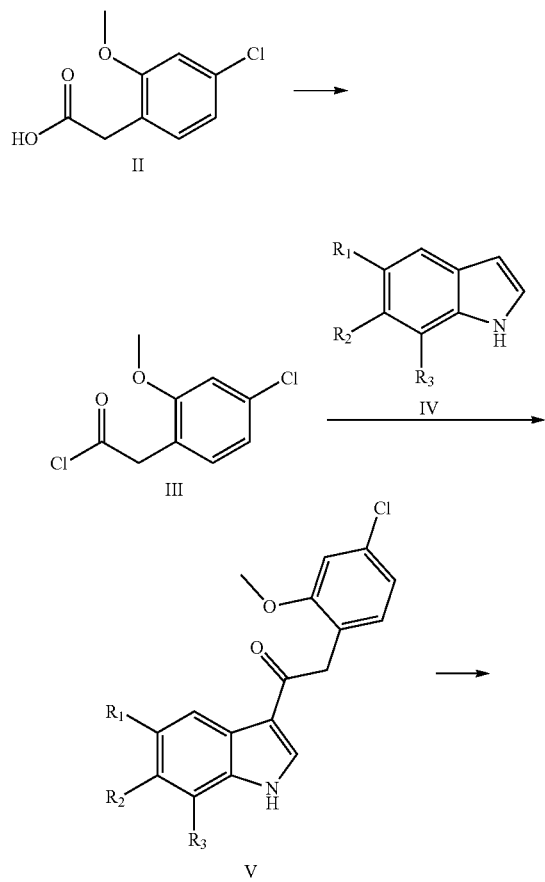

Scheme 1

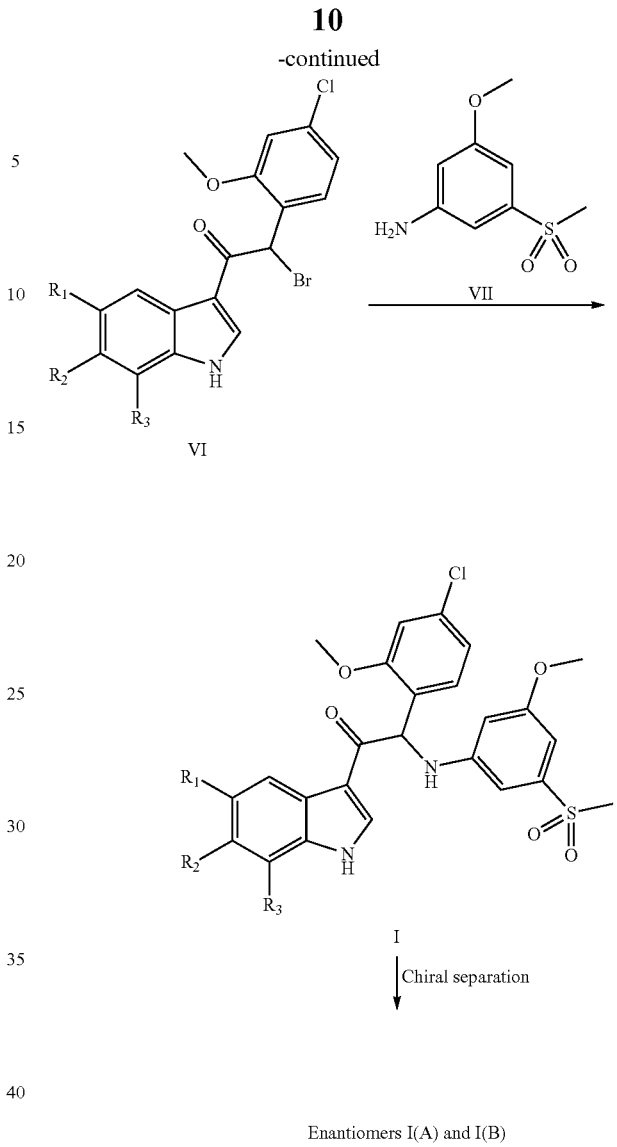

Enantiomers I(A) and I(B)

In some cases, the synthesis of the intermediate of general formula V via the Friedel-Crafts synthesis approach, benefits from the presence of a protecting group (PG) at the indole-N during the Friedel-Crafts reaction step, as outlined in Scheme 2. To this end, the substituted indole of general formula IV can be converted first to an N-protected intermediate of general formula VIII, such as for example an N-Tosylated intermediate of general formula VIII (PG=Ts), using a reagent like for example tosyl chloride, in the presence of a base like for example sodium hydride. The Friedel-Crafts reaction of the substituted indole of general formula IV with acid chloride III can be performed using a Lewis acid reagent like for example $Et_2AlCl$ or $TiCl_4$ in a suitable solvent like for example $CH_2Cl_2$ or 1,2-dichloroethane, and under suitable reaction conditions that typically (but not exclusively) involve cooling, to provide the 3-acylated N-protected indole of general formula IX. Removal of the indole-N protecting group PG of the intermediate of general formula IX can be accomplished with a reagent like for example LiOH (for PG=Ts) in a solvent mixture like for example THF/water an at a suitable reaction temperature, to provide the 3-acylated indole of general formula V.

Scheme 2

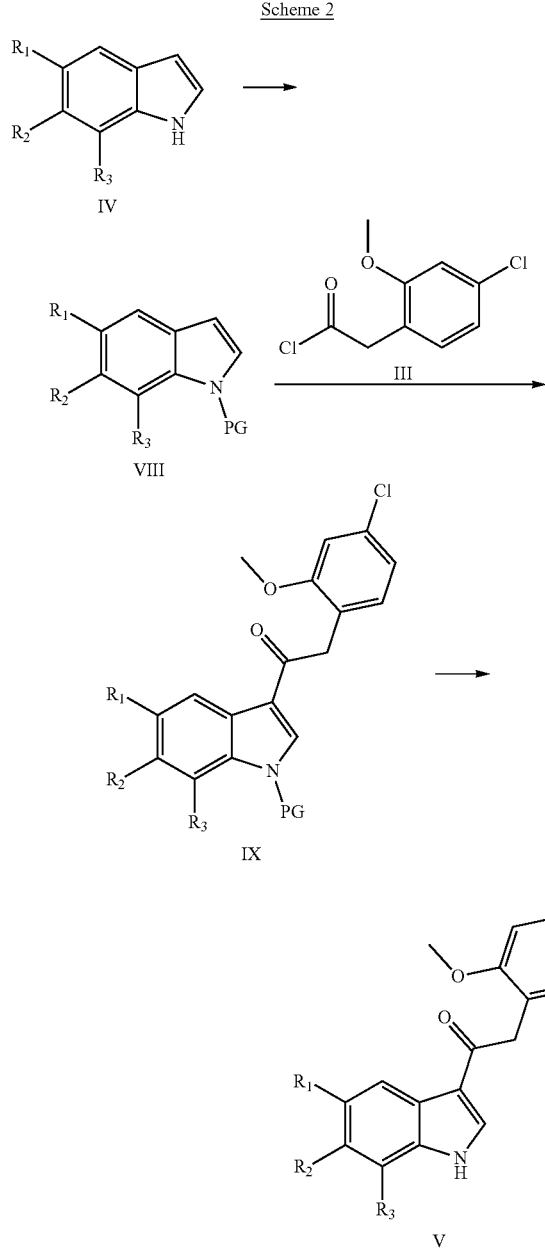

example by treatment with an aqueous hydrochloric acid solution at elevated temperature, provides the intermediate of general formula V.

Scheme 3

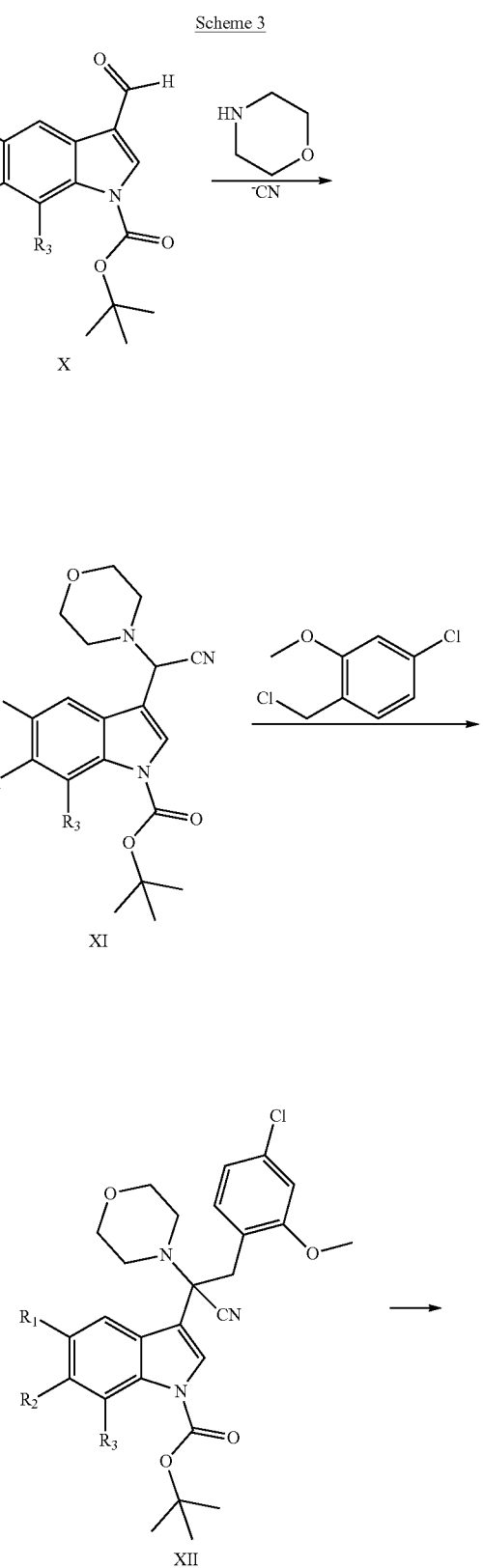

As an alternative approach, the intermediate of general formula V can also be prepared as outlined in Scheme 3: The N-Boc-protected substituted indole-3-carbaldehyde of general formula X can be converted to the corresponding Strecker-type of intermediate of general formula XI by reaction with morpholine in the presence of reagents like for example sodium cyanide and sodium bisulfite and in a suitable solvent like for example a mixture of water and a water-mixable organic solvent like for example dioxane. Alkylation of the compound of general formula XI with 4-chloro-2-methoxy-benzylchloride can be accomplished in the presence of a base like for example potassium hexamethyldisilazane and in a suitable solvent like for example DMF to provide the compound of general formula XII. Submission of the compound of general formula XII to a suitable aqueous acidic hydrolytic condition like for

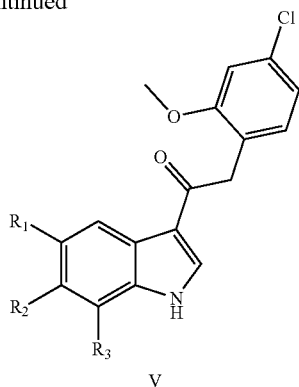

V

EXAMPLES

LC/MS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). In case the compound was not directly ionizable the type of adduct is specified (i.e. $[M+NH_4]^+$, $[M+HCOO]^-$, etc . . . ). For molecules with multiple isotopic patterns (Br, Cl), the reported value is the one obtained for the lowest isotope mass. All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica.

LCMS Method codes (Flow expressed in mL/min; column temperature (T) in ° C.; Run time in minutes)

| Method code | Instrument | Column | Mobile phase | Gradient | Flow/ Col T | Run time (min) |
|---|---|---|---|---|---|---|
| LC-A | Waters: Acquity ® UPLC ® - DAD-SQD | Waters: BEH C18 (1.7 µm, 2.1 × 50 mm) | A: 10 mM $CH_3COONH_4$ in 95% $H_2O$ 5% $CH_3CN$ B: $CH_3CN$ | From 95% A to 5% A in 1.3 min, held for 0.7 min | 0.8 mL/min/ 55° C. | 2 |
| LC-B | Waters: Acquity ® UPLC ® - DAD-SQD | Waters: HSS T3 (1.8 µm, 2.1 × 100 mm) | A: 10 mM $CH_3COONH_4$ in 95% $H_2O$ + 5% $CH_3CN$ B: $CH_3CN$ | From 100% A to 5% A in 2.10 min, to 0% A in 0.90 min, to 5% A in 0.5 min | 0.7 mL/min/ 55° C. | 3.5 |
| LC-C | Waters: Acquity ® UPLC ® - DAD-Quattro Micro ™ | Waters: BEH C18 (1.7 µm, 2.1 × 100 mm) | A: 95% $CH_3COONH_4$ 7 mM/5% $CH_3CN$, B: $CH_3CN$ | 84.2% A for 0.49 min, to 10.5% A in 2.18 min, held for 1.94 min, back to 84.2% A in 0.73 min, held for 0.73 min | 0.343 mL/min/ 40° C. | 6.2 |
| LC-D | Waters: Acquity ® UPLC ® - DAD-Acquity ® TQ detector | Waters: BEH C18 (1.7 µm, 2.1 × 50 mm) | A: 10 mM $CH_3COONH_4$ (adjusted at pH 10) B: $CH_3CN$ | From 50% A to 10% A in 3.5 min, held for 1.5 min | 0.5 mL/min/ 40° C. | 5 |

SFC-MS Methods

The SFC measurement was performed using an Analytical Supercritical fluid chromatography (SFC) system composed by a binary pump for delivering carbon dioxide (CO2) and modifier, an autosampler, a column oven, a diode array detector equipped with a high-pressure flow cell standing up to 400 bars. If configured with a Mass Spectrometer (MS) the flow from the column was brought to the (MS). It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Analytical SFC-MS Methods (Flow expressed in mL/min; column temperature (T) in ° C.; Run time in minutes, Backpressure (BPR) in bars.

| Method code | column | mobile phase | gradient | Flow/ Col T | Run time/ BPR |
|---|---|---|---|---|---|
| SFC-A | WHELK-O1 (S,S) 5 μm 250 × 4.6 mm Regis | A: CO$_2$ B: MeOH | 50% B hold 7 min, | 3/ 35 | 7/ 100 |
| SFC-B | Daicel Chiralpak ® IC-H column (5 μm, 150 × 4.6 mm) | A: CO$_2$ B: MeOH | 40% B hold 7 min, | 3/ 35 | 7/ 100 |
| SFC-C | WHELK-O1 (S,S) 5 μm 250 × 4.6 mm Regis | A: CO$_2$ B: MeOH | 60% B hold 9 min, | 3/ 35 | 9/ 100 |
| SFC-D | Daicel Chiralpak ® IA-H column (5 μm, 250 × 4.6 mm) | A: CO$_2$ B: MeOH | 50% B hold 7 min, | 3/ 35 | 7/ 100 |
| SFC-E | Daicel Chiralpak ® AS3 column (3.0 μm, 150 × 4.6 mm) | A: CO$_2$ B: EtOH + 0.2% iPrNH$_2$ + 3% H$_2$O | 10%-50% B in 6 min, hold 3.5 min | 2.5/ 40 | 9.5/ 110 |
| SFC-F | Daicel Chiralpak ® AD-H column (5.0 μm, 150 × 4.6 mm) | A: CO$_2$ B: iPrOH + 0.3% iPrNH$_2$ | 30% B hold 7 min | 3/ 35 | 7/ 100 |

Melting Points

Values are either peak values or melt ranges, and are obtained with experimental uncertainties that are commonly associated with this analytical method.

DSC823e (Indicated as DSC)

For a number of compounds, melting points were determined with a DSC823e (Mettler-Toledo). Melting points were measured with a temperature gradient of 10° C./minute. Maximum temperature was 300° C.

Optical Rotations

Optical rotations were measured on a Perkin-Elmer 341 polarimeter with a sodium lamp and reported as follows: [α]° (λ, c g/100 ml, solvent, T° C.).

$[\alpha]_\lambda^T = (100\alpha)/(l \times c)$: where l is the path length in dm and c is the concentration in g/100 ml for a sample at a temperature T (° C.) and a wavelength λ (in nm). If the wavelength of light used is 589 nm (the sodium D line), then the symbol D might be used instead. The sign of the rotation (+ or −) should always be given. When using this equation the concentration and solvent are always provided in parentheses after the rotation. The rotation is reported using degrees and no units of concentration are given (it is assumed to be g/100 ml).

Example 1: Synthesis of 2-(4-chloro-2-methoxyphenyl)-1-(6-fluoro-1H-indol-3-yl)-2-((3-methoxy-5-(methylsulfonyl)phenyl)amino)ethanone (Compound 1) and Chiral Separation Into Enantiomers 1A and 1B

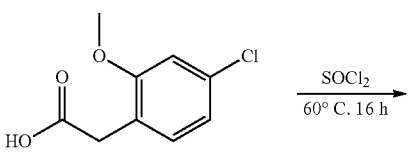

-continued

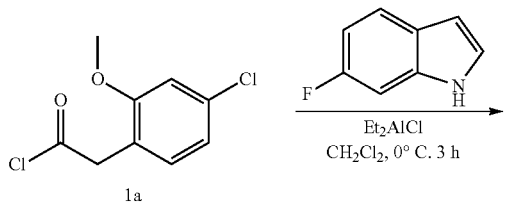

1a

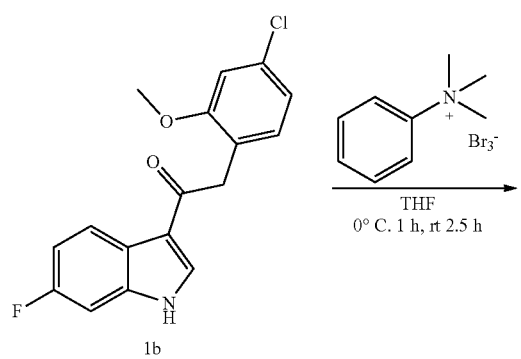

1b

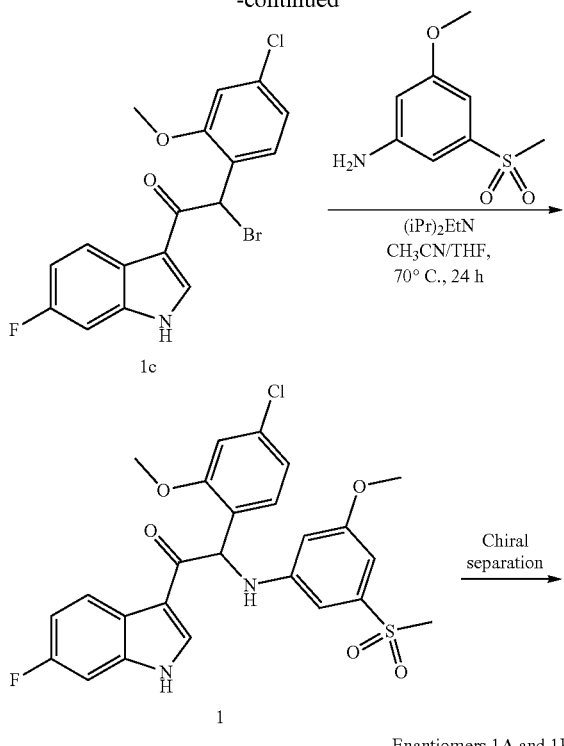

Synthesis of Intermediate 1a 2-(4-Chloro-2-methoxyphenyl)acetic acid [CAS 170737-95-8] (5.8 g, 28.9 mmol) was added in small portions to thionyl chloride (50 mL) and the resulting solution was stirred overnight at 60° C. The solvent was concentrated under reduced pressure and co-evaporated with toluene to give 2-(4-chloro-2-methoxyphenyl)-acetyl chloride 1a (6.5 g) as an oily residue that was used without further purification in the next step.

Synthesis of Intermediate 1b

Diethylaluminum chloride 1M in hexane (37.1 mL, 37.1 mmol) was added dropwise at 0° C. to a solution of 6-fluoro-1H-indole [CAS 399-51-9] (3.34 g, 24.76 mmol) in $CH_2Cl_2$ (100 mL). After 30 min at 0° C., a solution of 2-(4-chloro-2-methoxyphenyl)acetyl chloride 1a (6.3 g, 28.76 mmol) in $CH_2Cl_2$ (100 mL) was added slowly at 0° C. The reaction was stirred at 0° C. for 3 h. Ice-water was added and the precipitate was filtered off, washed with water and a small amount of $CH_2Cl_2$. The solids were dried under vacuum at 70° C. overnight to give 2-(4-chloro-2-methoxyphenyl)-1-(6-fluoro-1H-indol-3-yl)ethanone 1b (4.9 g).

Synthesis of Intermediate 1c

At 0° C., a solution of phenyltrimethylammonium tribromide [CAS 4207-56-1] (5.8 g, 15.4 mmol) in THF (65 mL) was added dropwise to a mixture of 2-(4-chloro-2-methoxyphenyl)-1-(6-fluoro-1H-indol-3-yl)ethanone 1b (4.9 g, 15.4 mmol) in THF (60 mL). The mixture was stirred at 0° C. for 1 h and at room temperature for 2.5 h. The precipitate was filtered off and washed with EtOAc. The combined filtrates were concentrated under reduced pressure. The residue was taken up with EtOAc and washed with water. A precipitate appeared in the organic layer and was filtered off and dried to provide a first batch of 2-bromo-2-(4-chloro-2-methoxyphenyl)-1-(6-fluoro-1H-indol-3-yl)ethanone 1c (4.6 g). The organic layer was separated, dried over $MgSO_4$, filtered and the solvent was evaporated under reduced pressure. The residue was crystallized from EtOAc, the precipitate was filtered off, washed with $Et_2O$ and dried under vacuum to provide a second fraction of 2-bromo-2-(4-chloro-2-methoxyphenyl)-1-(6-fluoro-1H-indol-3-yl)ethanone 1c (1.6 g).

Synthesis of Compound 1 and Chiral Separation of Enantiomers 1A and 1B

A mixture of 2-bromo-2-(4-chloro-2-methoxyphenyl)-1-(6-fluoro-1H-indol-3-yl)-ethanone 1c (3 g, 7.56 mmol), 3-methoxy-5-(methylsulfonyl)aniline [CAS 62606-02-4] (2.28 g, 11.35 mmol) and diisopropylethylamine (1.95 mL, 11.35 mmol) in $CH_3CN$ (60 mL) and THF (30 mL) was stirred at 70° C. for 24 h. The reaction was diluted with EtOAc. The organic layer was washed with 1N HCl (twice) and water, dried over $MgSO_4$, filtered and the solvent was concentrated under reduced pressure. The residue was purified by flash chromatography on silica gel (15-40 μm, 80 g, Mobile phase: $CH_2Cl_2$/MeOH 99.5/0.5). A second purification was carried out by flash chromatography on silica gel (15-40 μm, 80 g, Mobile phase: $CH_2Cl_2$/MeOH 99.7/0.3). The pure fractions were combined and concentrated under reduced pressure to give 2-(4-chloro-2-methoxyphenyl)-1-(6-fluoro-1H-indol-3-yl)-2-((3-methoxy-5-(methylsulfonyl)phenyl)amino)ethanone (Compound 1, 2 g) as a racemic mixture.

The enantiomers of Compound 1 were separated via Chiral SFC (Stationary phase: Chiralpak® AD-H 5 μm 20×250 mm, Mobile phase: 50% $CO_2$, 50% MeOH) yielding 740 mg of the first eluted enantiomer and 720 mg of the second eluted enantiomer. The first eluted enantiomer was crystallized from $CH_3CN/Et_2O$. The precipitate was filtered off and dried to give Enantiomer 1A (645 mg). The second eluted enantiomer was crystallized from $CH_3CN/Et_2O$. The precipitate was filtered off and dried to give Enantiomer 1B (632 mg).

Compound 1

$^1$H NMR (500 MHz, DMSO-$d_6$) δ ppm 3.09 (s, 3 H) 3.72 (s, 3 H) 4.00 (s, 3 H) 6.24 (d, J=7.9 Hz, 1 H) 6.58 (s, 2 H) 6.91 (s, 1 H) 6.97 (dd, J=8.7, 1.9 Hz, 1 H) 7.02-7.09 (m, 2 H) 7.12 (d, J=1.9 Hz, 1 H) 7.27 (dd, J=9.5, 1.9 Hz, 1 H) 7.35 (d, J=8.5 Hz, 1 H) 8.14 (dd, J=8.7, 5.5 Hz, 1 H) 8.44 (s, 1 H) 12.10 (br. s., 1 H)
LC/MS (method LC-C): $R_t$ 3.08 min, MH$^+$ 517
Melting point: 174° C.

Enantiomer 1A $^1$H NMR (500 MHz, DMSO-$d_6$) δ ppm 3.09 (s, 3 H) 3.72 (s, 3 H) 4.00 (s, 3 H) 6.24 (d, J=7.9 Hz, 1 H) 6.59 (s, 2 H) 6.91 (s, 1 H) 6.97 (dd, J=8.8, 2.2 Hz, 1 H) 7.02-7.10 (m, 2 H) 7.12 (d, J=2.2 Hz, 1 H) 7.27 (dd, J=9.6, 2.2 Hz, 1 H) 7.35 (d, J=8.2 Hz, 1 H) 8.14 (dd, J=8.8, 5.7 Hz, 1 H) 8.44 (s, 1 H) 12.10 (br. s., 1 H)
LC/MS (method LC-C): $R_t$ 3.09 min, MH$^+$ 517
$[\alpha]_D^{20}$: +130.3° (c 0.277, DMF)
Chiral SFC (method SFC-D): $R_t$ 3.41 min, MH$^+$ 517, chiral purity 100%.
Melting point: 220° C.

Enantiomer 1B $^1$H NMR (400 MHz, DMSO-d$_6$) δ ppm 3.09 (s, 3 H) 3.72 (s, 3 H) 4.00 (s, 3 H) 6.24 (d, J=7.6 Hz, 1 H) 6.53-6.65 (m, 2 H) 6.91 (s, 1 H) 6.97 (dd, J=8.6, 2.0 Hz, 1 H) 7.01-7.09 (m, 2 H) 7.12 (d, J=2.0 Hz, 1 H) 7.27 (dd, J=9.6, 2.0 Hz, 1 H) 7.35 (d, J=8.1 Hz, 1 H) 8.14 (dd, J=8.6, 5.6 Hz, 1 H) 8.43 (s, 1 H) 12.09 (br. s., 1 H)

LC/MS (method LC-C): R$_t$ 3.09 min, MH$^+$ 517

[α]$_D^{20}$: −135.3° (c 0.283, DMF)

Chiral SFC (method SFC-D): R$_t$ 4.89 min, MH$^+$ 517, chiral purity 99.35%.

Melting point: 218° C.

Example 1.1: Chiral Stability of Enantiomer 1A at pH 7.4

The chiral stability of Enantiomer 1A (R=OMe) was evaluated by determination of the enantiomeric excess (ee %) after incubation for 24 h and 48 h in a buffered solution at pH 7.4 at 40° C. and 60° C. To assess the influence of the methoxy-substituent of Enantiomer 1A (R=OMe) on the stability against racemization, the chiral stability of Enantiomer 1'A (R=H) was tested under the same conditions. To this end, 5 μM buffered (pH=7.4) solutions of 1A and 1'A were prepared by mixing 25 μL of a 100 μM solution of 1A or 1'A in DMSO with 475 μL aqueous buffer pH 7.4. Samples were taken 24 h and 48 h after incubation at 40° C. and 60° C. The analytical samples were analyzed by Chiral SFC (MS detection) and the chiral purity was expressed as the enantiomeric excess (ee %=% enantiomer A−% enantiomer B). Both Enantiomers 1A and 1'A had a chiral purity of 100% prior to their incubation.

1A (R = OMe)
1'A (R = H)

|  |  | ee % Sampling timepoints (h) | |
| --- | --- | --- | --- |
| Compound | Temperature | 24 | 48 |
| 1A | 40° C. | 100 | 100 |
|  | 60° C. | 95 | 88 |
| 1'A | 40° C. | 21 | 10 |
|  | 60° C. | 0 | 0 |

Example 2: Synthesis of 2-(4-chloro-2-methoxyphenyl)-1-(6-fluoro-7-methyl-1H-indol-3-yl)-2-((3-methoxy-5-(methylsulfonyl)phenyl)amino)ethanone (Compound 2) and Chiral Separation Into Enantiomers 2A and 2B

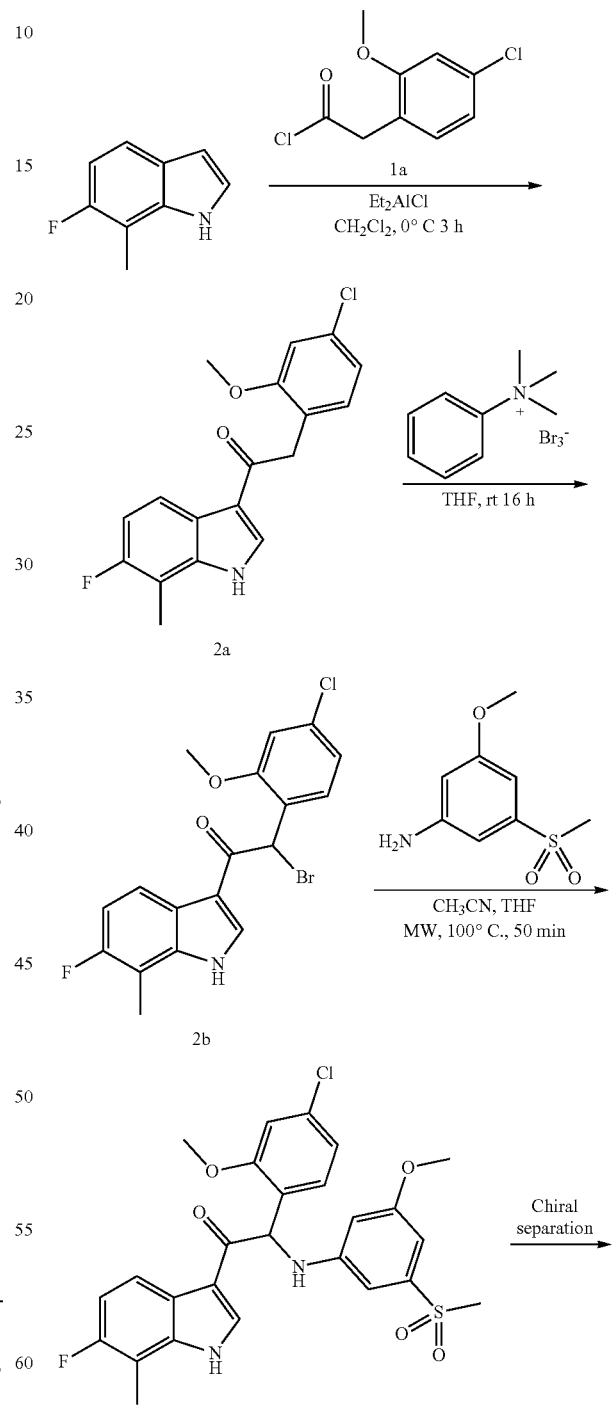

Enantiomers 2A and 2B

Synthesis of Intermediate 2a

Diethylaluminum chloride 1M in hexane (20 mL, 20.0 mmol) was added dropwise at 0° C. to a solution of 6-fluoro-7-methyl-1H-indole [CAS 57817-10-4] (1.50 g, 10.1 mmol) in CH$_2$Cl$_2$ (45 mL). After 30 min at 0° C., a solution of 2-(4-chloro-2-methoxyphenyl)acetyl chloride (3.30 g, 15.1 mmol, synthesis: see Example 1) in dichloromethane (30 mL) was added slowly. The reaction mixture was stirred at 0° C. for 3 h. 1M Rochelle salt solution (50 mL) was added and the reaction mixture was stirred at room temperature for 1 h. The solids were filtered off and partitioned between EtOAc and 1N HCl. The phases were separated. The aqueous phase was extracted with EtOAc. The organic phases were combined, washed with brine, dried over MgSO$_4$, filtered and concentrated under reduced pressure. The residue was triturated with EtOAc and heptane. The precipitate was filtered off to give 2-(4-chloro-2-methoxyphenyl)-1-(6-fluoro-7-methyl-1H-indol-3-yl)ethanone 2a (2.00 g).

Synthesis of Intermediate 2b

A solution of phenyltrimethylammonium tribromide [CAS 4207-56-1] (2.49 g, 6.6 mmol) in THF (45 mL) was added dropwise at 0° C. to a solution of 2-(4-chloro-2-methoxyphenyl)-1-(6-fluoro-7-methyl-1H-indol-3-yl)ethanone 2a (2.00 g, 6.0 mmol) in THF (65 mL). The mixture was stirred at room temperature overnight. The precipitate was filtered off and washed with EtOAc. The combined filtrates were concentrated under reduced pressure. The residue was taken up with a minimum of acetonitrile. The precipitate was filtered off, washed with acetonitrile and dried under vacuum to give a first batch of 2-bromo-2-(4-chloro-2-methoxy-phenyl)-1-(6-fluoro-7-methyl-1H-indol-3-yl)ethanone 2b (1.51 g). The filtrate was concentrated under reduced pressure. The residue was taken up with a minimum of acetonitrile. The precipitate was filtered off, washed with acetonitrile and dried under vacuum to give a second fraction of 2-bromo-2-(4-chloro-2-methoxyphenyl)-1-(6-fluoro-7-methyl-1H-indol-3-yl)ethanone 2b (0.70 g).

Synthesis of Compound 2 and Chiral Separation of Enantiomers 2A and 2B

A mixture of 2-bromo-2-(4-chloro-2-methoxyphenyl)-1-(6-fluoro-7-methyl-1H-indol-3-yl)ethanone 2b (1.8 g, 4.36 mmol) and 3-methoxy-5-(methylsulfonyl)aniline [CAS 62606-02-4] (2.6 g, 13.0 mmol) in THF (9 mL) and CH$_3$CN (9 mL) was heated at 100° C. under microwave irradiation for 50 min. The reaction mixture was diluted with EtOAc and washed with 1N HCl. The phases were separated. The organic phase was washed with an aqueous saturated NaHCO$_3$ solution and brine, dried over MgSO$_4$, filtered and concentrated under reduced pressure. The residue was taken up with a minimum of acetonitrile. The precipitate was filtered off, washed with acetonitrile and dried under vacuum to give 2-(4-chloro-2-methoxy-phenyl)-1-(6-fluoro-7-methyl-1H-indol-3-yl)-2-((3-methoxy-5-(methylsulfonyl)-phenyl)amino)ethanone (Compound 2, 1.7 g) as a racemic mixture. The chiral separation of the enantiomers of Compound 2 (1.59 g) was performed via Preparative SFC (Stationary phase: (S,S)-Whelk-O1 5 μm 250×21.1 mm, Mobile phase: 50% CO$_2$, 50% MeOH). The product fractions were combined and evaporated under reduced pressure. The first eluted enantiomer (746 mg) was further purified by column chromatography on silica gel (15-40 μm, 24 g, Mobile phase: CH$_2$Cl$_2$/MeOH 99.5/0.5). The pure fractions were combined and evaporated under reduced pressure (560 mg). The residue was solidified by trituration with a mixture of Et$_2$O and a few drops of CH$_3$CN. The solids were filtered off and dried under vacuum to give Enantiomer 2A (473 mg). The second eluted enantiomer (732 mg) was further purified by column chromatography over silica gel (15-40 μm, 24 g, Mobile phase: CH$_2$Cl$_2$/MeOH 99.5/0.5). The pure fractions were combined and evaporated under reduced pressure (550 mg). The residue was solidified by trituration with a mixture of Et$_2$O and a few drops of CH$_3$CN. The solids were filtered off and dried under vacuum to give of Enantiomer 2B (457 mg).

Compound 2

$^1$H NMR (300 MHz, DMSO-d$_6$) δ ppm 2.38 (d, J=1.5 Hz, 3 H) 3.10 (s, 3 H) 3.73 (s, 3 H) 4.01 (s, 3 H) 6.27 (d, J=7.9 Hz, 1 H) 6.55-6.63 (m, 2 H) 6.93 (m, 1 H) 6.94-7.09 (m, 3 H) 7.13 (d, J=1.9 Hz, 1 H) 7.35 (d, J=8.3 Hz, 1 H) 7.97 (dd, J=8.7, 5.3 Hz, 1 H) 8.45 (s, 1 H) 12.23 (br. s, 1 H)

LC/MS (method LC-D): R$_t$ 1.68 min, MH$^+$ 531

Enantiomer 2A $^1$H NMR (500 MHz, DMSO-d$_6$) δ ppm 2.37-2.39 (m, 3 H) 3.09 (s, 3 H) 3.72 (s, 3 H) 4.01 (s, 3 H) 6.26 (d, J=7.9 Hz, 1 H) 6.54-6.63 (m, 2 H) 6.92 (s, 1 H) 6.97 (dd, J=8.4, 1.9 Hz, 1 H) 7.02 (dd, J=9.9, 9.0 Hz, 1 H) 7.07 (d, J=7.9 Hz, 1 H) 7.13 (d, J=1.9 Hz, 1 H) 7.35 (d, J=8.4 Hz, 1 H) 7.96 (dd, J=8.5, 5.4 Hz, 1 H) 8.45 (s, 1 H) 12.24 (br. s., 1 H)

LC/MS (method LC-C): R$_t$ 3.20 min, MH$^+$ 531

[α]$_D^{20}$: +104.5° (c 0.2545, DMF)

Chiral SFC (method SFC-A): R$_t$ 4.22 min, MH$^+$ 531, chiral purity 100%.

Enantiomer 2B $^1$H NMR (500 MHz, DMSO-d$_6$) δ ppm 2.36-2.41 (m, 3 H) 3.09 (s, 3 H) 3.72 (s, 3 H) 4.01 (s, 3 H) 6.26 (d, J=7.9 Hz, 1 H) 6.57-6.64 (m, 2 H) 6.92 (s, 1 H) 6.97 (dd, J=8.2, 1.9 Hz, 1 H) 6.99-7.04 (m, 1 H) 7.07 (d, J=7.9 Hz, 1 H) 7.13 (d, J=1.9 Hz, 1 H) 7.35 (d, J=8.2 Hz, 1 H) 7.96 (dd, J=8.7, 5.2 Hz, 1 H) 8.45 (s, 1 H) 12.24 (br. s., 1 H)

LC/MS (method LC-C): R$_t$ 3.20 min, MH$^+$ 531

[α]$_D^{20}$: −104.1° (c 0.2536, DMF)

Chiral SFC (method SFC-A): R$_t$ 5.12 min, MH$^+$ 531, chiral purity 99.53%.

Example 3: Synthesis 2-(4-chloro-2-methoxyphenyl)-1-(6-methoxy-1H-indol-3-yl)-2-((3-methoxy-5-(methylsulfonyl)phenyl)amino)ethanone (Compound 3) and Chiral Separation Into Enantiomers 3A and 3B

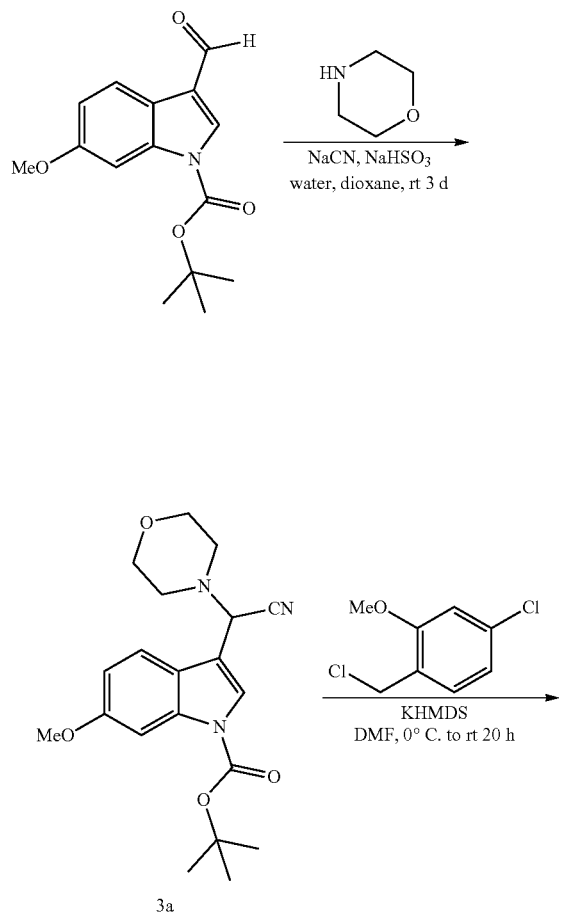

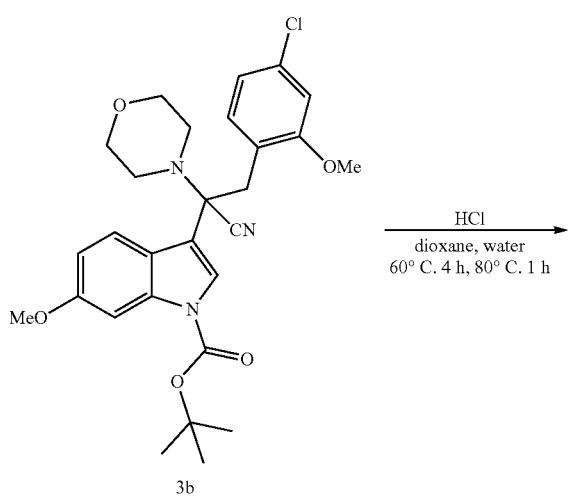

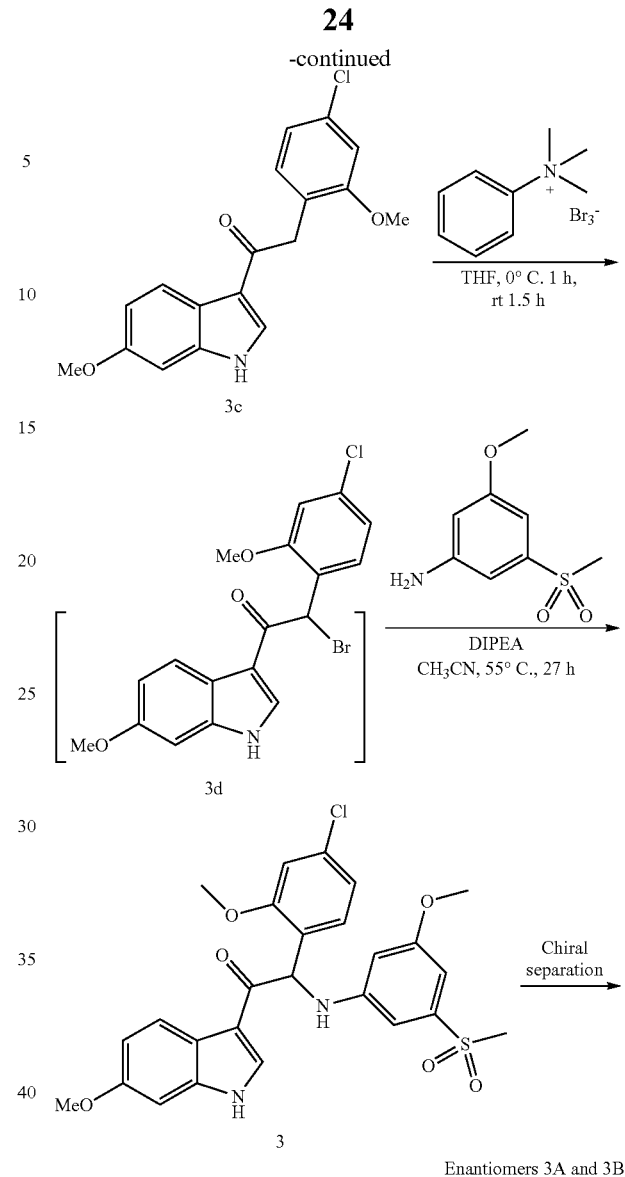

Enantiomers 3A and 3B

Synthesis of Intermediate 3a

A solution of NaHSO$_3$ (5.7 g, 54.5 mmol) in water (45 mL) was added to a stirring solution of tert-butyl 3-formyl-6-methoxy-1H-indole-1-carboxylate [CAS 847448-73-1] (10 g, 36.3 mmol) in dioxane (45 mL). After 15 min, morpholine (4.8 mL, 54.5 mmol) was added and 35 min later, sodium cyanide (NaCN) (1.96 g, 40 mmol) was added. The resulting suspension was stirred at room temperature for 3 days, until completion of the reaction. The product was filtered off and washed with a 1/1 mixture of dioxane/water (3×35 mL), and subsequently with water (3×45 mL) and dried under vacuum at 60° C. The solids were stirred up in Et$_2$O (125 mL), filtered off, washed with Et$_2$O (3×) and dried under vacuum at 50° C. to provide tert-butyl 3-(cyano(morpholino)methyl)-6-methoxy-1H-indole-1-carboxylate 3a (12.3 g).

Synthesis of Intermediate 3b

A mixture of tert-butyl 3-(cyano(morpholino)methyl)-6-methoxy-1H-indole-1-carboxylate 3a (6.0 g, 16.2 mmol) in dry DMF (80 mL) was stirred under $N_2$-atmosphere while cooling on an ice-bath. A solution of KHMDS 0.5 M in toluene (35.5 mL, 17.8 mmol) was added dropwise over 10 min. After stirring for an additional 10 min, 4-chloro-1-(chloromethyl)-2-methoxybenzene [CAS 101079-84-9] (3.09 g, 16.2 mmol) was added and the resulting mixture was stirred at room temperature for 20 h. The reaction mixture was poured out into cold water (400 mL) and the product was extracted with $Et_2O$ (2×). The combined organic layers were washed with brine, dried over $MgSO_4$, filtered, evaporated under reduced pressure and co-evaporated with xylene. The residue was purified by flash chromatography (Stationary phase: Grace Reveleris® silica 120 g, Mobile phase: heptane/EtOAc gradient 100/0 to 20/80). The desired fractions were combined, evaporated under reduced pressure and co-evaporated with dioxane to give tert-butyl 3-(2-(4-chloro-2-methoxyphenyl)-1-cyano-1-morpholinoethyl)-6-methoxy-1H-indole-1-carboxylate 3b (7.75 g).

Synthesis of Intermediate 3c

To a stirred suspension of tert-butyl 3-(2-(4-chloro-2-methoxyphenyl)-1-cyano-1-morpholinoethyl)-6-methoxy-1H-indole-1-carboxylate 3b (7.75 g, 14.7 mmol) in dioxane (40 mL) and water (20 mL) was added a solution of HCl 6 M in isopropanol (36.8 mL, 220 mmol). The resulting mixture was stirred at 60° C. for 4 h and subsequently at 80° C. for 1 h. After cooling to room temperature, the mixture was left standing for 20 h to allow crystallization of the reaction product. The product was filtered off, washed with a 1/1/1 mixture of iPrOH/$H_2O$/dioxane (2×15 mL) and dried under vacuum at 50° C. to give 2-(4-chloro-2-methoxyphenyl)-1-(6-methoxy-1H-indol-3-yl)ethanone 3c (3.67 g).

Synthesis of Compound 3 and Chiral Separation of Enantiomers 3A and 3B

A stirred mixture of 2-(4-chloro-2-methoxyphenyl)-1-(6-methoxy-1H-indol-3-yl)-ethanone 3c (2 g, 6.07 mmol) in THF (80 mL) was cooled on an ice-bath under $N_2$-atm. Phenyltrimethylammonium tribromide [CAS 4207-56-1] (2.39 g, 6.37 mmol) was added and the reaction mixture was stirred at 0° C. for 1 h and subsequently at room temperature for 1.5 h. 3-Methoxy-5-(methylsulfonyl)aniline [CAS 62606-02-4] (3.66 g, 18.2 mmol) was added and the solvent was evaporated under reduced pressure. The residue was dissolved in $CH_3CN$ (100 mL). Diisopropylethylamine (2.09 mL, 12.1 mmol) was added and the reaction mixture was heated at 55° C. for 27 h. The reaction mixture was allowed to cool to room temperature and poured out into stirring water (400 mL). The product was extracted with 2-MeTHF (2×). The combined organic layers were washed with brine, dried over $MgSO_4$, filtered and evaporated under reduced pressure. The residue (8 g) was purified by flash chromatography (stationary phase: Grace Reveleris® silica 120 g, Mobile phase: heptane/EtOAc gradient from 100/0 to 0/100). The desired fractions were combined and evaporated under reduced pressure. The residue (5.4 g) was further purified by Preparative HPLC (Stationary phase: RP XBridge® Prep C18 OBD—10 µm, 50×150 mm, Mobile phase: 0.25% $NH_4HCO_3$ solution in water, $CH_3CN$). The product fractions were combined and evaporated under reduced pressure and subsequently co-evaporated with MeOH. The residue was crystallized from a mixture of EtOAc (15 mL), $CH_3CN$ (2 mL) and MeOH (2 mL). The solids were filtered off, washed with EtOAc (3×) and dried under vacuum at 50° C. to provide 2-(4-chloro-2-methoxyphenyl)-1-(6-methoxy-1H-indol-3-yl)-2-((3-methoxy-5-(methylsulfonyl)phenyl)amino)ethanone (Compound 3, 681 mg) as a racemic mixture.

The chiral separation of the enantiomers of Compound 3 (0.63 g) was performed via Normal Phase Chiral separation (Stationary phase: AS 20 µM, Mobile phase: 100% methanol). The product fractions were combined and evaporated under reduced pressure. The first eluted enantiomer was purified by flash chromatography (Stationary phase: Grace Reveleris® silica 12 g, Mobile phase: heptane/EtOAc/EtOH gradient from 100/0/0 to 40/45/15). The desired fractions were combined and evaporated, and co-evaporated with EtOAc. The remaining oil was solidified by stirring up in $H_2O$ (4 mL) and slow addition of MeOH (1.6 mL). After stirring for 20 minutes, the product was filtered off, washed (3×) with a ½ mixture of MeOH/$H_2O$ and dried under vacuum at 50° C. to provide Enantiomer 3A (168 mg) as an amorphous solid. The second eluted enantiomer was purified by flash chromatography (Stationary phase: Grace Reveleris® silica 12 g, Mobile phase: heptane/EtOAc/EtOH gradient from 100/0/0 to 40/45/15). The desired fractions were combined, evaporated under reduced pressure and co-evaporated with EtOAc. The remaining foam was solidified by stirring up in $H_2O$ (4 mL) and slow addition of MeOH (2 mL). After stirring for 15 minutes, the product was filtered off, washed (3×) with a ½ mixture of MeOH/$H_2O$ and dried at 50° C. under vacuum to provide Enantiomer 3B (146 mg) as an amorphous solid.

Compound 3

$^1$H NMR (400 MHz, DMSO-$d_6$) δ ppm 3.09 (s, 3 H) 3.72 (s, 3 H) 3.77 (s, 3 H) 4.01 (s, 3 H) 6.21 (d, J=7.9 Hz, 1 H) 6.54-6.64 (m, 2 H) 6.83 (dd, J=8.7, 2.3 Hz, 1 H) 6.91 (t, J=1.4 Hz, 1 H) 6.94-6.99 (m, 2 H) 7.04 (d, J=7.7 Hz, 1 H) 7.12 (d, J=2.0 Hz, 1 H) 7.35 (d, J=8.1 Hz, 1 H) 8.02 (d, J=8.8 Hz, 1 H) 8.30 (s, 1 H) 11.84 (s, 1 H)
LC/MS (method LC-A): $R_t$ 1.20 min, MH$^+$ 529

Enantiomer 3A $^1$H NMR (360 MHz, DMSO-$d_6$) δ ppm 3.09 (s, 3 H) 3.72 (s, 3 H) 3.77 (s, 3 H) 4.01 (s, 3 H) 6.22 (d, J=8.1 Hz, 1 H) 6.55-6.61 (m, 2 H) 6.84 (dd, J=8.8, 2.2 Hz, 1 H) 6.91 (t, J=1.8 Hz, 1 H) 6.94-7.00 (m, 2 H) 7.07 (d, J=7.0 Hz, 1 H) 7.13 (d, J=1.8 Hz, 1 H) 7.35 (d, J=8.4 Hz, 1 H) 8.02 (d, J=8.8 Hz, 1 H) 8.32 (d, J=2.9 Hz, 1 H) 11.87 (d, J=2.6 Hz, 1 H)
LC/MS (method LC-A): $R_t$ 1.08 min, MH$^+$ 529
$[α]_D^{20}$: +134.9° (c 0.545, DMF)
Chiral SFC (method SFC-E): $R_t$ 4.31 min, MH$^+$ 529, chiral purity 100%.

Enantiomer 3B $^1$H NMR (360 MHz, DMSO-$d_6$) δ ppm 3.09 (s, 3 H) 3.72 (s, 3 H) 3.77 (s, 3 H) 4.01 (s, 3 H) 6.21 (d, J=8.1 Hz, 1 H) 6.54-6.62 (m, 2 H) 6.83 (dd, J=8.6, 2.4 Hz, 1 H) 6.91 (t, J=1.5 Hz, 1 H) 6.94-6.99 (m, 2 H) 7.07 (d, J=7.0 Hz, 1 H) 7.13 (d, J=1.8 Hz, 1 H) 7.35 (d, J=8.1 Hz, 1 H) 8.02 (d, J=8.8 Hz, 1 H) 8.32 (d, J=2.9 Hz, 1 H) 11.87 (br d, J=2.2 Hz, 1 H)
LC/MS (method LC-A): $R_t$ 1.08 min, MH$^+$ 529
$[α]_D^{20}$: −116.7° (c 0.51, DMF)

Chiral SFC (method SFC-E): R$_t$ 4.63 min, MH$^+$ 529, chiral purity 94.7%.

Example 4: Synthesis of 2-(4-chloro-2-methoxyphenyl)-2-((3-methoxy-5-(methyl-sulfonyl)phenyl) amino)-1-(6-methoxy-5-methyl-1H-indol-3-yl)ethanone (Compound 4) and Chiral Separation Into Enantiomers 4A and 4B

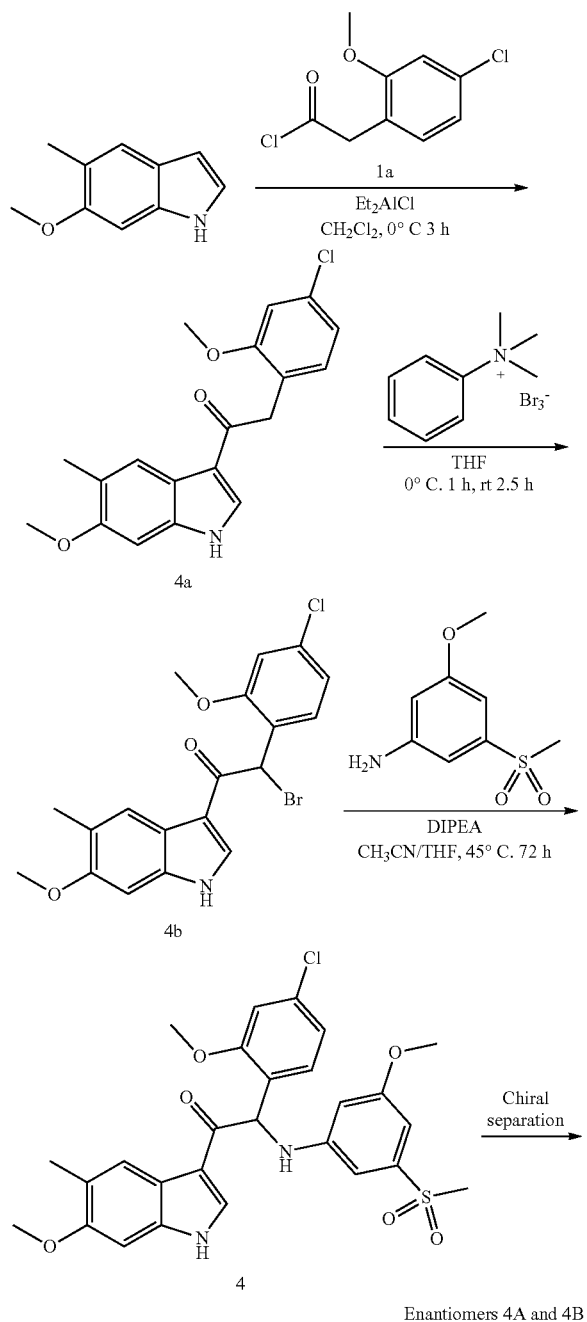

Synthesis of Intermediate 4a

Diethylaluminum chloride 1M in hexane (13.5 mL, 13.5 mmol) was added dropwise at 0° C. to a solution of 6-methoxy-5-methyl-1H-indole [CAS 1071973-95-9] (1.45 g, 9 mmol) in CH$_2$Cl$_2$ (45 mL). After 30 min at 0° C., a solution of 2-(4-chloro-2-methoxyphenyl)acetyl chloride 1a (2.4 g, 10.9 mmol) in CH$_2$Cl$_2$ (45 mL) was added slowly at 0° C. The reaction was stirred at 0° C. for 3 h. Ice-water was added and the precipitate was filtered off and washed with water. The solid was dried under vacuum to give 2-(4-chloro-2-methoxyphenyl)-1-(6-methoxy-5-methyl-1H-indol-3-yl)ethanone 4a (2.1 g).

Synthesis of Intermediate 4b

At 0° C., a solution of phenyltrimethylammonium tribromide [CAS 4207-56-1] (2.4 g, 6.4 mmol) in THF (65 mL) was added dropwise to a mixture of 2-(4-chloro-2-methoxyphenyl)-1-(6-methoxy-5-methyl-1H-indol-3-yl)ethanone 4a (2.1 g, 6.1 mmol) in THF (60 mL). The mixture was stirred at 0° C. for 1 h and at room temperature for 2.5 h. The precipitate was filtered off and washed with EtOAc. The filtrate was concentrated under reduced pressure. The residue was taken up with the minimum of diisopropylether. The precipitate was filtered off and dried under vacuum to give 2-bromo-2-(4-chloro-2-methoxyphenyl)-1-(6-methoxy-5-methyl-1H-indol-3-yl)ethanone 4b (2.36 g).

Synthesis of Compound 4 and Chiral Separation of Enantiomers 4A and 4B

A mixture of 2-bromo-2-(4-chloro-2-methoxyphenyl)-1-(6-methoxy-5-methyl-1H-indol-3-yl)ethanone 4b (4.0 g, 9.46 mmol), 3-methoxy-5-(methylsulfonyl)aniline [CAS 62606-02-4] (2.86 g, 14.2 mmol) and diisopropylethylamine (2.44 mL, 14.2 mmol) in CH$_3$CN/THF (1/1) (100 mL) was stirred at 45° C. for 72 h. The solvents were removed under reduced pressure. The residue was dissolved in EtOAc. The organic layer was washed twice with 1N HCl, washed with water, dried over MgSO$_4$, filtered and concentrated under reduced pressure. The compound was crystallized from CH$_3$CN/diisopropylether to give 2-(4-chloro-2-methoxyphenyl)-24(3-methoxy-5-(methylsulfonyl)phenyl)amino)-1-(6-methoxy-5-methyl-1H-indol-3-yl)ethanone (Compound 4, 1.1 g) as a racemic mixture. The chiral separation of the enantiomers of Compound 4 was performed via Preparative Chiral SFC (Stationary phase: (S,S)-Whelk-O1 5 µm 250× 21.1 mm, Mobile phase: 45% CO$_2$, 55% MeOH) yielding 500 mg of the first eluted enantiomer and 531 mg of the second eluted enantiomer. The first eluted enantiomer was crystallized from CH$_3$CN/Et$_2$O to afford Enantiomer 4A (401 mg). The second eluted was crystallized from CH$_3$CN/Et$_2$O to afford Enantiomer 4B (396 mg).

Compound 4

$^1$H NMR (500 MHz, DMSO-d$_6$) δ ppm 2.21 (s, 3 H) 3.09 (s, 3 H) 3.72 (s, 3 H) 3.79 (s, 3 H) 4.01 (s, 3 H) 6.20 (d, J=7.9 Hz, 1 H) 6.58 (s, 2 H) 6.88-6.93 (m, 2 H) 6.96 (dd, J=8.5, 1.9 Hz, 1 H) 7.02 (d, J=7.9 Hz, 1 H) 7.12 (d, J=1.9 Hz, 1 H) 7.34 (d, J=8.5 Hz, 1 H) 7.89 (s, 1 H) 8.24 (s, 1 H) 11.78 (br. s., 1 H)

LC/MS (method LC-C): R$_t$ 3.16 min, MH$^+$ 543
Melting point: 208° C.

Enantiomer 4A $^1$H NMR (500 MHz, DMSO-d$_6$) δ ppm 2.21 (s, 3 H) 3.09 (s, 3 H) 3.72 (s, 3 H) 3.79 (s, 3 H) 4.01 (s, 3 H) 6.20 (d, J=7.6 Hz, 1 H) 6.58 (d, J=1.6 Hz, 2 H) 6.87-6.93 (m, 2 H) 6.96 (dd, J=8.2, 1.9 Hz, 1 H) 7.02 (d, J=7.6 Hz, 1 H) 7.12 (d, J=1.9 Hz, 1 H) 7.34 (d, J=8.2 Hz, 1 H) 7.89 (s, 1 H) 8.25 (s, 1 H) 11.78 (br. s., 1 H)
LC/MS (method LC-C): $R_t$ 3.15 min, MH$^+$ 543
$[\alpha]_D^{20}$: +141.8° (c 0.3936, DMF)
Chiral SFC (method SFC-C): $R_t$ 4.95 min, MH$^+$ 543, chiral purity 100%.
Melting point: 173° C.

Enantiomer 4B $^1$H NMR (500 MHz, DMSO-d$_6$) δ ppm 2.21 (s, 3 H) 3.09 (s, 3 H) 3.72 (s, 3 H) 3.79 (s, 3 H) 4.01 (s, 3 H) 6.20 (d, J=7.9 Hz, 1 H) 6.58 (s, 2 H) 6.88-6.93 (m, 2 H) 6.96 (dd, J=8.2, 1.9 Hz, 1 H) 7.02 (d, J=7.9 Hz, 1 H) 7.12 (d, J=1.9 Hz, 1 H) 7.34 (d, J=8.2 Hz, 1 H) 7.90 (s, 1 H) 8.25 (s, 1 H) 11.79 (br. s., 1 H)
LC/MS (method LC-C): $R_t$ 3.15 min, MH$^+$ 543
$[\alpha]_D^{20}$: −142.2° (c 0.3909, DMF)
Chiral SFC (method SFC-C): $R_t$ 6.84 min, MH$^+$ 543, chiral purity 100%.
Melting point: 174° C.

Example 5: Synthesis of 2-(4-chloro-2-methoxyphenyl)-1-(5-fluoro-6-methoxy-1H-indol-3-yl)-2-((3-methoxy-5-(methylsulfonyl)phenyl)amino)ethanone (Compound 5) and Chiral Separation Into Enantiomers 5A and 5B

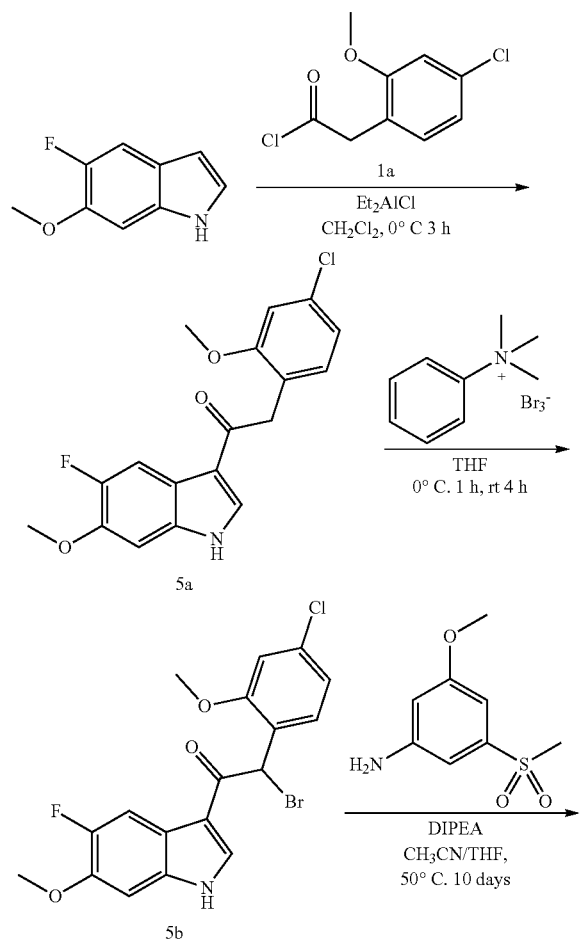

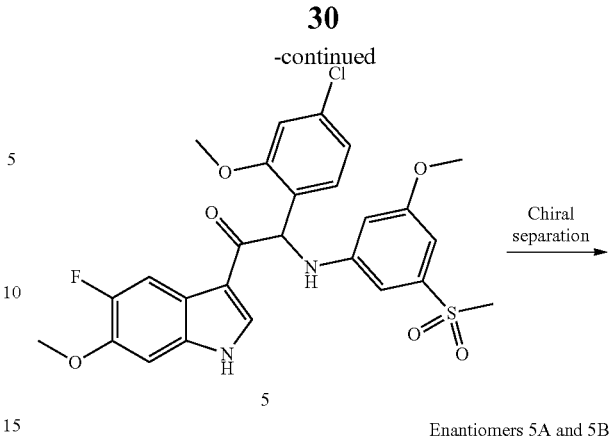

Enantiomers 5A and 5B

Synthesis of Intermediate 5a

Diethylaluminum chloride 1M in hexane (15.7 mL, 15.7 mmol) was added dropwise at 0° C. to a solution of 5-fluoro-6-methoxy-1H-indole [CAS 1211595-72-0] (2 g, 12.1 mmol) in CH$_2$Cl$_2$ (50 mL). After 30 min at 0° C., a solution of 2-(4-chloro-2-methoxyphenyl)acetyl chloride 1a (3.2 g, 14.6 mmol) in CH$_2$Cl$_2$ (50 mL) was added slowly at 0° C. The reaction was stirred at 0° C. for 3 h. Ice-water was added and the precipitate was filtered off, washed with water and the minimum of CH$_2$Cl$_2$. The solid was dried under vacuum to give 2-(4-chloro-2-methoxyphenyl)-1-(5-fluoro-6-methoxy-1H-indol-3-yl)ethanone 5a (2.82 g).

Synthesis of Intermediate 5b

At 0° C., a solution of phenyltrimethylammonium tribromide [CAS 4207-56-1] (3.5 g, 8.1 mmol) in THF (20 mL) was added dropwise to a solution of 2-(4-chloro-2-methoxyphenyl)-1-(5-fluoro-6-methoxy-1H-indol-3-yl)ethanone 5a (2.82 g, 8.1 mmol) in THF (46 mL). The mixture was stirred at 0° C. for 1 h and at room temperature for 4 h. The precipitate was filtered off and washed with EtOAc. The filtrate was concentrated under reduced pressure. The residue was dissolved in EtOAc and washed with water. The organic phase was dried over MgSO$_4$, filtered and the solvent was evaporated under reduced pressure. The residue was taken up with the minimum of EtOAc. The precipitate was filtered off and dried under vacuum to give 2-bromo-2-(4-chloro-2-methoxyphenyl)-1-(5-fluoro-6-methoxy-1H-indol-3-yl)ethanone 5b (2.5 g).

Synthesis of Compound 5 and Chiral Separation of Enantiomers 5A and 5B

A mixture of 2-bromo-2-(4-chloro-2-methoxyphenyl)-1-(5-fluoro-6-methoxy-1H-indol-3-yl)ethanone 5b (2.5 g, 5.86 mmol), 3-methoxy-5-(methylsulfonyl)aniline [CAS 62606-02-4] (1.415 g, 7.03 mmol) and diisopropylethylamine (1.515 mL, 8.79 mmol) in CH$_3$CN (55 mL) and THF (100 mL) was stirred at 50° C. for 10 days. The solvents were removed under reduced pressure. The residue was purified by flash chromatography on silica gel (15-40 µm, 80 g, Mobile phase: CH$_2$Cl$_2$/CH$_3$OH 99.25/0.75). The pure fractions were combined and evaporated. The compound was dissolved in EtOAc and stirred with HCl 1N for 15 min. A precipitate appeared, and was filtered off and dried under vacuum to give 2-(4-chloro-2-methoxyphenyl)-1-(5-fluoro-6-methoxy-1H-indol-3-yl)-2-((3-methoxy-5-(methylsulfonyl)phenyl)-amino)ethanone (Compound 5, 1.3 g) as a racemic mixture.

The chiral separation of the enantiomers of Compound 5 was performed via Preparative Chiral SFC (Stationary phase: Chiralpak® IC 5 μm 250×20 mm, Mobile phase: 55% $CO_2$, 45% MeOH). The product fractions were combined and evaporated. The first eluted enantiomer was solidified by trituration with heptane/diisopropylether. The solids were filtered off and dried under vacuum to provide Enantiomer 5A (502 mg) as an amorphous white powder. The second eluted enantiomer was solidified by trituration with heptane/diisopropylether. The solids were filtered off and dried under vacuum to provide Enantiomer 5B (490 mg) as an amorphous white powder.

Compound 5

$^1$H NMR (500 MHz, DMSO-$d_6$) δ ppm 3.09 (s, 3 H) 3.72 (s, 3 H) 3.85 (s, 3 H) 4.00 (s, 3 H) 6.21 (d, J=7.9 Hz, 1 H) 6.58 (d, J=1.3 Hz, 2 H) 6.90 (s, 1 H) 6.97 (dd, J=8.2, 1.9 Hz, 1 H) 7.06 (d, J=7.9 Hz, 1 H) 7.10-7.18 (m, 2 H) 7.34 (d, J=8.2 Hz, 1 H) 7.82 (d, J=12.0 Hz, 1 H) 8.35 (s, 1 H) 11.98 (br. s., 1 H)

LC/MS (method LC-C): $R_t$ 3.01 min, MH$^+$ 547

Melting point: 182° C.

Enantiomer 5A $^1$H NMR (500 MHz, DMSO-$d_6$) δ ppm 3.09 (s, 3 H) 3.72 (s, 3 H) 3.85 (s, 3 H) 4.00 (s, 3 H) 6.21 (d, J=7.9 Hz, 1 H) 6.58 (d, J=1.3 Hz, 2 H) 6.90 (s, 1 H) 6.97 (dd, J=8.2, 2.0 Hz, 1 H) 7.07 (d, J=7.9 Hz, 1 H) 7.11-7.17 (m, 2 H) 7.34 (d, J=8.2 Hz, 1 H) 7.82 (d, J=11.7 Hz, 1 H) 8.35 (s, 1 H) 11.98 (br. s., 1 H)

LC/MS (method LC-C): $R_t$ 3.00 min, MH$^+$ 547

$[α]_D^{20}$: +136.4° (c 0.28, DMF)

Chiral SFC (method SFC-B): $R_t$ 3.43 min, MH$^+$ 547, chiral purity 100%.

Enantiomer 5B $^1$H NMR (500 MHz, DMSO-$d_6$) δ ppm 3.09 (s, 3 H) 3.72 (s, 3 H) 3.85 (s, 3 H) 4.00 (s, 3 H) 6.21 (d, J=7.9 Hz, 1 H) 6.58 (d, J=1.3 Hz, 2 H) 6.90 (s, 1 H) 6.97 (dd, J=8.2, 2.0 Hz, 1 H) 7.07 (d, J=7.9 Hz, 1 H) 7.11-7.19 (m, 2 H) 7.34 (d, J=8.2 Hz, 1 H) 7.82 (d, J=11.7 Hz, 1 H) 8.35 (s, 1 H) 11.95 (br. s., 1 H)

LC/MS (method LC-C): $R_t$ 3.00 min, MH$^+$ 547

$[α]_D^{20}$: −126.3° (c 0.2755, DMF)

Chiral SFC (method SFC-B): $R_t$ 4.80 min, MH$^+$ 547, chiral purity 98.06%.

Example 6: Synthesis of 2-(4-chloro-2-methoxyphenyl)-2-((3-methoxy-5-(methyl-sulfonyl)phenyl)amino)-1-(6-methoxy-7-methyl-1H-indol-3-yl)ethanone (Compound 6) and Chiral Separation Into Enantiomers 6A and 6B

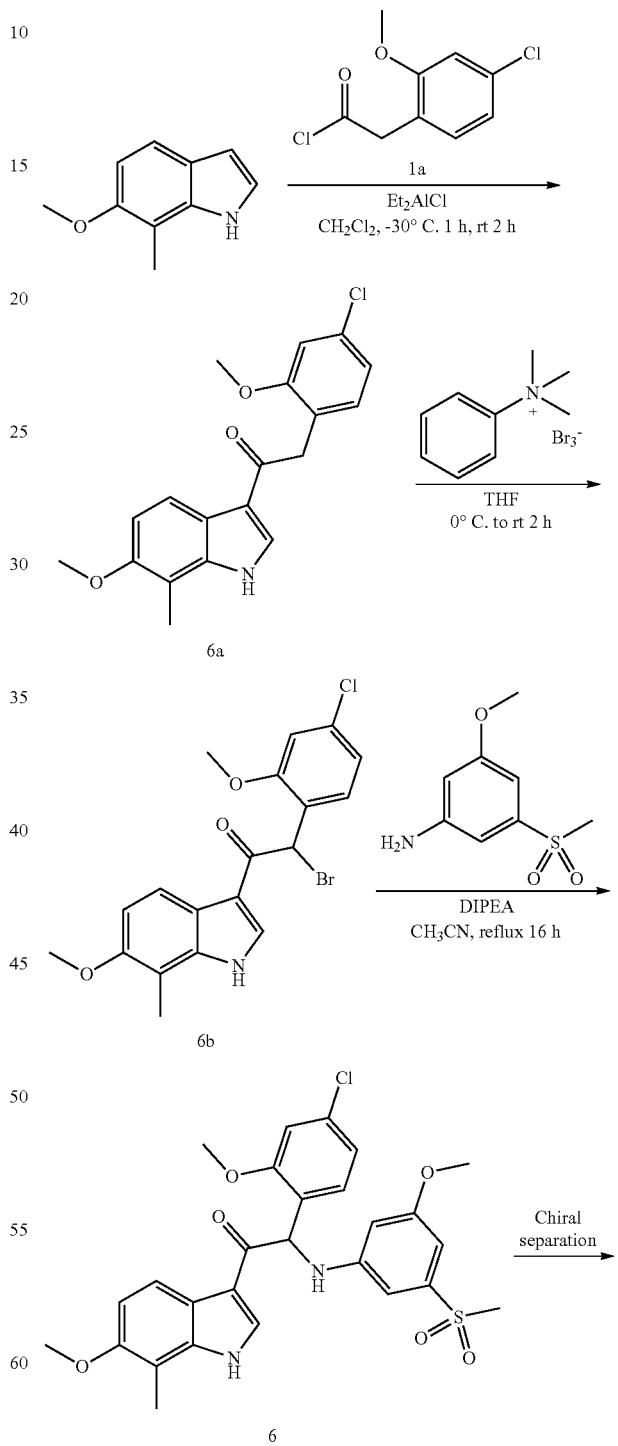

Enantiomers 6A and 6B

Synthesis of Intermediate 6a

Diethylaluminum chloride 1M in hexane (32.8 mL, 32.8 mmol) was added dropwise to a cooled (−30° C.) solution of 6-methoxy-7-methyl-1H-indole [CAS 19500-05-1] (3.53 g, 21.9 mmol) in CH$_2$Cl$_2$ (150 mL). After stirring for 15 min at −30° C., a solution of 2-(4-chloro-2-methoxyphenyl) acetyl chloride 1a (6.71 g, 30.6 mmol) in CH$_2$Cl$_2$ (150 mL) was added slowly at −30° C. The reaction was stirred at −30° C. for 1 h and was allowed to warm to room temperature while stirring for 2 h. The reaction mixture was poured out in ice-water/Rochelle salt. The mixture was filtered over a short pad of Dicalite® and the filter cake was rinsed several times with THF. The layers were separated. The aqueous layer was extracted with THF. The combined organic layers were washed with brine, water, is dried over MgSO$_4$, filtered, and evaporated under reduced pressure. The solid residue was suspended in CH$_2$Cl$_2$ (50 mL) and the solids were filtered off and washed with a small amount of C$_2$Cl$_2$ and dried under vacuum at 50° C. to give 2-(4-chloro-2-methoxyphenyl)-1-(6-methoxy-7-methyl-1H-indol-3-yl) ethanone 6a (6.85 g) as an off-white solid.

Synthesis of Intermediate 6b

At 0° C., a solution of phenyltrimethylammonium tribromide [CAS 4207-56-1] (8.2 g, 21.8 mmol) in THF (150 mL) was added dropwise to a solution of 2-(4-chloro-2-methoxyphenyl)-1-(6-methoxy-7-methyl-1H-indol-3-yl)ethanone 6a (6.8 g, 19.8 mmol) in THF (250 mL). The mixture was stirred at room temperature for 2 h. The precipitate was filtered off and washed with THF. The filtrate was concentrated under reduced pressure. The residue was crystallized from CH$_2$Cl$_2$. The precipitate was filtered off, wash with CH$_2$Cl$_2$ (2×) and dried under vacuum at 50° C. to give 2-bromo-2-(4-chloro-2-methoxyphenyl)-1-(6-methoxy-7-methyl-1H-indol-3-yl)ethanone 6b (5.38 g).

Synthesis of Compound 6 and Chiral Separation of Enantiomers 6A and 6B

A mixture of 2-bromo-2-(4-chloro-2-methoxyphenyl)-1-(6-methoxy-7-methyl-1H-indol-3-yl)ethanone 6b (1.96 g, 4.65 mmol), 3-methoxy-5-(methylsulfonyl)aniline [CAS 62606-02-4] (1.40 g, 6.97 mmol) and diisopropylethylamine (1.20 mL, 6.97 mmol) in CH$_3$CN (50 mL) was heated overnight under reflux. The solvents were removed under reduced pressure. The residue was dissolved in C$_2$Cl$_2$ and washed with 0.5N HCl and water, dried over MgSO$_4$, filtered and evaporated under reduced pressure. The residue was purified by flash chromatography on silica gel (Stationary phase: Biotage® SNAP Ultra 100 g, Mobile phase: EtOAc:EtOH (3:1)/heptane gradient 0/100 to 50/50). The pure fractions were combined and evaporated under reduced pressure to give 2-(4-chloro-2-methoxy-phenyl)-2-((3-methoxy-5-(methylsulfonyl)phenyl)amino)-1-(6-methoxy-7-methyl-1H-indol-3-yl)ethanone (Compound 6, 1.0 g) as a racemic mixture.

The chiral separation of the enantiomers of Compound 6 (1.0 g) was performed via Preparative Chiral SFC (Stationary phase: Chiralcel® Diacel OD 20×250 mm, Mobile phase: CO$_2$, EtOH containing 0.2% iPrNH$_2$). The product fractions were combined and evaporated. The first eluted enantiomer was solidified by trituration with a MeOH/water (1/1) mixture. The solids were filtered off and dried under vacuum at 50° C. to provide Enantiomer 6A (368 mg) as an amorphous white powder. The second eluted enantiomer was solidified by trituration with a MeOH/water (1/1) mixture. The solids were filtered off and dried under vacuum at 50° C. to provide Enantiomer 6B (303 mg) as an amorphous white powder.

Enantiomer 6A $^1$H NMR (360 MHz, DMSO-d$_6$) δ ppm 2.29 (s, 3 H) 3.10 (s, 3 H) 3.72 (s, 3 H) 3.80 (s, 3 H) 4.02 (s, 3 H) 6.24 (d, J=7.7 Hz, 1 H) 6.56-6.59 (m, 1 H) 6.59-6.62 (m, 1 H) 6.92 (t, J=1.6 Hz, 1 H) 6.93-6.99 (m, 2 H) 7.06 (d, J=7.7 Hz, 1 H) 7.13 (d, J=1.8 Hz, 1 H) 7.35 (d, J=8.4 Hz, 1 H) 7.94 (d, J=8.4 Hz, 1 H) 8.35 (s, 1 H) 11.91 (br s, 1 H)

LC/MS (method LC-A): R$_t$ 1.18 min, MH$^+$ 543

$[\alpha]_D^{20}$: +122.9° (c 0.48, DMF)

Chiral SFC (method SFC-E): R$_t$ 4.15 min MH$^+$ 543, chiral purity 100%.

Enantiomer 6B $^1$H NMR (360 MHz, DMSO-d$_6$) δ ppm 2.29 (s, 3 H) 3.10 (s, 3 H) 3.72 (s, 3 H) 3.80 (s, 3 H) 4.02 (s, 3 H) 6.24 (d, J=7.7 Hz, 1 H) 6.57-6.59 (m, 1 H) 6.59-6.62 (m, 1 H) 6.92 (t, J=1.8 Hz, 1 H) 6.93-7.00 (m, 2 H) 7.06 (d, J=7.7 Hz, 1 H) 7.13 (d, J=1.8 Hz, 1 H) 7.35 (d, J=8.1 Hz, 1 H) 7.94 (d, J=8.8 Hz, 1 H) 8.35 (d, J=2.2 Hz, 1 H) 11.91 (br s, 1 H)

LC/MS (method LC-A): R$_t$ 1.22 min, MH$^+$ 543

$[\alpha]_D^{20}$: −120.6° (c 0.2755, DMF)

Chiral SFC (method SFC-E): R$_t$ 4.50 min, MH$^+$ 543, chiral purity 99.35%.

Example 7: Synthesis of 2-(4-chloro-2-methoxyphenyl)-1-(6-fluoro-5-methyl-1H-indol-3-yl)-2-((3-methoxy-5-(methylsulfonyl)phenyl)amino)ethanone (Compound 7) and Chiral Separation Into Enantiomers 7A and 7B

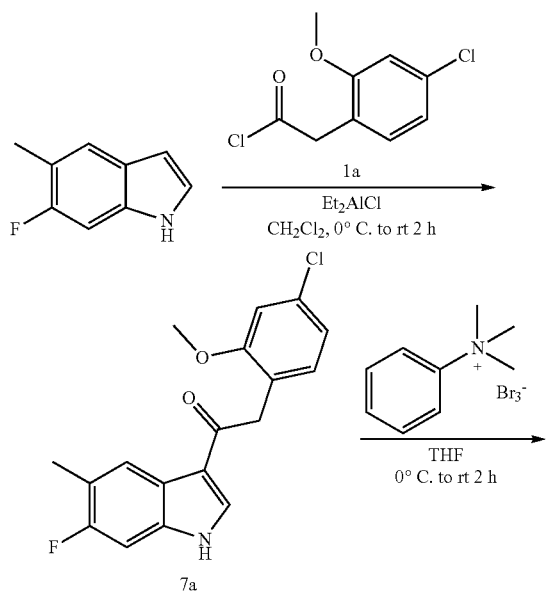

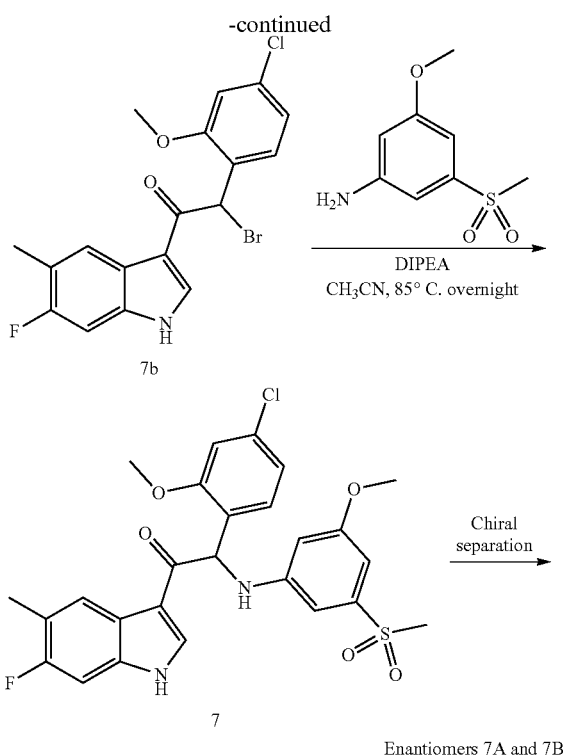

Synthesis of Intermediate 7a

A solution of 6-fluoro-5-methyl-1H-indole [CAS 162100-95-0] (1.7 g, 11.4 mmol) in $CH_2Cl_2$ (100 mL) was cooled to 0° C. under $N_2$-atmosphere. A solution of diethylaluminum chloride 1M in hexane (17.1 mL, 17.1 mmol) was added dropwise and the resulting mixture was kept at 0° C. for 15 min. A solution of 2-(4-chloro-2-methoxyphenyl)acetyl chloride 1a (3.50 g, 16 mmol) in $C_2Cl_2$ (50 mL) was added dropwise. Stirring was continued at 0° C. for 1 h and at room temperature for 2 h. The reaction mixture was poured out in a stirring ice/Rochelle salt solution. After the ice had melted, the mixture was filtered over Dicalite® and the filter cake was washed several times with THF. The filtrates were combined. The layers were separated and the organic layer was washed with brine, dried over $MgSO_4$, filtered and evaporated under reduced pressure. The solid residue was suspended in $C_2Cl_2$ (30 mL), the precipitate was filtered off and dried under vacuum at 50° C. to provide 2-(4-chloro-2-methoxyphenyl)-1-(6-fluoro-5-methyl-1H-indol-3-yl)ethanone 7a (2.76 g).

Synthesis of Intermediate 7b

A stirred solution of 2-(4-chloro-2-methoxyphenyl)-1-(6-fluoro-5-methyl-1H-indol-3-yl)ethanone 7a (2.76 g, 8.32 mmol) in THF (350 mL) was cooled to 0° C. A solution of phenyltrimethylammonium tribromide [CAS 4207-56-1] (3.44 g, 9.15 mmol) in THF (50 mL) was added dropwise. The reaction mixture was stirred at 0° C. for 2 h and at room temperature for 2 h. The solids were removed by filtration and washed with THF. The combined filtrates were evaporated under reduced pressure. The residue was mixed with EtOAc (50 mL). The solids were isolated by filtration, washed with a small amount of EtOAc and dried under vacuum at 50° C. to provide 2-bromo-2-(4-chloro-2-methoxyphenyl)-1-(6-fluoro-5-methyl-1H-indol-3-yl)ethanone 7b (3.21 g) as a white solid, which was used without further purification in the next step.

Synthesis of Compound 7 and Chiral Separation of Enantiomers 7A and 7B

A mixture 2-bromo-2-(4-chloro-2-methoxyphenyl)-1-(6-fluoro-5-methyl-1H-indol-3-yl)ethanone 7b (1.6 g, 3.90 mmol), 3-methoxy-5-(methylsulfonyl)aniline [CAS 62606-02-4] (1.18 g, 5.84 mmol) and diisopropylethylamine (671 µL, 3.90 mmol) in $CH_3CN$ (100 mL) was stirred overnight at 85° C. The reaction mixture was concentrated under reduced pressure. The residue was dissolved in $C_2Cl_2$ (100 mL), washed with 1N HCl (100 mL) and water (100 mL), dried over $MgSO_4$, filtered and evaporated under reduced pressure. The residue was purified by column chromatograph (Stationary phase: Grace Reveleris® silica 120 g, Mobile phase: EtOAc:EtOH (3:1)/heptane gradient 0/100 to 50/50). The desired fractions were combined and evaporated under reduced pressure. The residue was precipitated from $C_2Cl_2$/heptane. The solids were isolated by filtration and washed with $C_2Cl_2$/heptane (1/1). The crude product was further purified by Preparative HPLC (Stationary phase: Uptisphere® C18 ODB—10 µm, 200 g, 5 cm, Mobile phase: 0.25% $NH_4HCO_3$ solution in water, $CH_3CN$). The product fractions were combined and evaporated under reduced pressure. The solid residue was mixed with EtOAc (20 mL) and the solids were isolated by filtration and washed with a small amount of EtOAc to provide 2-(4-chloro-2-methoxyphenyl)-1-(6-fluoro-5-methyl-1H-indol-3-yl)-2-((3-methoxy-5-(methylsulfonyl)-phenyl)amino)ethanone (Compound 7, 341 mg) as a racemic mixture. The filtrate was evaporated under reduced pressure and the residue was taken up with MeOH. After stirring for 30 min, the solids were isolated by filtration to provide a second crop of Compound 7 (92 mg).

The chiral separation of the enantiomers of Compound 7 (402 mg) was performed via Normal Phase Chiral separation (Stationary phase: (S,S)-Whelk-O1, Mobile phase: 100% methanol). The product fractions were combined and evaporated to provide Enantiomer 7A as the first eluted product and Enantiomer 7B as the second eluted product. Enantiomer 7A was further purified by flash chromatography on silica gel (Stationary phase: Grace Reveleris® silica 12 g, Mobile phase: heptane/EtOAc/EtOH 100/0/0 to 40/45/15). The desired fractions were combined and evaporated under reduced pressure. The residue was triturated with $H_2O$ (1.75 mL) and MeOH (0.75 mL). The solids were filtered off, washed (2×) with $H_2O$/MeOH 7/3, and dried under vacuum at 50° C. to provide Enantiomer 7A (48 mg). Enantiomer 7B was further purified by flash chromatography on silica gel (Stationary phase: Grace Reveleris® silica 12 g, Mobile phase: heptane/EtOAc/EtOH 100/0/0 to 40/45/15). The desired fractions were combined and evaporated under reduced pressure. The residue was triturated with $H_2O$ (1.75 mL) and MeOH (0.75 mL). The solids were filtered off, washed (2×) with $H_2O$/MeOH 7/3, and dried under vacuum at 50° C. to provide Enantiomer 7B (43 mg).

Compound 7

$^1$H NMR (400 MHz, DMSO-$d_6$) δ ppm 2.30 (d, J=0.9 Hz, 3 H) 3.09 (s, 3 H) 3.72 (s, 3 H) 4.00 (s, 3 H) 6.22 (d, J=7.7 Hz, 1 H) 6.54-6.63 (m, 2 H) 6.92 (t, J=1.5 Hz, 1 H) 6.97 (dd, J=8.3, 1.9 Hz, 1 H) 7.01 (d, J=7.7 Hz, 1

H) 7.12 (d, J=1.8 Hz, 1 H) 7.22 (d, J=10.2 Hz, 1 H) 7.35 (d, J=8.4 Hz, 1 H) 8.02 (d, J=7.7 Hz, 1 H) 8.37 (s, 1 H) 11.97 (br s, 1 H)

LC/MS (method LC-A): $R_t$ 1.19 min, MH$^+$ 531

Enantiomer 7A $^1$H NMR (400 MHz, DMSO-$d_6$) δ ppm 2.30 (d, J=1.5 Hz, 3 H) 3.09 (s, 3 H) 3.72 (s, 3 H) 4.00 (s, 3 H) 6.22 (d, J=7.9 Hz, 1 H) 6.56-6.60 (m, 2 H) 6.91 (t, J=1.7 Hz, 1 H) 6.97 (dd, J=8.3, 2.1 Hz, 1 H) 7.01 (d, J=7.7 Hz, 1 H) 7.12 (d, J=2.0 Hz, 1 H) 7.22 (d, J=10.1 Hz, 1 H) 7.34 (d, J=8.1 Hz, 1 H) 8.02 (d, J=7.7 Hz, 1 H) 8.37 (s, 1 H) 11.96 (s, 1 H)

LC/MS (method LC-A): $R_t$ 1.15 min, MH$^+$ 531

[α]D20: −163.2° (c 0.435, DMF)

Chiral SFC (method SFC-E): $R_t$ 4.26 min, MH$^+$ 531, chiral purity 100%.

Enantiomer 7B $^1$H NMR (400 MHz, DMSO-$d_6$) δ ppm 2.30 (d, J=1.5 Hz, 3 H) 3.09 (s, 3 H) 3.72 (s, 3 H) 4.00 (s, 3 H) 6.22 (d, J=7.7 Hz, 1 H) 6.57-6.61 (m, 2 H) 6.92 (t, J=1.8 Hz, 1 H) 6.97 (dd, J=8.1, 2.0 Hz, 1 H) 7.01 (d, J=7.7 Hz, 1 H) 7.12 (d, J=2.0 Hz, 1 H) 7.22 (d, J=10.0 Hz, 1 H) 7.35 (d, J=8.4 Hz, 1 H) 8.02 (d, J=7.9 Hz, 1 H) 8.37 (d, J=2.4 Hz, 1 H) 11.97 (s, 1 H)

LC/MS (method LC-A): $R_t$ 1.15 min, MH$^+$ 531

$[α]_D^{20}$: +166.6° (c 0.5, DMF)

Chiral SFC (method SFC-E): $R_t$ 3.78 min, MH$^+$ 531, chiral purity 100%.

Example 8: synthesis of 2-(4-chloro-2-methoxyphenyl)-2-((3-methoxy-5-(methyl-sulfonyl)phenyl)amino)-1-(5-(trifluoromethyl)-1H-indol-3-yl)ethanone (Compound 8) and Chiral Separation Into Enantiomers 8A and 8B

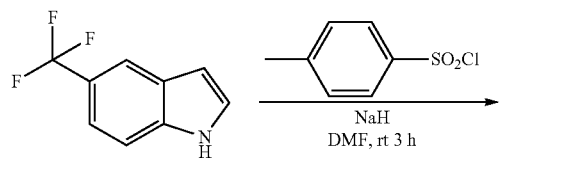

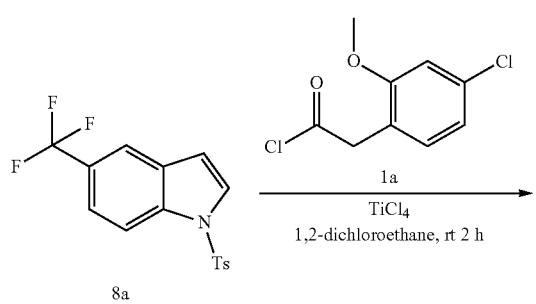

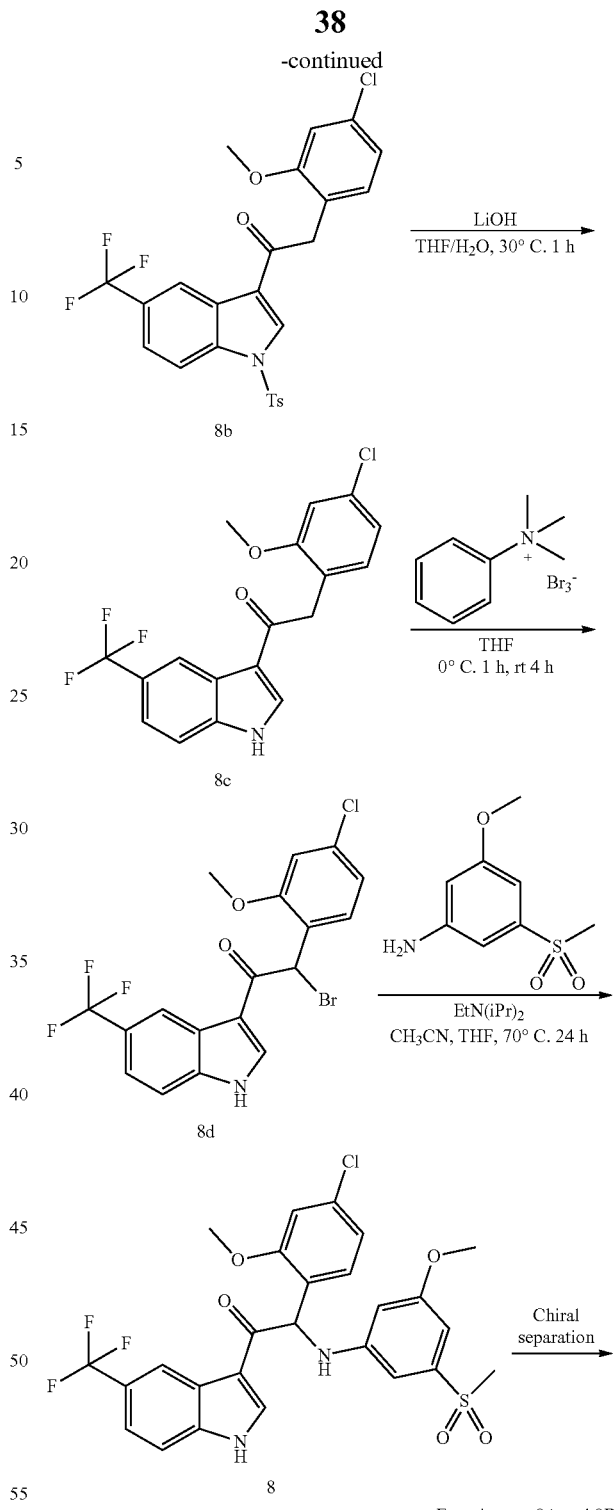

Synthesis of Intermediate 8a

At 0° C., under a $N_2$-flow, sodium hydride (2.48 g, 64.8 mmol) was added portionwise to a mixture of 5-(trifluoromethyl)-1H-indole [CAS 100846-24-0] (10 g, 54.0 mmol) in DMF (150 mL) and the reaction mixture was stirred at 0° C. for 30 min. A solution of tosyl chloride (11.3 g, 59.4 mmol) in DMF (50 mL) was added dropwise and the resulting mixture was stirred at room temperature for 3 h. At 0° C., the mixture was quenched by the addition of water. The precipitate was filtered off and dried overnight under vacuum at 70° C. to give 1-tosyl-5-(trifluoromethyl)-1H-indole 8a (18.4 g).

Synthesis of Intermediate 8b

Titanium(IV) chloride (2.4 mL, 21.9 mmol) was added dropwise at room temperature to a solution of 1-tosyl-5-(trifluoromethyl)-1H-indole 8a (3.7 g, 10.95 mmol) and 2-(4-chloro-2-methoxyphenyl)acetyl chloride 1a (4.8 g, 21.9 mmol, synthesis: see Example 1) in 1,2-dichloroethane (120 mL). The reaction was stirred at room temperature for 2 h. Ice-water was added. The reaction mixture was extracted with EtOAc. The organic layer was dried over MgSO$_4$, filtered, and the solvent was concentrated under reduced pressure. The residue was purified by column chromatography on silica gel (15-40 μm, 80 g, Mobile phase: C$_2$Cl$_2$/MeOH 99.5/0.5). The fractions containing Compound 8b were combined and the solvent was evaporated under reduced pressure. The compound was taken up with CH$_3$CN/diisopropylether. The precipitate was filtered off and dried to give 2-(4-chloro-2-methoxyphenyl)-1-(1-tosyl-5-(trifluoromethyl)-1H-indol-3-yl)ethanone 8b (2.8 g).

Synthesis of Intermediate 8c

Lithium hydroxide (0.64 g, 15.3 mmol) was added to a solution of 2-(4-chloro-2-methoxyphenyl)-1-(1-tosyl-5-(trifluoromethyl)-1H-indol-3-yl)ethanone 8b (3.2 g, 6.13 mmol) in THF (18 mL) and water (6 mL). The mixture was stirred at 30° C. for 1 h. Water and EtOAc were added. The organic layer was separated, dried over MgSO$_4$, filtered, and the solvent was evaporated under reduced pressure. The solid was taken up with diisopropylether. The precipitate was filtered off and dried to give 2-(4-chloro-2-methoxyphenyl)-1-(5-(trifluoromethyl)-1H-indol-3-yl)ethanone 8c (2.1 g).

Synthesis of Intermediate 8d

At 0° C., a solution of phenyltrimethylammonium tribromide [CAS 4207-56-1] (2.1 g, 5.7 mmol) in THF (60 mL) was added dropwise to a mixture of 2-(4-chloro-2-methoxyphenyl)-1-(5-(trifluoromethyl)-1H-indol-3-yl)ethanone 8c (2.15 g, 5.7 mmol) in THF (60 mL). The mixture was stirred at 0° C. for 1 h and at room temperature for 4 h. The precipitate was filtered off and washed with EtOAc. The combined filtrates were concentrated under reduced pressure. The residue was dissolved in EtOAc. The organic layer was washed with water, dried over MgSO$_4$, filtered and the solvent was evaporated under reduced pressure. The residue was taken up with diisopropylether. The precipitate was filtered off and dried to give 2-bromo-2-(4-chloro-2-methoxyphenyl)-1-(5-(trifluoromethyl)-1H-indol-3-yl)-ethanone 8d (2.5 g).

Synthesis of Compound 8 and Chiral Separation Into Enantiomers 8A and 8B

A mixture of 2-bromo-2-(4-chloro-2-methoxyphenyl)-1-(5-(trifluoromethyl)-1H-indol-3-yl)ethanone 8d (1 g, 2.24 mmol), 3-methoxy-5-(methylsulfonyl)aniline [CAS 62606-02-4] (496 mg, 2.46 mmol) and diisopropylethylamine (0.38 mL, 2.24 mmol) in CH$_3$CN (50 mL) and THF (25 mL) was stirred at 70° C. for 24 h. The solution was concentrated under reduced pressure. The residue was dissolved in EtOAc and the solution was washed with 1N HCl. The organic layer was separated, dried over MgSO$_4$, filtered and the solvent was evaporated under reduced pressure. The compound was crystallized from diisopropylether/CH$_3$CN to give 2-(4-chloro-2-methoxyphenyl)-2-((3-methoxy-5-(methylsulfonyl)phenyl)amino)-1-(5-(trifluoro-methyl)-1H-indol-3-yl)ethanone (Compound 8, 310 mg) as a racemic mixture. The Enantiomers of Compound 8 were separated via preparative Chiral SFC (Stationary phase: Chiralpak® AD-H 5 μm 250×20 mm, Mobile phase: 70% CO$_2$, 30% iPrOH+0.3% iPrNH$_2$) to give, after crystallization in petroleum ether/diisopropylether, 122 mg of the first eluted Enantiomer 8A and 128 mg of the second eluted Enantiomer 8B.

Compound 8

$^1$H NMR (500 MHz, DMSO-d$_6$) δ ppm 3.10 (s, 3 H) 3.72 (s, 3 H) 3.99 (s, 3 H) 6.29 (d, J=7.9 Hz, 1 H) 6.56-6.62 (m, 2 H) 6.92 (s, 1 H) 6.98 (dd, J=8.4, 2.0 Hz, 1 H) 7.09 (d, J=7.9 Hz, 1 H) 7.13 (d, J=1.9 Hz, 1 H) 7.36 (d, J=8.5 Hz, 1 H) 7.54 (dd, J=8.5, 1.6 Hz, 1 H) 7.69 (d, J=8.5 Hz, 1 H) 8.48 (s, 1 H) 8.61 (s, 1 H) 12.45 (br s, 1 H)
LC/MS (method LC-C): R$_t$ 3.19 min, MH$^+$ 567
Melting point: 168° C.

Enantiomer 8A $^1$H NMR (400 MHz, DMSO-d$_6$) δ ppm 3.09 (s, 3 H) 3.73 (s, 3 H) 3.99 (s, 3 H) 6.29 (d, J=7.6 Hz, 1 H) 6.60 (br s, 2 H) 6.92 (s, 1 H) 6.98 (dd, J=8.3, 1.8 Hz, 1 H) 7.07 (d, J=8.1 Hz, 1 H) 7.13 (d, J=1.5 Hz, 1 H) 7.36 (d, J=8.1 Hz, 1 H) 7.54 (d, J=8.1 Hz, 1 H) 7.69 (d, J=8.6 Hz, 1 H) 8.49 (s, 1 H) 8.60 (s, 1 H) 12.41 (br s, 1 H)
LC/MS (method LC-C): R$_t$ 3.25 min, MH$^+$ 567
$[\alpha]_D^{20}$: −119.2° (c 0.2727, DMF)
Chiral SFC (method SFC-F): R$_t$ 2.64 min, MH$^+$ 567, chiral purity 100%.

Enantiomer 8B $^1$H NMR (400 MHz, DMSO-d$_6$) δ ppm 3.09 (s, 3 H) 3.73 (s, 3 H) 3.99 (s, 3 H) 6.29 (d, J=8.1 Hz, 1 H) 6.60 (s, 2 H) 6.92 (s, 1 H) 6.98 (dd, J=8.6, 2.0 Hz, 1 H) 7.07 (d, J=8.1 Hz, 1 H) 7.13 (d, J=2.0 Hz, 1 H) 7.36 (d, J=8.6 Hz, 1 H) 7.54 (dd, J=8.6, 1.5 Hz, 1 H) 7.69 (d, J=8.6 Hz, 1 H) 8.49 (s, 1 H) 8.60 (s, 1 H) 12.40 (br s, 1 H)
LC/MS (method LC-C): R$_t$ 3.25 min, MH$^+$ 567
$[\alpha]_D^{20}$: +125.1° (c 0.2455, DMF)
Chiral SFC (method SFC-F): R$_t$ 3.44 min, MH$^+$ 567, chiral purity 100%.

Example 9: Synthesis of 2-(4-chloro-2-methoxyphenyl)-2-((3-methoxy-5-(methyl-sulfonyl)phenyl)amino)-1-(5-(trifluoromethoxy)-1H-indol-3-yl)ethanone (Compound 9) and Chiral Separation Into Enantiomers 9A and 9B

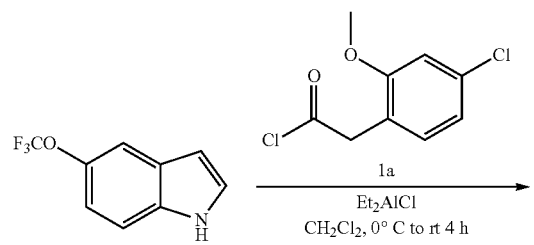

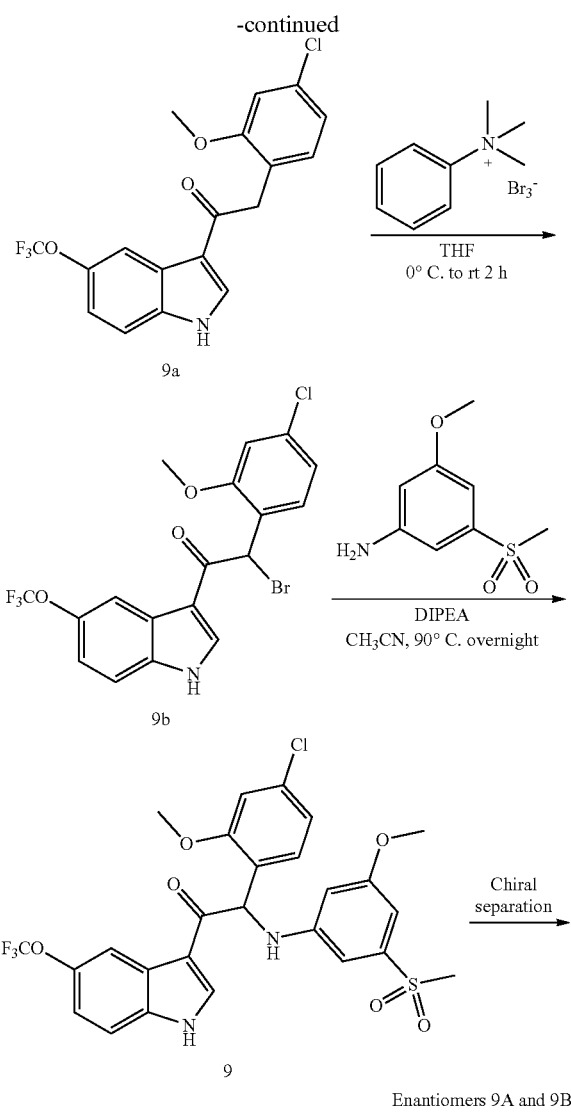

Synthesis of Intermediate 9b

A stirred solution of 2-(4-chloro-2-methoxyphenyl)-1-(5-(trifluoromethoxy)-1H-indol-3-yl)ethanone 9a (4.39 g, 11.4 mmol) in THF (200 mL) was cooled to 0° C. A solution of phenyltrimethylammonium tribromide [CAS 4207-56-1] (4.73 g, 12.6 mmol) in THF (100 mL) was added dropwise. The resulting suspension was stirred at room temperature for 2 h. The solids were removed by filtration and washed with THF. The combined filtrates were evaporated under reduced pressure. The residue was mixed with EtOAc (30 mL). The solids were isolated by filtration, washed with a small amount of EtOAc and dried under vacuum at 50° C. to provide 2-bromo-2-(4-chloro-2-methoxyphenyl)-1-(5-(trifluoromethoxy)-1H-indol-3-yl)ethanone 9b (5.0 g) as a white solid, which was used without further purification in the next step.

Synthesis of Compound 9 and Chiral Separation of Enantiomers 9A and 9B

A mixture 2-bromo-2-(4-chloro-2-methoxyphenyl)-1-(5-(trifluoromethoxy)-1H-indol-3-yl)ethanone 9b (2.5 g, 5.40 mmol), 3-methoxy-5-(methylsulfonyl)aniline [CAS 62606-02-4] (1.49 g, 7.38 mmol) and diisopropylethylamine (931 µL, 5.40 mmol) in $CH_3CN$ (100 mL) was stirred overnight at 90° C. The reaction mixture was concentrated under reduced pressure. The residue was dissolved in $CH_2Cl_2$ (100 mL), washed with 1N HCl (100 mL) and water (100 mL), dried over $MgSO_4$, filtered and evaporated under reduced pressure. The residue was purified by column chromatograph (Stationary phase: Grace Reveleris® silica 120 g, Mobile phase: EtOAc:EtOH (3:1)/heptane gradient 0/100 to 50/50). The desired fractions were combined and evaporated under reduced pressure. The residue was precipitated from EtOAc (10 mL) while stirring. The solids were isolated by filtration and washed with a small amount of EtOAc to provide 2-(4-chloro-2-methoxyphenyl)-2-((3-methoxy-5-(methylsulfonyl)phenyl)amino)-1-(5-(trifluoro-methoxy)-1H-indol-3-yl)ethanone (Compound 9, 477 mg) as a racemic mixture. The filtrate was evaporated under reduced pressure and the residue was taken up with EtOAc (5 mL). After overnight stirring, the solids were isolated by filtration and washed with EtOAc to provide a second crop of Compound 9 (216 mg).

The chiral separation of the enantiomers of Compound 9 (663 mg) was performed via Normal Phase Chiral separation (Stationary phase: AS 20 µm, Mobile phase: 100% methanol). The product fractions were combined and evaporated to provide Enantiomer 9A as the first eluted product and Enantiomer 9B as the second eluted product. Enantiomer 9A was stirred up in $H_2O$ (2 mL) and MeOH (3 mL) at 40° C. The solids were filtered off, washed (3×) with $H_2O$/MeOH 1/1, and dried under vacuum at 45° C. to provide Enantiomer 9A (151 mg). Enantiomer 9B was further purified by flash chromatography on silica gel (Stationary phase: Grace Reveleris® silica 12 g, Mobile phase: heptane/EtOAc/EtOH 100/0/0 to 40/45/15). The desired fractions were combined, evaporated under reduced pressure and co-evaporated with EtOAc. The residue was stirred up in MeOH (5 mL) and precipitated by the slow addition of $H_2O$ (4 mL). The solids were filtered off, washed (3×) with $H_2O$/MeOH 1/1, and dried under vacuum at 50° C. to provide Enantiomer 9B (132 mg).

Synthesis of Intermediate 9a

A solution of 5-(trifluoromethoxy)-1H-indole [CAS 262593-63-5] (3 g, 14.9 mmol) in $CH_2Cl_2$ (150 mL) was cooled to 0° C. under $N_2$-atmosphere. A solution of diethylaluminum chloride 1M in hexane (22.4 mL, 22.4 mmol) was added dropwise and the resulting mixture was kept at 0° C. for 15 min. A solution of 2-(4-chloro-2-methoxyphenyl)acetyl chloride 1a (4.57 g, 20.9 mmol) in $CH_2Cl_2$ (100 mL) was added dropwise. Stirring was continued at 0° C. for 1 h and the reaction mixture was subsequently stirred at room temperature for 4 h. The reaction mixture was poured out in a stirring ice/Rochelle salt solution. After the ice had melted, the mixture was filtered over Dicalite® and the filter cake was washed several times with THF. The filtrates were combined. The layers were separated and the organic layer washed with brine, dried over $MgSO_4$, filtered and evaporated under reduced pressure. The residue was triturated with $CH_2Cl_2$ (50 mL). The resulting precipitate was filtered off and dried under vacuum at 50° C. to provide 2-(4-chloro-2-methoxy-phenyl)-1-(5-(trifluoromethoxy)-1H-indol-3-yl)ethanone 9a (4.39 g).

Compound 9

$^1$H NMR (400 MHz, DMSO-$d_6$) δ ppm 3.09 (s, 3 H) 3.73 (s, 3 H) 3.99 (s, 3 H) 6.26 (d, J=7.9 Hz, 1 H) 6.57-6.62

(m, 2 H) 6.91 (t, J=1.9 Hz, 1 H) 6.98 (dd, J=8.4, 2.0 Hz, 1 H) 7.07 (d, J=7.9 Hz, 1 H) 7.13 (d, J=2.0 Hz, 1 H) 7.22 (dd, J=8.6, 2.2 Hz, 1 H) 7.36 (d, J=8.4 Hz, 1 H) 7.59 (d, J=8.8 Hz, 1 H) 8.06 (d, J=0.9 Hz, 1 H) 8.55 (s, 1 H) 12.28 (br s, 1 H)
LC/MS (method LC-A): $R_t$ 1.31 min, MH$^+$ 583

Enantiomer 9A $^1$H NMR (400 MHz, DMSO-d$_6$) δ ppm 3.09 (s, 3 H) 3.73 (s, 3 H) 3.99 (s, 3 H) 6.26 (d, J=7.9 Hz, 1 H) 6.55-6.62 (m, 2 H) 6.91 (t, J=1.5 Hz, 1 H) 6.98 (dd, J=8.4, 2.0 Hz, 1 H) 7.07 (d, J=7.9 Hz, 1 H) 7.13 (d, J=2.0 Hz, 1 H) 7.21 (dd, J=8.8, 1.8 Hz, 1 H) 7.36 (d, J=8.4 Hz, 1 H) 7.59 (d, J=8.8 Hz, 1 H) 8.07 (d, J=0.9 Hz, 1 H) 8.55 (s, 1 H) 12.29 (br s, 1 H)
LC/MS (method LC-A): $R_t$ 1.20 min, MH$^+$ 583
$[α]_D^{20}$: +130.3° (c 0.555, DMF)
Chiral SFC (method SFC-E): $R_t$ 3.10 min, MH$^+$ 583, chiral purity 100%.

Enantiomer 9B $^1$H NMR (400 MHz, DMSO-d$_6$) δ ppm 3.09 (s, 3 H) 3.73 (s, 3 H) 3.99 (s, 3 H) 6.26 (d, J=7.9 Hz, 1 H) 6.56-6.62 (m, 2 H) 6.92 (t, J=2.0 Hz, 1 H) 6.98 (dd, J=8.1, 2.0 Hz, 1 H) 7.07 (d, J=7.9 Hz, 1 H) 7.13 (d, J=2.0 Hz, 1 H) 7.22 (dd, J=8.8, 1.8 Hz, 1 H) 7.36 (d, J=8.4 Hz, 1 H) 7.59 (d, J=8.8 Hz, 1 H) 8.07 (d, J=0.9 Hz, 1 H) 8.55 (s, 1 H) 12.30 (br s, 1 H)
LC/MS (method LC-A): $R_t$ 1.20 min, MH$^+$ 583
$[α]_D^{20}$: −133.2° (c 0.5, DMF)
Chiral SFC (method SFC-E): $R_t$ 3.50 min, MH$^+$ 583, chiral purity 100%.

Example 10: Synthesis of 2-(4-chloro-2-methoxy-phenyl)-24(3-methoxy-5-(methylsulfonyl)phenyl)amino)-1-(6-methoxy-5-(trifluoromethoxy)-1H-indol-3-yl)-ethanone (Compound 10) and Chiral Separation Into Enantiomers 10A and 10B

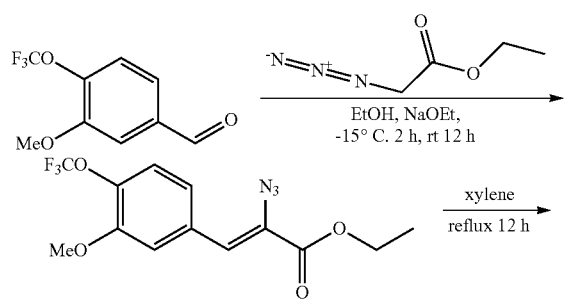

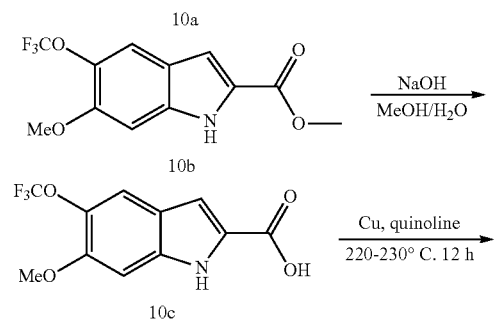

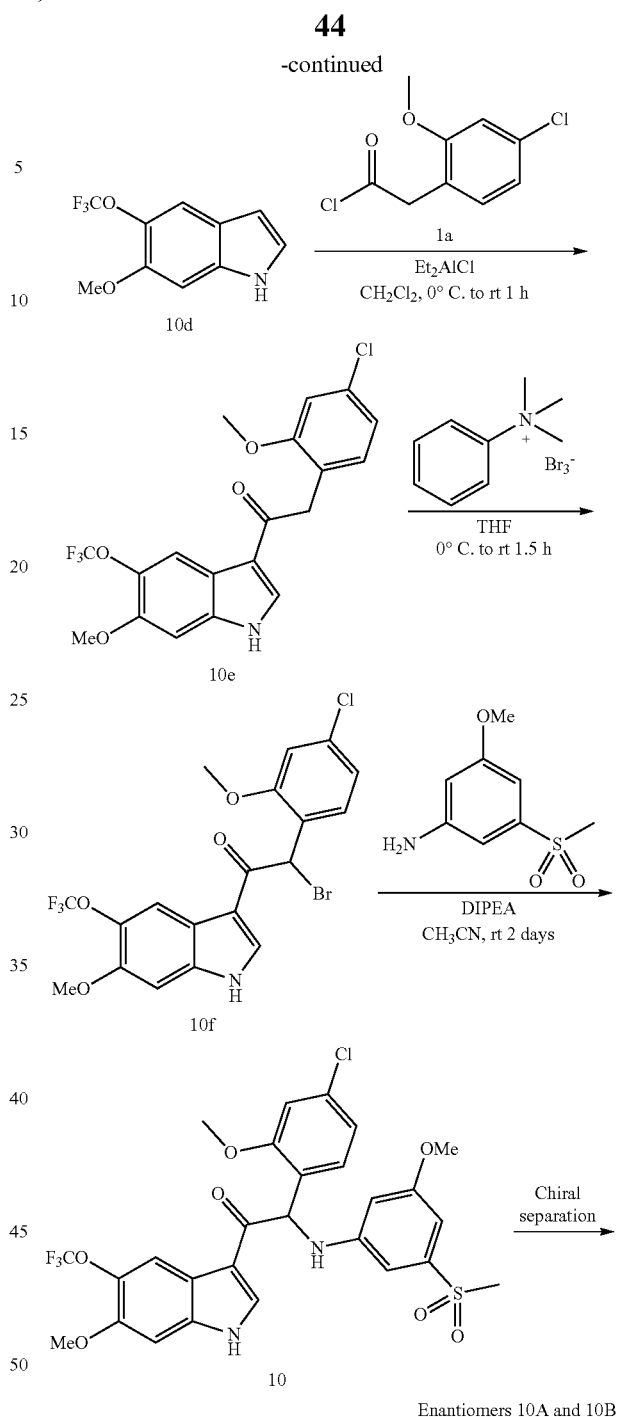

Synthesis of Intermediate 10a

To a cooled (−15° C.) solution of 3-methoxy-4-(trifluoromethoxy)benzaldehyde [CAS 853771-90-1] (50 g, 230 mmol) and ethyl azidoacetate (89 g, 690 mmol) in EtOH (400 mL) was added dropwise, over a period of 2 h, a solution of NaOEt (0.69 mol, prepared from 15.9 g of Na and 700 mL of EtOH). The reaction mixture was stirred at room temperature overnight. After cooling on an ice-bath, the reaction was quenched with a saturated NH$_4$Cl solution (1.2 L), and stirred for 10 min. The precipitate was filtered off, washed with water, and dried to give (Z)-ethyl 2-azido-3-(3-methoxy-4-(trifluoromethoxy)phenyl)acrylate 10a (32 g) as a yellowish solid.

Synthesis of Intermediate 10b

A solution of (Z)-ethyl 2-azido-3-(3-methoxy-4-(trifluoromethoxy)phenyl)acrylate 10a (3 g, 10 mmol) in xylene (40 mL) was heated under reflux overnight. After cooling to room temperature, the solvent was evaporated to dryness. The residue was triturated with hexane (50 mL) and the precipitate was filtered off to afford methyl 6-methoxy-5-(trifluoromethoxy)-1H-indole-2-carboxylate 10b (yield: 1.4-1.6 g) as a yellow solid.

Synthesis of Intermediate 10c

To a mixture of methyl 6-methoxy-5-(trifluoromethoxy)-1H-indole-2-carboxylate 10b (25 g, 87 mmol) in MeOH/$H_2O$ (2/1, 300 mL) was added NaOH (7 g, 175 mmol) and the mixture was heated under reflux until a clear solution was obtained. After cooling to room temperature, most of the methanol was removed under reduced pressure and the remaining aqueous solution was acidified with conc. HCl to pH 3-4. The product was extracted with EtOAc (2×250 mL). The combined organic layers were washed with brine, dried, and evaporated under reduced pressure to give 6-methoxy-5-(trifluoromethoxy)-1H-indole-2-carboxylic acid 10c (22.7 g) as a grey solid.

Synthesis of Intermediate 10d

A suspension of 6-methoxy-5-(trifluoromethoxy)-1H-indole-2-carboxylic acid 10c (7.5 g, 27 mmol) and Cu (1.22 g, 0.7 equiv.) in quinoline (150 mL) was heated to 220-230° C. under inert atmosphere for 12 h. After cooling to room temperature, the mixture was diluted with methyl tert-butyl ether (MTBE, 400 mL) and washed with a saturated aqueous $NaHSO_4$ solution (2×500 mL). The organic layer was dried over $MgSO_4$, filtered through short pad of silica gel, and evaporated under reduced pressure. The residue was purified by column chromatography to afford 6-methoxy-5-(trifluoromethoxy)-1H-indole 10d (3.75 g) as a yellow solid.

Synthesis of Intermediate 10e

A solution of 6-methoxy-5-(trifluoromethoxy)-1H-indole 10d (1.61 g, 6.96 mmol) in $C_2Cl_2$ (150 mL) was cooled to 0° C. under $N_2$-atmosphere. A solution of diethylaluminum chloride 1M in hexane (10.4 mL, 10.4 mmol) was added dropwise and the resulting mixture was kept at 0° C. for 30 min. A solution of 2-(4-chloro-2-methoxyphenyl)acetyl chloride 1a (2.28 g, 10.4 mmol) in $C_2Cl_2$ (75 mL) was added dropwise. Stirring was continued at 0° C. for 1 h and at room temperature for 1 h. The reaction mixture was cooled to 0° C. and a solution of potassium sodium tartrate tetrahydrate (Rochelle salt, 3.93 g, 13.9 mmol) in water (6 mL) was added dropwise. The reaction mixture was stirred for 30 min at 0° C. THF (200 mL) was added and the reaction mixture was stirred at room temperature for 20 min. $Na_2SO_4$ (25 g) was added, the mixture was stirred overnight, filtered over Dicalite® and the filter cake was washed several times with THF (4×150 mL). The filtrates were combined and evaporated under reduced pressure. The solid residue was stirred up in a mixture of diisopropyl ether (25 mL) and EtOAc (2 mL). The solids were filtered off, washed with DIPE (3×) and dried under vacuum at 50° C. to provide 2-(4-chloro-2-methoxyphenyl)-1-(6-methoxy-5-(trifluoromethoxy)-1H-indol-3-yl)ethanone 10e (3.6 g).

Synthesis of Intermediate 10f

A stirred solution of 2-(4-chloro-2-methoxyphenyl)-1-(6-methoxy-5-(trifluoro-methoxy)-1H-indol-3-yl)ethanone 10e (3.6 g, 6.53 mmol) in THF (130 mL) was cooled to 0° C., under $N_2$-atmosphere. Phenyltrimethylammonium tribromide [CAS 4207-56-1] (2.58 g, 6.85 mmol) was added and the reaction mixture was stirred at 0° C. for 45 min and at room temperature for 1.5 h. The solids were removed by filtration and washed with THF (2×). The combined filtrates were evaporated under reduced pressure to provide 2-bromo-2-(4-chloro-2-methoxyphenyl)-1-(6-methoxy-5-(trifluoromethoxy)-1H-indol-3-yl)ethanone 10f (4.16 g), which was used without further purification in the next step.

Synthesis of Compound 10 and Chiral Separation of Enantiomers 10A and 10B

A mixture 2-bromo-2-(4-chloro-2-methoxyphenyl)-1-(6-methoxy-5-(trifluoro-methoxy)-1H-indol-3-yl)ethanone 10f (4.16 g, 6.50 mmol), 3-methoxy-5-(methyl-sulfonyl)aniline [CAS 62606-02-4] (2.62 g, 13.0 mmol) and diisopropylethylamine (2.24 mL, 13.0 mmol) in $CH_3CN$ was stirred at room temperature for 2 days under $N_2$-atmosphere. Water (250 mL) was added and the product was extracted with $Et_2O$ (2×). The combined organic layers were dried over $MgSO_4$, filtered and evaporated under reduced pressure. The residue was purified by column chromatography (Stationary phase: Grace Reveleris® silica 100 g, Mobile phase: heptane/EtOAc/EtOH gradient 100/0/0 to 40/45/15). The desired fractions were combined and evaporated under reduced pressure. The residue was further purified via preparative HPLC (Stationary phase: RP XBridge® Prep C18 OBD—10 μm, 50×150 mm, Mobile phase: 0.25% $NH_4HCO_3$ solution in water, $CH_3CN$). The desired fractions were combined and evaporated under reduced pressure. The residue, containing racemic 2-(4-chloro-2-methoxyphenyl)-2-((3-methoxy-5-(methylsulfonyl)phenyl)amino)-1-(6-methoxy-5-(trifluoromethoxy)-1H-indol-3-yl)ethanone (Compound 10, 380 mg), was submitted to chiral separation by preparative SFC (Stationary phase: Chiralpak® Diacel AS 20×250 mm, Mobile phase: $CO_2$, EtOH+0.4% i$PrNH_2$). The product fractions were combined, evaporated under reduced pressure and co-evaporated with MeOH to provide Enantiomer 10A as the first eluted product and Enantiomer 10B as the second eluted product. Both enantiomers were precipitated from a solvent mixture of MeOH and water, filtered off and dried at 50° C. under vacuum to provide Enantiomer 10A (135 mg) and Enantiomer 10B (144 mg).

Enantiomer 10A $^1$H NMR (360 MHz, DMSO-$d_6$) δ ppm 3.09 (s, 3 H) 3.72 (s, 3 H) 3.87 (s, 3 H) 3.99 (s, 3 H) 6.22 (d, J=7.7 Hz, 1 H) 6.55-6.59 (m, 2 H) 6.88-6.91 (m, 1 H) 6.98 (dd, J=8.1, 1.8 Hz, 1 H) 7.08 (d, J=7.7 Hz, 1 H) 7.13 (d, J=2.2 Hz, 1 H) 7.21 (s, 1 H) 7.34 (d, J=8.1 Hz, 1 H) 8.02 (d, J=1.5 Hz, 1 H) 8.41 (s, 1 H) 12.05 (br s, 1 H)
LC/MS (method LC-A): $R_t$ 1.20 min, MH$^+$ 613
$[α]_D^{20}$: +81.4° (c 0.29, DMF)
Chiral SFC (method SFC-E): $R_t$ 3.34 min, MH$^+$ 613, chiral purity 100%.

Enantiomer 10B $^1$H NMR (360 MHz, DMSO-$d_6$) δ ppm 3.09 (s, 3 H) 3.72 (s, 3 H) 3.87 (s, 3 H) 3.99 (s, 3 H) 6.22 (d, J=7.7 Hz, 1 H) 6.55-6.60 (m, 2 H) 6.90 (t, J=1.6 Hz, 1 H) 6.98 (dd, J=8.2, 2.0 Hz, 1 H) 7.08 (d, J=7.8 Hz, 1 H) 7.13 (d, J=2.2 Hz, 1 H) 7.21 (s, 1 H) 7.34 (d, J=8.4 Hz, 1 H) 8.01 (d, J=1.1 Hz, 1 H) 8.41 (s, 1 H) 12.08 (br s, 1 H)

LC/MS (method LC-A): $R_t$ 1.20 min, MH+ 613

$[\alpha]_D^{20}$: −99.6° (c 0.261, DMF)

Chiral SFC (method SFC-E): $R_t$ 3.69 min, MH+ 613, chiral purity 100%.

Example 11: Synthesis of 2-(4-chloro-2-methoxy-phenyl)-2-((3-methoxy-5-(methyl-sulfonyl)phenyl)amino)-1-(7-methyl-5-(trifluoromethoxy)-1H-indol-3-yl)ethanone (Compound 11) and Chiral Separation Into Enantiomers 11A and 11B

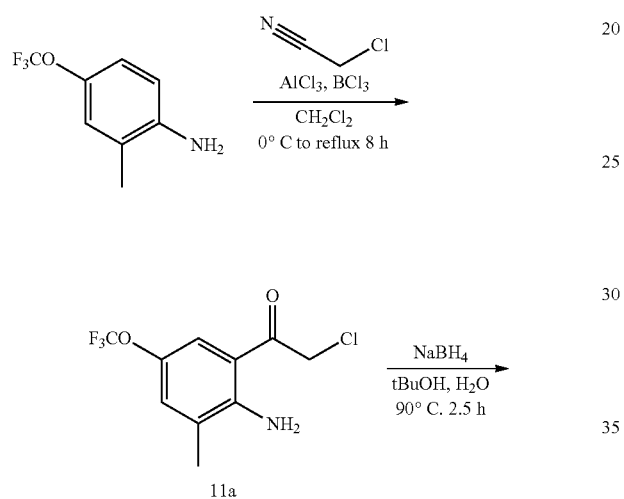

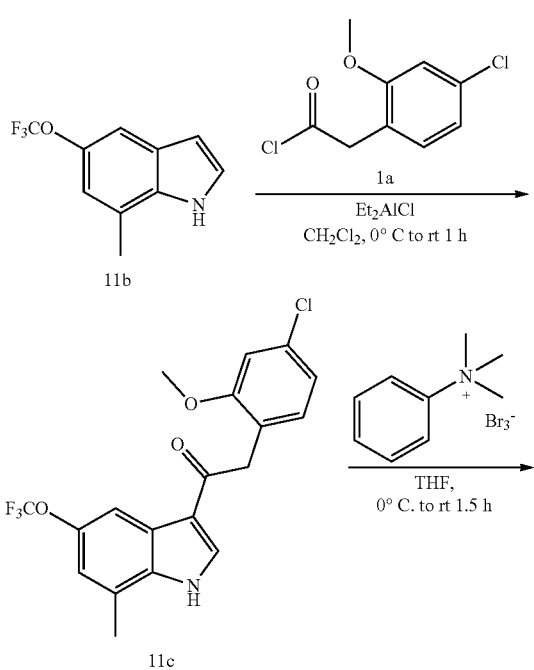

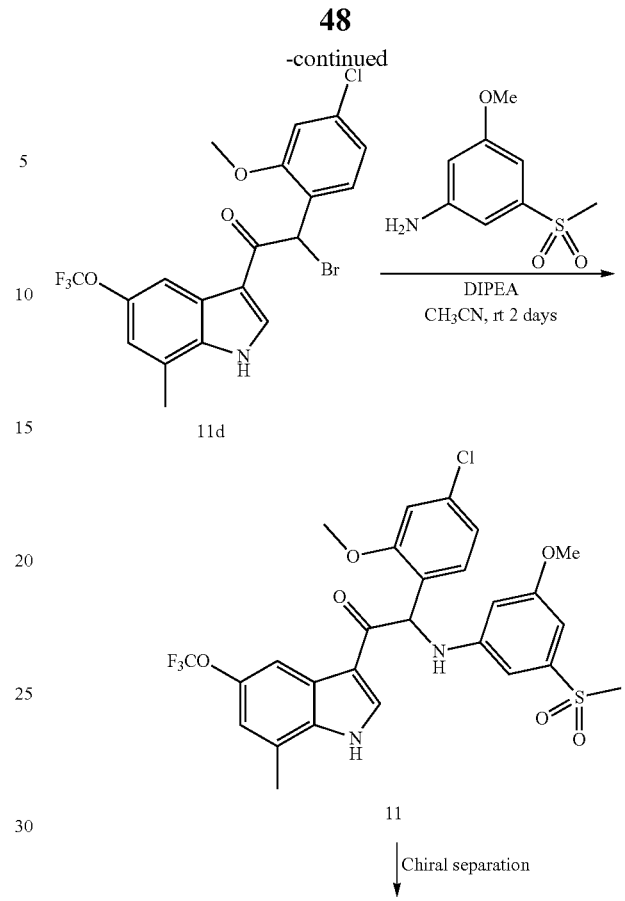

Synthesis of Intermediate 11a

A mixture of boron(III) chloride 1M in CH$_2$Cl$_2$ (25.5 mL, 25.5 mmol) and aluminum(III) chloride (3.40 g, 25.5 mmol) was diluted with CH$_2$Cl$_2$ (20 mL) and cooled on an ice-bath under N$_2$-atmosphere. A solution of 2-methyl-4-(trifluoromethoxy)aniline [CAS 86256-59-9] (4.88 g, 25.5 mmol) and chloroacetonitrile (3.24 mL, 51.0 mmol) in CH$_2$Cl$_2$ (7.5 mL) was added dropwise. After addition, the ice-bath was removed and the mixture was heated under reflux for 8 h. The mixture was cooled again to 0° C. using an ice-bath. 2N HCl (75 mL) was added dropwise, causing heavy precipitation. The resulting suspension was heated under reflux for 90 min, and cooled to room temperature. The solids were removed by filtration. The filter cake was washed with CH$_2$Cl$_2$ (4×). The filtrates were combined and the phases were separated. The organic layer was isolated, washed with an aqueous NaHCO$_3$ solution, dried over MgSO$_4$, filtered and evaporated under reduced pressure. The residue was purified by flash chromatography (Stationary phase: Biotage® SNAP Ultra Silica 100 g, Mobile phase: heptane/CH$_2$Cl$_2$ gradient 100/0 to 0/100). The desired fractions were combined and concentrated to a residual volume of 30 mL. The precipitate was filtered off, washed with heptane and CH$_2$Cl$_2$, and dried under vacuum at 50° C. to provide 1-(2-amino-3-methyl-5-(trifluoromethoxy)phenyl)-2-chloroethanone 11a (1.37 g). The filtrate was concentrated under reduced pressure. The solid residue was stirred up in a mixture of heptane (20 mL) and diisopropyl ether (3 mL), filtered off, washed with heptane (3×) and dried under vacuum at 50° C. to provide a second fraction of 11a (0.24 g).

Synthesis of Intermediate 11b

Sodium borohydride (326 mg, 8.61 mmol) was added to a stirred solution of 1-(2-amino-3-methyl-5-(trifluoromethoxy)phenyl)-2-chloroethanone 11a (1.92 g, 7.17 mmol) in tert-butanol (50 mL) and water (5 mL). The reaction mixture was stirred at room temperature for 30 min and at 90° C. for 2.5 h. Water (50 mL) was added and the product was extracted with diethyl ether (2×). The combined organic layers were washed with brine, dried over $MgSO_4$, filtered and evaporated under reduced pressure. The residue was purified by flash chromatography (Stationary phase: Biotage® SNAP Ultra Silica 25 g, Mobile phase: heptane/EtOAc gradient 100/0 to 20/80). The desired fractions were combined, concentrated under reduced pressure, co-evaporated with heptane and dried under vacuum at 50° C. to provide 7-methyl-5-(trifluoromethoxy)-1H-indole 11b (1.2 g).

Synthesis of Intermediate 11c

A mechanically stirred solution of 7-methyl-5-(trifluoromethoxy)-1H-indole 11b (1.5 g, 6.97 mmol) in $C_2Cl_2$ (100 mL) was cooled to 0° C. under $N_2$-atmosphere. A solution of diethylaluminum chloride 1M in hexane (10.5 mL, 10.5 mmol) was added dropwise and the resulting mixture was kept at 0° C. for 25 min. A solution of 2-(4-chloro-2-methoxyphenyl)acetyl chloride 1a (2.29 g, 10.5 mmol) in $C_2Cl_2$ (40 mL) was added dropwise while keeping the reaction temperature below 6° C. Stirring was continued at 0° C. for 1 h and the reaction mixture was subsequently stirred at room temperature for 1 h. The reaction mixture was cooled to 0° C. and a solution of Rochelle salt [CAS 6100-16-9] (3.94 g, 13.9 mmol) in water (4 mL) was added dropwise. After stirring for 1 h, the reaction mixture was filtered over Dicalite® and the filter cake was washed with THF (5×100 mL). The combined filtrates were evaporated under reduced pressure. The residue solidified upon standing overnight. The solids were stirred up in $CH_3CN$ (5 mL), filtered off, washed with $CH_3CN$ (3×1.5 mL) and dried under vacuum at 50° C. to provide 2-(4-chloro-2-methoxyphenyl)-1-(7-methyl-5-(trifluoromethoxy)-1H-indol-3-yl)-ethanone 11c (1.9 g).

Synthesis of Intermediate 11d

A stirred solution 2-(4-chloro-2-rnethoxyphenyl)-1-(7-methyl-5-(trifluoromethoxy)-1H-indol-3-yl)ethanone 11c (2.13 g, 5.35 mmol) in THF (80 mL) was cooled to 0° C., under $N_2$-atmosphere. Phenyltrimethylammonium tribromide [CAS 4207-56-1] (2.11 g, 5.62 mmol) was added and the reaction mixture was stirred at 0° C. for 40 min and at room temperature for 2 h. The solids were removed by filtration and washed with THF (2×). The combined filtrates were evaporated under reduced pressure to provide 2-bromo-2-(4-chloro-2-methoxyphenyl)-1-(7-methyl-5-(trifluoromethoxy)-1H-indol-3-yl)ethanone 11d (3.45 g), which was used without further purification in the next step.

Synthesis of Compound 11 and Chiral Separation of Enantiomers 11A and 11B

A mixture of 2-bromo-2-(4-chloro-2-methoxyphenyl)-1-(7-methyl-5-(trifluoro-methoxy)-1H-indol-3-yl)ethanone 11d (3.45 g, 6.87 mmol), 3-methoxy-5-(methylsulfonyl) aniline [CAS 62606-02-4] (2.76 g, 13.7 mmol) and diisopropylethylamine (2.37 mL, 13.7 mmol) in $CH_3CN$ (60 mL) was stirred at room temperature for 2 days under $N_2$-atmosphere. Water (125 mL) was added and the product was extracted with $Et_2O$ (2×). The combined organic layers were washed with brine, dried over $MgSO_4$, filtered and evaporated under reduced pressure. The residue was purified via preparative HPLC (Stationary phase: RP XBridge® Prep C18 OBD—10 µm, 50×150 mm, Mobile phase: 0.25% $NH_4HCO_3$ solution in water, $CH_3CN$). The fractions containing product were combined and evaporated under reduced pressure to provide racemic 2-(4-chloro-2-methoxyphenyl)-2-((3-methoxy-5-(methylsulfonyl)phenyl) amino)-1-(7-methyl-5-(trifluoromethoxy)-1H-indol-3-yl) ethanone (Compound 11, 1.74 g). The chiral separation of the enantiomers of Compound 11 (1.74 g) was performed via Preparative SFC (Stationary phase: Chiralpak® Diacel AS 20×250 mm, Mobile phase: $CO_2$, EtOH+0.4% iPrNH$_2$). The product fractions were combined and evaporated under reduced pressure to provide Enantiomer 11A as the first eluted product and Enantiomer 11B as the second eluted product. Both enantiomers were precipitated from a solvent mixture of MeOH and water, filtered off and dried at 50° C. under vacuum to provide Enantiomer 11A (777 mg) and Enantiomer 11B (712 mg).

Enantiomer 11A $^1$H NMR (600 MHz, DMSO-$d_6$) δ ppm 2.50 (s, 3 H) 3.09 (s, 3 H) 3.72 (s, 3 H) 4.00 (s, 3 H) 6.28 (d, J=7.8 Hz, 1 H) 6.56-6.63 (m, 2 H) 6.92 (br s, 1 H) 6.97 (dd, J=8.4, 1.9 Hz, 1 H) 7.05 (br s, 1 H) 7.07 (d, J=7.9 Hz, 1 H) 7.13 (d, J=1.9 Hz, 1 H) 7.35 (d, J=8.4 Hz, 1 H) 7.90 (br s, 1 H) 8.53 (s, 1 H) 12.41 (br s, 1 H)

LC/MS (method LC-A): $R_t$ 1.26 min, MH$^+$ 597

$[α]_D^{20}$: +81.3° (c 0.3455, DMF)

Chiral SFC (method SFC-E): $R_t$ 2.96 min, MH$^+$ 597, chiral purity 100%.

Enantiomer 11B $^1$H NMR (600 MHz, DMSO-$d_6$) δ ppm 2.51 (s, 3 H) 3.09 (s, 3 H) 3.72 (s, 3 H) 4.00 (s, 3 H) 6.28 (d, J=7.9 Hz, 1 H) 6.58-6.60 (m, 2 H) 6.92 (t, J=1.8 Hz, 1 H) 6.97 (dd, J=8.4, 1.9 Hz, 1 H) 7.05 (br s, 1 H) 7.06 (d, J=7.9 Hz, 1 H) 7.13 (d, J=2.1 Hz, 1 H) 7.35 (d, J=8.2 Hz, 1 H) 7.89 (br s, 1 H) 8.53 (s, 1 H) 12.37 (br s, 1 H)

LC/MS (method LC-A): $R_t$ 1.26 min, MH$^+$ 597

$[α]_D^{20}$: −87.4° (c 0.342, DMF)

Chiral SFC (method SFC-E): $R_t$ 3.44 min, MH$^+$ 597, chiral purity 100%.

Antiviral Activity of the Compounds of the Invention

DENV-2 Antiviral Assay

The antiviral activity of all the compounds of the invention was tested against the DENV-2 16681 strain which was labeled with enhanced green fluorescent protein (eGPF; Table 1). The culture medium consists of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 25 µL was added to 384-well plates (2500 cells/well), which already contain the antiviral compounds. Typically, these plates contain a 5-fold serial dilution of 9 dilution steps of the test compound at 200 times the final concentration in 100% DMSO (200 nL). In addition, each compound concentration is tested in quadruplicate (final concentration range: 25 µM-0.000064 µM or 2.5 µM-0.0000064 µM for the most active compounds). Finally, each plate contains wells which are assigned as virus controls (containing cells and virus in the absence of compound), cell controls (containing cells in the absence of virus and compound) and medium controls (containing medium in the absence of cells, virus and compounds). To the wells assigned as medium control, 25 µL of culture medium was added instead of Vero cells. Once the cells were added to the plates, the plates were incubated for 30 minutes at room temperature to allow the cells to distribute evenly within the wells. Next, the plates were incubated in a fully humidified incubator (37° C., 5% $CO_2$) until the next day. Then, DENV-2 strain 16681, labeled with eGFP, was added at a multiplicity of infection (MOI) of 0.5. Therefore, 15 µL of virus suspension was added to all the wells containing test compound and to the wells assigned as virus control. In parallel, 15 µL of culture medium was added to the medium and cell controls. Next, the plates were incubated for 3 days in a fully humidified incubator (37° C., 5% $CO_2$). At the day of the read out, the eGFP fluorescence was measured using an automated fluorescence microscope at 488 nm (blue laser). Using an in-house LIMS system, inhibition dose response curves for each compound were calculated and the half maximal effective concentration ($EC_{50}$) was determined. Therefore, the percent inhibition (I) for every test concentration is calculated using the following formula: $I=100*(S_T-S_{CC})/(S_{VC}-S_{CC})$; $S_T$, $S_{CC}$ and $S_{VC}$ are the amount of eGFP signal in the test compound, cell control and virus control wells, respectively. The $EC_{50}$ represents the concentration of a compound at which the virus replication is inhibited with 50%, as measured by a 50% reduction of the eGFP fluorescent intensity compared to the virus control. The $EC_{50}$ is calculated using linear interpolation.

In parallel, the toxicity of the compounds was assessed on the same plates. Once the read-out for the eGFP signal was done, 40 µL of ATPlite, a cell viability stain, was added to all wells of the 384-well plates. ATP is present in all metabolically active cells and the concentration declines very rapidly when the cells undergo necrosis or apoptosis. The ATPLite assay system is based on the production of light caused by the reaction of ATP with added luciferase and D-luciferin. The plates were incubated for 10 minutes at room temperature. Next, the plates were measured on a ViewLux. The half maximal cytotoxic concentration ($CC_{50}$) was also determined, defined as the concentration required to reduce the luminescent signal by 50% compared to that of the cell control wells. Finally, the selectivity index (SI) was determined for the compounds, which was calculated as followed: $SI=CC_{50}/EC_{50}$.

TABLE 1

$EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 1 | 0.00052 | 5 | 5.5 | 4 | 11500 | 4 |
| 1A | 0.00026 | 8 | 4.3 | 8 | 19700 | 8 |
| 1B | 0.012 | 6 | 6.5 | 6 | 530 | 6 |
| 2 | 0.00060 | 4 | 5.0 | 4 | 8410 | 4 |
| 2A | 0.00026 | 4 | 4.8 | 4 | 22000 | 4 |
| 2B | 0.026 | 4 | 7.4 | 4 | 285 | 4 |
| 3 | 0.00058 | 4 | >11 | 6 | 37700 | 4 |

TABLE 1-continued $EC_{50}$, $CC_{50}$, and SI for the compounds of the invention in the DENV-2 antiviral assay

| compound# | $EC_{50}$ (µM) | N | $CC_{50}$ (µM) | N | SI | N |
|---|---|---|---|---|---|---|
| 3A | 0.00025 | 5 | 7.2 | 5 | 29800 | 5 |
| 3B | 0.0038 | 3 | >9.7 | 5 | 2480 | 3 |
| 4 | 0.00039 | 4 | 5.9 | 4 | 14900 | 4 |
| 4A | 0.00027 | 11 | 4.2 | 13 | 16900 | 11 |
| 4B | 0.036 | 5 | 12 | 5 | 341 | 5 |
| 5 | 0.00062 | 4 | 5.5 | 4 | 8780 | 4 |
| 5A | 0.00041 | 5 | 5.0 | 5 | 12900 | 5 |
| 5B | 0.068 | 4 | 13 | 4 | 206 | 4 |
| 6A | 0.000068 | 8 | >25 | 8 | >65500 | 8 |
| 6B | 0.019 | 4 | 11 | 4 | 603 | 4 |
| 7 | 0.00047 | 4 | 3.2 | 3 | >7040 | 3 |
| 7A | 0.013 | 3 | 6.8 | 3 | 538 | 3 |
| 7B | 0.00020 | 5 | 3.2 | 5 | 18500 | 5 |
| 8 | 0.00013 | 6 | 2.9 | 7 | 30400 | 6 |
| 8A | 0.0030 | 3 | 7.4 | 3 | 2510 | 3 |
| 8B | 0.000069 | 5 | 3.4 | 5 | >40900 | 5 |
| 9 | 0.000074 | 6 | 3.1 | 8 | >39100 | 6 |
| 9A | 0.000067 | 9 | 2.9 | 9 | >37500 | 9 |
| 9B | 0.0038 | 5 | 6.2 | 6 | 1480 | 5 |
| 10A | 0.00012 | 3 | 2.6 | 3 | 22600 | 3 |
| 10B | 0.0039 | 3 | 9.8 | 3 | 2530 | 3 |
| 11A | 0.000085 | 3 | 2.6 | 3 | 30100 | 3 |
| 11B | 0.0041 | 3 | 9.2 | 3 | 2220 | 3 |

N = the number of independent experiments in which the compounds were tested.

Tetravalent Reverse Transcriptase Quantitative-PCR (RT-qPCR) Assay: Protocol A.

The antiviral activity of the compounds of the invention was tested against DENV-1 strain TC974#666 (NCPV; Table 6), DENV-2 strain 16681 (Table 7), DENV-3 strain H87 (NCPV; Table 8) and DENV-4 strains H241 (NCPV; Table 9A) and SG/06K2270DK1/2005 (Eden; Table 9B) in a RT-qPCR assay. Therefore, Vero cells were infected with either DENV-1, or -2, or -3, or -4 in the presence or absence of test compounds. At day 3 post-infection, the cells were lysed and cell lysates were used to prepare cDNA of both a viral target (the 3'UTR of DENV; Table 2) and a cellular reference gene (β-actin, Table 2). Subsequently, a duplex real time PCR was performed on a Lightcycler480 instrument. The generated Cp value is inversely proportional to the amount of RNA expression of these targets. Inhibition of DENV replication by test compound results in a shift of Cp's for the 3'UTR gene. On the other hand, if a test compound is toxic to the cells, a similar effect on β-actin expression will be observed. The comparative ΔΔCp method is used to calculate $EC_{50}$, which is based on the relative gene expression of the target gene (3'UTR) normalized with the cellular housekeeping gene (β-actin).

TABLE 2

Primers and probes used for the real-time, quantitative RT-PCR.

| Primer/probe | Target | Sequence[a,b] |
|---|---|---|
| F3utr258 | DENV 3'-UTR | 5'-CGGTTAGAGGAGACCCCTC-3' |
| R3utr425 | DENV 3'-UTR | 5'-GAGACAGCAGGATCTCTGGTC-3' |
| P3utr343 | DENV 3'-UTR | FAM-5'-AAGGACTAG-ZEN-AGGTTAGAGGAGACCCCCC-3'-IABkFQ |

TABLE 2-continued

Primers and probes used for the real-time, quantitative RT-PCR.

| Primer/probe | Target | Sequence[a,b] |
|---|---|---|
| Factin743 | β-actin | 5'-GGCCAGGTCATCACCATT-3' |
| Ractin876 | β-actin | 5'-ATGTCCACGTCACACTTCATG-3' |
| Pactin773 | β-actin | HEX-5'-TTCCGCTGC-*ZEN*-CCTGAGGCTCTC-3'-*IABkFQ* |

[a]Reporter dyes (FAM, HEX) and quenchers (ZEN and IABkFQ) elements are indicated in bold and italics.
[b]The nucleotide sequence of the primers and probes were selected from the conserved region in the 3'UTR region of the dengue virus genome, based on the alignment of 300 nucleotide sequences of the four dengue serotypes deposited in Genbank (Gong et al., 2013, Methods Mol Biol, Chapter 16).

The culture medium consisted of minimal essential medium supplemented with 2% of heat-inactivated fetal calf serum, 0.04% gentamycin (50 mg/mL) and 2 mM of L-glutamine. Vero cells, obtained from ECACC, were suspended in culture medium and 75 μL/well was added in 96-well plates (10000 cells/well), which already contain the antiviral compounds. Typically, these plates contain a 5-fold serial dilution of 9 dilution steps of the test compound at 200 times the final concentration in 100% DMSO (500 nL; final concentration range: 25 μM-0.000064 μM or 2.5 μM-0.0000064 μM for the most active compounds). In addition, each plate contains wells which are assigned as virus controls (containing cells and virus in the absence of compound) and cell controls (containing cells in the absence of virus and compound). Once the cells were added in the plates, the plates were incubated in a fully humidified incubator (37° C., 5% $CO_2$) until the next day. Dengue viruses serotype-1, 2, 3 and 4 were diluted in order to obtain a Cp of ~22-24 in the assay. Therefore, 25 μL of virus suspension was added to all the wells containing test compound and to the wells assigned as virus control. In parallel, 25 μL of culture medium was added to the cell controls. Next, the plates were incubated for 3 days in a fully humidified incubator (37° C., 5% $CO_2$). After 3 days, the supernatant was removed from the wells and the cells were washed twice with ice-cold PBS (~100 μL). The cell pellets within the 96-well plates were stored at −80° C. for at least 1 day. Next, RNA was extracted using the Cells-to-CT™ lysis kit, according to the manufacturer's guideline (Life Technologies). The cell lysates can be stored at −80° C. or immediately used in the reverse transcription step.

In preparation of the reverse transcription step, mix A (table 3A) was prepared and 7.57 μL/well was dispensed in a 96-well plate. After addition of 5 μL of the cell lysates, a five minute denaturation step at 75° C. was performed (table 3B). Afterwards, 7.43 μL of mix B was added (table 3C) and the reverse transcription step was initiated (table 3D) to generate cDNA.

Finally, a RT-qPCR mix was prepared, mix C (table 4A), and 22.02 μL/well was dispensed in 96-well LightCycler qPCR plates to which 3 μL of cDNA was added and the qPCR was performed according to the conditions in table 4B on a LightCycler 480.

Using the LightCycler software and an in-house LIMS system, dose response curves for each compound were calculated and the half maximal effective concentration ($EC_{50}$) and the half maximal cytotoxic concentration ($CC_{50}$) were determined.

TABLE 3 cDNA synthesis using Mix A, denaturation, Mix B and reverse transcription.

A
Mix A
Plates 8
Sample 828
Reaction Vol. (μl) 20

| | | | | Volume for (μl) | |
|---|---|---|---|---|---|
| | | Concentration | | 1 | x |
| Mix Item | Unit | Stock | Final | sample | samples |
| Milli-Q $H_2O$ | | | | 7.27 | 6019.56 |
| R3utr425 | μM | 20 | 0.27 | 0.15 | 124.20 |
| Ractin876 | μM | 20 | 0.27 | 0.15 | 124.20 |
| | | Volume mix/well (μl) | | 7.57 | |
| | | Cell lysates | | 5.00 | |

B
Denaturation step:

| Step | Temp | Time |
|---|---|---|
| Denaturation | 75° C. | 5' |
| Hold | 4° C. | hold |

C
Mix B
Samples 864

| | | | | Volume for (μl) | |
|---|---|---|---|---|---|
| | | Concentration | | 1 | x |
| Mix Item | Unit | Stock | Final | sample | samples |
| Expand HIFI buffer 2 | X | 10.00 | 1.00 | 2.00 | 1728.0 |
| $MgCl_2$ | mM | 25.00 | 3.50 | 2.80 | 2419.2 |
| dNTPs | mM | 10.00 | 1.00 | 2.00 | 1728.0 |
| Rnase inhibitor | U/μl | 40.00 | 1.00 | 0.50 | 432.0 |
| Expand RT | U/μl | 50.00 | 0.33 | 0.13 | 112.3 |
| | | Total Volume Mix (μl) | | 7.43 | |

D
Protocol cDNA synthesis

| Step | Temp | Time |
|---|---|---|
| Rev transc | 42° C. | 30' |
| Denaturation | 99° C. | 5' |
| Hold | 4° C. | hold |

TABLE 4 qPCR mix and protocol.

A
Mix C
Samples 833
Reaction Vol. (μl) 25

| | | | | Volume for (μl) | |
|---|---|---|---|---|---|
| | | Concentration | | 1 | x |
| Mix Item | Unit | Stock | Final | sample | samples |
| $H_2O$ PCR grade Roche | | | | 7.74 | 6447.42 |
| Roche 2xMM mix | X | 2 | 1 | 12.50 | 10412.50 |
| F3utr258 | μM | 20 | 0.3 | 0.38 | 316.54 |

TABLE 4-continued qPCR mix and protocol.

| | | | | | |
|---|---|---|---|---|---|
| R3utr425 | µM | 20 | 0.3 | 0.38 | 316.54 |
| P3utr343 | µM | 20 | 0.1 | 0.13 | 108.29 |
| Factin743 | µM | 20 | 0.3 | 0.38 | 316.54 |
| Ractin876 | µM | 20 | 0.3 | 0.38 | 316.54 |
| Pactin773 | µM | 20 | 0.1 | 0.13 | 108.29 |
| | | Volume Mix/Tube (µL) | | 22.02 | |
| | | cDNA | | 3.00 | |

B
Protocol qPCR3

| Step | Temp | Time | Ramp rate | |
|---|---|---|---|---|
| preincub/denat | 95° C. | 10 min | 4.4 | |
| Denaturation | 95° C. | 10 sec | 4.4 | 40 cycles |
| annealing | 58° C. | 1 min | 2.2 | |
| Elongation | 72° C. | 1 sec | 4.4 | |
| Cooling | 40° C. | 10 sec | 1.5 | |

Tetravalent Quantitative Reverse Transcriptase-PCR (RT-qPCR) Assay: Protocol B.

The antiviral activity of the compounds of the invention was tested against DENV-1 strain Djibouti strain (D1/H/IMTSSA/98/606; Table 6), DENV-2 strain NGC (Table 7), DENV-3 strain H87 (Table 8) and DENV-4 strain SG/06K2270DK1/2005 (Table 9B) in a RT-qPCR assay. Vero-B or Vero-M cells ($5 \times 10^4$) were seeded in 96-well plates. One day later, culture medium was replaced with 100 µL assay medium containing a 2×, 3× or 5× serial dilution of the compound (concentration range: 50 µg/mL-0.00038 µg/mL, 50 µg/mL-0.0076 µg/mL, and 50 µg/mL-0.00013 µg/mL, respectively) and 100 µL of dengue virus inoculum (DENV). Following a 2 hour incubation period, the cell monolayer was washed 3 times with assay medium to remove residual, non-adsorbed virus and cultures were further incubated for either 4 days (DENV-2 NGC) or 7 days (DENV-1 Djibouti strain D1/H/IMTSSA/98/606, DENV-3 strain H87 prototype, DENV-4 strain H241, and DENV-4 strain EDEN) in the presence of the inhibitor. Supernatant was harvested and viral RNA load was determined by real-time quantitative RT-PCR. The 50% effective concentration ($EC_{50}$), which is defined as the compound concentration that is required to inhibit viral RNA replication by 50%, was determined using logarithmic interpolation.

RNA was isolated from 100 µL (or in some circumstances 150 µL) supernatant with the NucleoSpin 96 Virus kit (Filter Service, Duren, Germany) as described by the manufacturer. The sequences of the TaqMan primers (DENV-For, DENV-Rev; Table 5) and TaqMan probes (DENV-Probe Table 5) were selected from non-structural gene 3 (NS3) or NS5, of the respective flaviviruses using Primer Express software (version 2.0; Applied Biosystems, Lennik, Belgium). The TaqMan probe was fluorescently labelled with 6-carboxyfluorescein (FAM) at the 5' end as the reporter dye, and with minor groove binder (MGB) at the 3' end as the quencher (Table 5). One-step, quantitative RT-PCR was performed in a total volume of 25 µL, containing 13.9375 µL H$_2$O, 6.25 µL master mix (Eurogentec, Seraing, Belgium), 0.375 µL forward primer, 0.375 µL reverse primer, 1 µL probe, 0.0625 µL reverse transcriptase (Eurogentec) and 3 µL sample. RT-PCR was performed using the ABI 7500 Fast Real-Time PCR System (Applied Biosystems, Branchburg, New Jersey, USA) using the following conditions: 30 min at 48° C. and 10 min at 95° C., followed by 40 cycles of 15 s at 95° C. and 1 min at 60° C. The data was analyzed using the ABI PRISM 7500 SDS software (version 1.3.1; Applied Biosystems). For absolute quantification, standard curves were generated using 10-fold dilutions of template preparations of known concentrations.

TABLE 5

Primers and probes used for real-time, quantitative RT-PCR.

| Primer/Probe | Sequence (5' → 3') [a] | Source [b] | Target |
|---|---|---|---|
| DENV-For | TCGGAGCCGGA GTTTACAAA (SEQ ID N. 1) | DENV 2 NGC | NS3 |
| DENV-Rev | TCTTAACGTCC GCCCATGAT (SEQ ID N. 2) | | |
| DENV-Probe | FAM-ATTCCACACA ATGTGGCAT-MGB (SEQ ID N. 3) | | |
| DenS | GGATAGACCAGAGAT CCTGCTGT (SEQ ID N. 4) | DENV-1, -3, -4 | NS5 |
| DenAS1-3 | CATTCCATTTT CTGGCGTTC (SEQ ID N. 5) | DENV-1, -3 | |
| DenAS4 | CAATCCATCTT GCGGCGCTC (SEQ ID N. 6) | DENV-4 | |
| DEN_1-3 probe | FAM-CAGCATCA TTCCAGGCA CAG-MGB (SEQ ID N. 7) | DENV-1, -3 | |
| DEN_4 probe | FAM-CAACATCA ATCCAGGCA CAG-MGB (SEQ ID N. 8) | DENV-4 | |

[a] Reporter dye (FAM) and quencher (MGB/TAMRA) elements are indicated in bold and italics.
[b] The nucleotide sequence and position of the primers and probes within the genome were deduced from the nucleotide sequence of DENV 2 NGC (GenBank accession no. M29095; Irie et al., 1989), dengue virus serotype 1 Djibouti strain D1/H/IMTSSA/98/606 (Genbank Accession Number AF298808), dengue virus serotype 3 strain H87 prototype (c93130), dengue virus serotype 4 strain H241 (no sequences available), dengue virus serotype 4 strain EDEN (no sequences available)

Cytotoxic Assay

Potential cytotoxic effects of the compounds were evaluated in uninfected quiescent Vero-B or Vero-M cells. Cells were seeded at $5 \times 10^4$ cells/well in a 96-well plate in the presence of two-, three- or five-fold serial dilutions (ranging from 50 µg/mL-0.0038 µg/mL, 50 µg/mL-0.0076 µg/mL, and 50 µg/mL-0.00013 µg/mL, respectively) of compound and incubated for 4 to 7 days. Culture medium was discarded and 100 µL 3-(4,5-dimethylthiazol-2-yl)-5-(3-carboxy-methoxyphenyl)-2-(4-sulfophenyl)-2H-tetrazolium/phenazinemethosulfate (MTS/PMS; Promega, Leiden, The Netherlands) in PBS was added to each well. Following a 2-hour incubation period at 37° C., the optical density was determined at 498 nm. Cytotoxic activity was calculated using the following formula: % cell viability=100× ($OD_{Compound}/OD_{CC}$), where $OD_{Compound}$ and $OD_{CC}$ correspond to the optical density at 498 nm of the uninfected cell cultures treated with compound and that of uninfected, untreated cell cultures, respectively. The 50% cytotoxic concentration (i.e., the concentration that reduces the total cell number with 50%; $CC_{50}$) was calculated using linear interpolation.

TABLE 6

EC$_{50}$, CC$_{50}$, and SI for the compounds against serotype 1 in the RT-qPCR assays

| | Protocol A RT-qPCR serotype 1 TC974#666 | | | | | | Protocol B RT-qPCR serotype 1 Djibouti | | | | | |
|---|---|---|---|---|---|---|---|---|---|---|---|---|
| compound# | EC$_{50}$ (µM) | N | CC$_{50}$ (µM) | N | SI | N | EC$_{50}$ (µM) | N | CC$_{50}$ (µM) | N | SI | N |
| 1A | 0.0025 | 9 | 5.0 | 9 | 1950 | 9 | <0.015 | 3 | 8 | 6 | >533 | 3 |
| 2A | 0.0024 | 6 | 5.3 | 6 | 2190 | 6 | <0.014 | 2 | 7.3 | 3 | >523 | 2 |
| 3A | 0.0042 | 6 | 5.5 | 5 | 1360 | 5 | ND | ND | ND | ND | ND | ND |
| 4A | 0.00097 | 8 | 5.1 | 8 | 4400 | 8 | <0.014 | 3 | 4.3 | 4 | >306 | 3 |
| 5A | 0.0036 | 6 | 5.2 | 6 | 1460 | 6 | <0.014 | 2 | 9.2 | 2 | >658 | 2 |
| 6A | 0.0016 | 6 | >10 | 6 | >8160 | 6 | <0.014 | 2 | >92 | 3 | >6571 | 2 |
| 7B | 0.00040 | 3 | 2.2 | 2 | 6600 | 2 | ND | ND | ND | ND | ND | ND |
| 8B | 0.00045 | 5 | 1.9 | 6 | 3130 | 4 | ND | ND | ND | ND | ND | ND |
| 9A | 0.00011 | 4 | 1.7 | 5 | 13300 | 4 | ND | ND | ND | ND | ND | ND |
| 10A | 0.00027 | 2 | 1.6 | 2 | 5670 | 2 | ND | ND | ND | ND | ND | ND |
| 11A | 0.00013 | 2 | >2.5 | 2 | >22100 | 2 | ND | ND | ND | ND | ND | ND |

N = the number of independent experiments in which the compounds were tested.
ND: not determined.

TABLE 7

EC$_{50}$, CC$_{50}$, and SI for the compounds against serotype 2 in the RT-qPCR assays

| | Protocol A RT-qPCR serotype 2 16681 | | | | | | Protocol B RT-qPCR serotype 2 NGC-Tongalike | | | | | |
|---|---|---|---|---|---|---|---|---|---|---|---|---|
| compound# | EC50 (µM) | N | CC50 (µM) | N | SI | N | EC50 (µM) | N | CC50 (µM) | N | SI | N |
| 1A | 0.00028 | 7 | 3.8 | 12 | 15300 | 8 | 0.00027 | 4 | 11 | 4 | >40470 | 4 |
| 2A | 0.00024 | 5 | 4.9 | 6 | 21500 | 5 | <0.00024 | 1 | 11 | 1 | >45833 | 1 |
| 3A | 0.00030 | 6 | 5.0 | 6 | 9970 | 6 | ND | ND | ND | ND | ND | ND |
| 4A | 0.00020 | 7 | 3.9 | 10 | 25400 | 6 | 0.00032 | 1 | 6.6 | 1 | 20339 | 1 |
| 5A | 0.00034 | 5 | 5.8 | 6 | 19000 | 5 | <0.00023 | 1 | ND | ND | ND | ND |
| 6A | 0.00011 | 7 | >10 | 6 | >142306 | 6 | <0.00024 | 1 | >92 | 1 | >383333 | 1 |
| 7B | 0.00017 | 3 | 2.9 | 5 | 23600 | 3 | ND | ND | ND | ND | ND | ND |
| 8B | 0.00031 | 4 | 2.2 | 6 | 23400 | 4 | ND | ND | ND | ND | ND | ND |
| 9A | 0.000057 | 3 | 2.2 | 4 | 31700 | 3 | ND | ND | ND | ND | ND | ND |
| 10A | 0.000057 | 3 | 1.6 | 3 | 28200 | 3 | ND | ND | ND | ND | ND | ND |
| 11A | 0.000051 | 3 | >2.5 | 3 | >69000 | 3 | ND | ND | ND | ND | ND | ND |

N = the number of independent experiments in which the compounds were tested.
ND: not determined.

TABLE 8

EC$_{50}$, CC$_{50}$, and SI for the compounds against serotype 3 in the RT-qPCR assays

| | Protocol A RT-qPCR serotype 3 H87 | | | | | | Protocol B RT-qPCR serotype 3 H87 | | | | | |
|---|---|---|---|---|---|---|---|---|---|---|---|---|
| compound# | EC50 (µM) | N | CC50 (µM) | N | SI | N | EC50 (µM) | N | CC50 (µM) | N | SI | N |
| 1A | 0.023 | 7 | 3.7 | 5 | 169 | 5 | <0.015 | 3 | 8.0 | 6 | >533 | 3 |
| 2A | 0.019 | 4 | 4.3 | 3 | 224 | 3 | <0.014 | 1 | 7.3 | 3 | >521 | 1 |
| 3A | 0.048 | 4 | 4.1 | 3 | 67 | 3 | ND | ND | ND | ND | ND | ND |
| 4A | 0.015 | 6 | 3.1 | 4 | 195 | 4 | <0.014 | 1 | 4.3 | 4 | >307 | 1 |
| 5A | 0.053 | 4 | 4.4 | 2 | 75 | 2 | 0.022 | 1 | 9.2 | 2 | 422 | 1 |
| 6A | 0.019 | 4 | 6.7 | 3 | 318 | 3 | <0.014 | 1 | >92 | 3 | >6571 | 1 |
| 7B | 0.0078 | 3 | 1.6 | 3 | 240 | 3 | ND | ND | ND | ND | ND | ND |
| 8B | 0.0058 | 4 | 2.1 | 3 | 609 | 3 | ND | ND | ND | ND | ND | ND |
| 9A | 0.0021 | 3 | 1.6 | 1 | 474 | 1 | ND | ND | ND | ND | ND | ND |
| 10A | 0.0037 | 3 | 1.0 | 3 | 280 | 3 | ND | ND | ND | ND | ND | ND |
| 11A | 0.0012 | 3 | >2.5 | 3 | >2630 | 3 | ND | ND | ND | ND | ND | ND |

N = the number of independent experiments in which the compounds were tested.
ND: not determined.

TABLE 9

EC$_{50}$, CC$_{50}$, and SI for the compounds against serotype 4 in the RT-gPCR assays

A

Protocol A
RT-qPCR serotyoe 4 H241

| compound# | EC50 (µM) | N | CC50 (µM) | N | SI | N |
|---|---|---|---|---|---|---|
| 1A | 0.093 | 10 | 3.0 | 9 | 30 | 9 |
| 2A | 0.083 | 6 | 3.7 | 6 | 42 | 6 |
| 3A | 0.11 | 6 | 3.8 | 4 | 37 | 4 |
| 4A | 0.053 | 11 | 2.5 | 11 | 54 | 11 |
| 5A | 0.10 | 6 | 4.0 | 6 | 39 | 6 |
| 6A | 0.095 | 7 | 7.7 | 5 | 69 | 5 |
| 7B | 0.044 | 5 | 2.2 | 5 | 53 | 5 |
| 8B | 0.015 | 5 | 1.7 | 3 | 122 | 3 |
| 9A | 0.012 | 5 | 1.5 | 5 | 121 | 5 |
| 10A | 0.011 | 3 | 1.6 | 2 | 127 | 2 |
| 11A | 0.011 | 3 | 3.1 | 3 | >250 | 3 |

B

Protocol A
RT-qPCR serotype 4 EDEN

| compound# | EC$_{50}$ (µM) | N | CC$_{50}$ (µM) | N | SI | N |
|---|---|---|---|---|---|---|
| 1A | 0.0024 | 5 | 4.6 | 5 | 1927 | 5 |
| 2A | 0.0013 | 2 | 5.0 | 2 | 3913 | 2 |
| 3A | 0.0030 | 2 | 5.4 | 2 | 1802 | 2 |
| 4A | 0.00055 | 2 | >2.5 | 1 | >4520 | 1 |
| 5A | 0.0029 | 2 | 5.5 | 2 | 1878 | 2 |
| 6A | 0.00042 | 2 | >10 | 2 | >24085 | 2 |

N = the number of independent experiments in which the compounds were tested.

The invention claimed is:

1. A pharmaceutical composition, comprising an enantiomer of a compound which is:

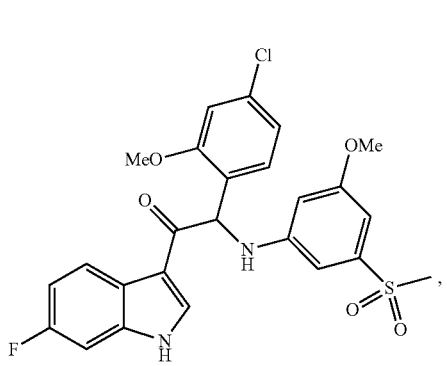
(1)

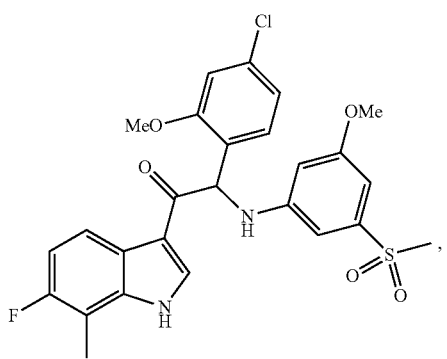
(2)

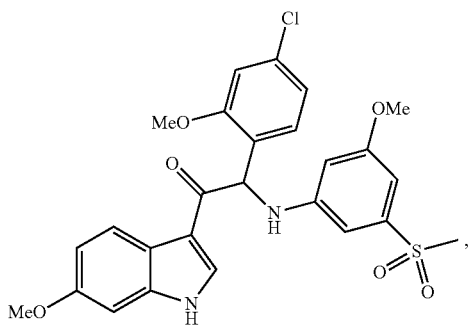
(3)

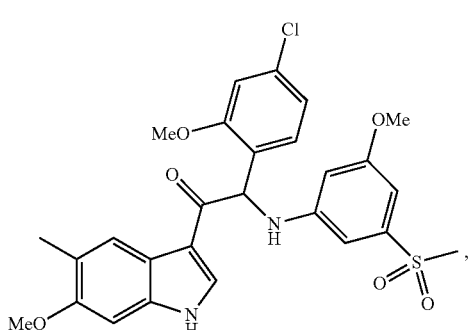
(4)

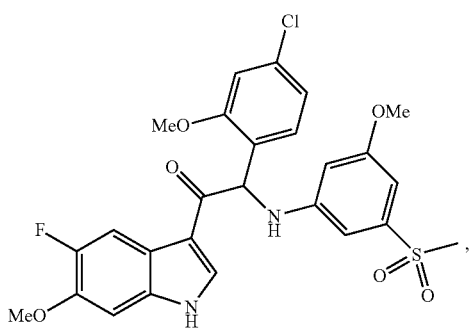
(5)

(6)
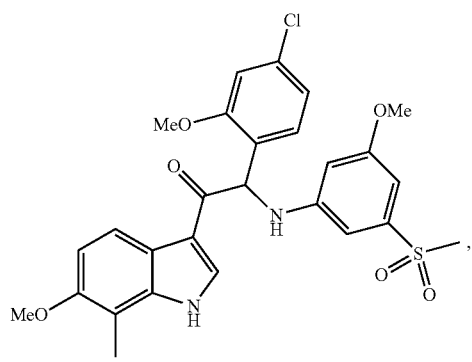
(7)
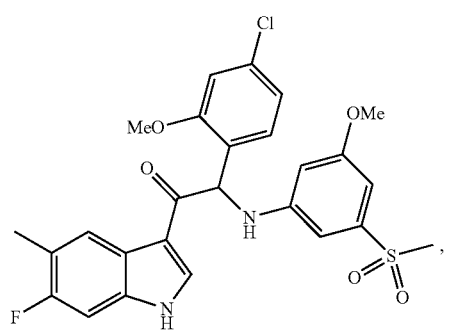
(8)
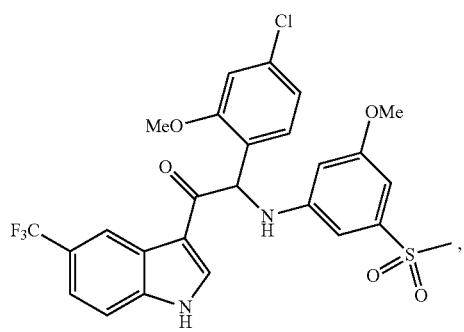
(9)
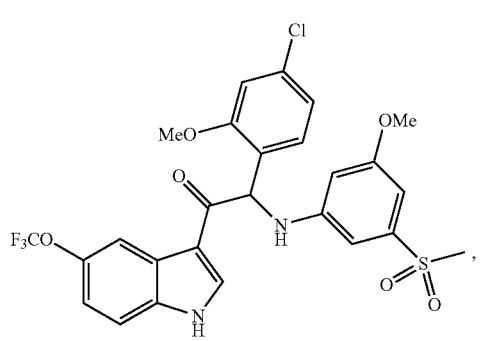
(10)
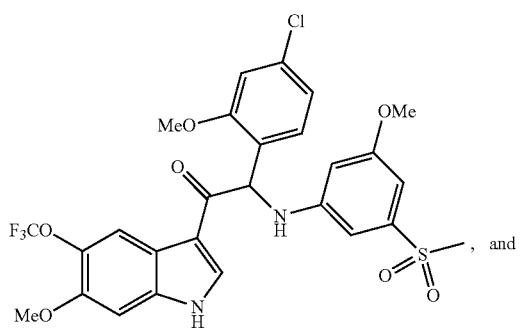
, and
(11)
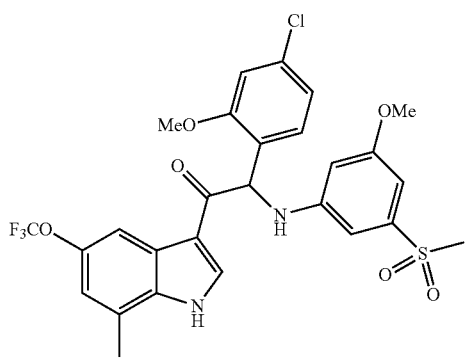
,
or a pharmaceutically acceptable salt thereof, and one or more pharmaceutically acceptable excipients, diluents, or carriers.
2. The pharmaceutical composition of claim 1, wherein the enantiomer is of a compound which is:
(1)
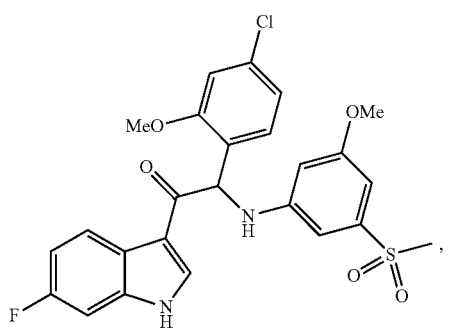
,
(2)
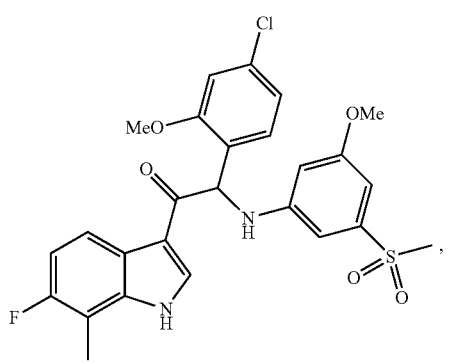
,

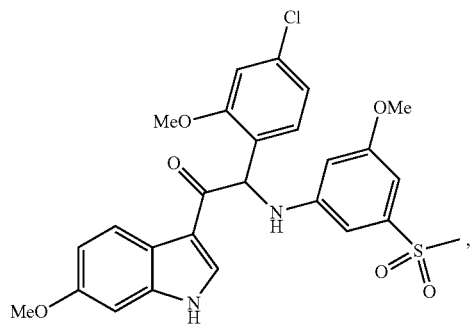
(3)
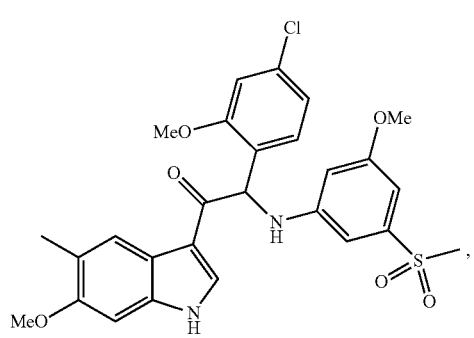
(4)
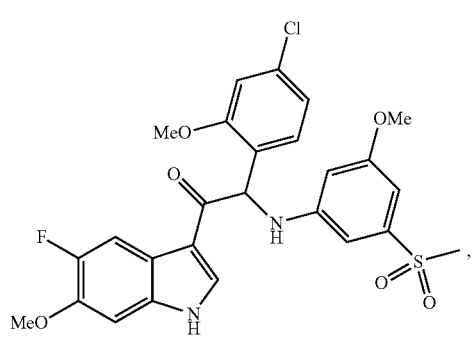
(5)
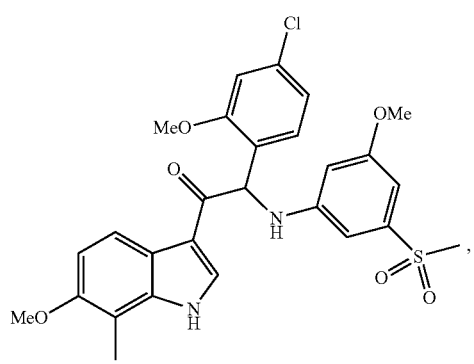
(6)
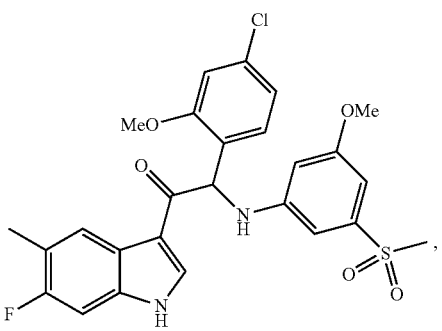
(7)
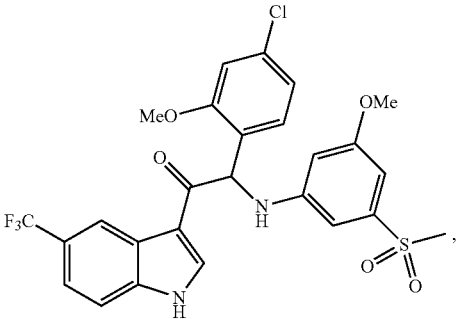
(8)
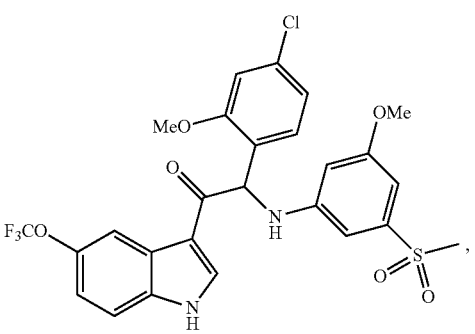
(9)
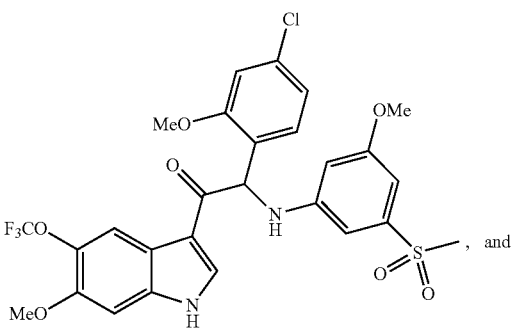
(10)
, and -continued (11)

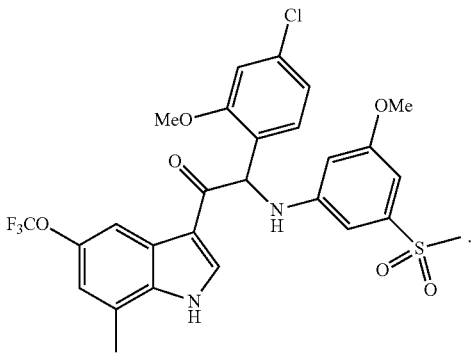

3. The pharmaceutical composition of claim 1, wherein said compound is Enantiomer 1A
wherein $^1$H NMR (500 MHZ, DMSO-$d_6$) δ ppm 3.09 (s, 3H) 3.72 (s, 3H) 4.00 (s, 3H) 6.24 (d, J=7.9 Hz, 1H) 6.59 (s, 2H) 6.91 (s, 1H) 6.97 (dd, J=8.8, 2.2 Hz, 1H) 7.02-7.10 (m, 2H) 7.12 (d, J=2.2 Hz, 1H) 7.27 (dd, J=9.6, 2.2 Hz, 1H) 7.35 (d, J=8.2 Hz, 1H) 8.14 (dd, J=8.8, 5.7 Hz, 1H) 8.44 (s, 1H) 12.10 (br. s., 1H)
LC/MS (method LC-C): $R_t$ 3.09 min, MH$^+$ 517
$[α]_D^{20}$: +130.3° (c 0.277, DMF)
Chiral SFC (method SFC-D): $R_t$ 3.41 min, MH$^+$ 517, chiral purity 100%,
or a pharmaceutically acceptable salt thereof.

4. The pharmaceutical composition of claim 1, wherein said compound is Enantiomer 1B
wherein $^1$H NMR (400 MHZ, DMSO-$d_6$) δ ppm 3.09 (s, 3H) 3.72 (s, 3H) 4.00 (s, 3H) 6.24 (d, J=7.6 Hz, 1H) 6.53-6.65 (m, 2H) 6.91 (s, 1H) 6.97 (dd, J=8.6, 2.0 Hz, 1H) 7.01-7.09 (m, 2H) 7.12 (d, J=2.0 Hz, 1H) 7.27 (dd, J=9.6, 2.0 Hz, 1H) 7.35 (d, J=8.1 Hz, 1H) 8.14 (dd, J=8.6, 5.6 Hz, 1H) 8.43 (s, 1H) 12.09 (br. s., 1H)
LC/MS (method LC-C): $R_t$ 3.09 min, MH$^+$ 517
$[α]_D^{20}$: −135.3° (c 0.283, DMF)
Chiral SFC (method SFC-D): $R_t$ 4.89 min, MH$^+$ 517, chiral purity 99.35%,
or a pharmaceutically acceptable salt thereof.

5. The pharmaceutical composition of claim 1, wherein said compound is Enantiomer 2A
wherein $^1$H NMR (500 MHZ, DMSO-$d_6$) δ ppm 2.37-2.39 (m, 3H) 3.09 (s, 3H) 3.72 (s, 3H) 4.01 (s, 3H) 6.26 (d, J=7.9 Hz, 1H) 6.54-6.63 (m, 2H) 6.92 (s, 1H) 6.97 (dd, J=8.4, 1.9 Hz, 1H) 7.02 (dd, J=9.9, 9.0 Hz, 1H) 7.07 (d, J=7.9 Hz, 1H) 7.13 (d, J=1.9 Hz, 1H) 7.35 (d, J=8.4 Hz, 1H) 7.96 (dd, J=8.5, 5.4 Hz, 1H) 8.45 (s, 1H) 12.24 (br. s., 1H)
LC/MS (method LC-C): $R_t$ 3.20 min, MH$^+$ 531
$[α]_D^{20}$: +104.5° (c 0.2545, DMF)
Chiral SFC (method SFC-A): $R_t$ 4.22 min, MH$^+$ 531, chiral purity 100%, or a pharmaceutically acceptable salt thereof.

6. The pharmaceutical composition of claim 1, wherein said compound is Enantiomer 2B
wherein $^1$H NMR (500 MHZ, DMSO-$d_6$) δ ppm 2.36-2.41 (m, 3H) 3.09 (s, 3H) 3.72 (s, 3H) 4.01 (s, 3H) 6.26 (d, J=7.9 Hz, 1H) 6.57-6.64 (m, 2H) 6.92 (s, 1H) 6.97 (dd, J=8.2, 1.9 Hz, 1 H) 6.99-7.04 (m, 1H) 7.07 (d, J=7.9 Hz, 1H) 7.13 (d, J=1.9 Hz, 1H) 7.35 (d, J=8.2 Hz, 1H) 7.96 (dd, J=8.7, 5.2 Hz, 1H) 8.45 (s, 1H) 12.24 (br. s., 1H)
LC/MS (method LC-C): $R_t$ 3.20 min, MH$^+$ 531
$[α]_D^{20}$: −104.1° (c 0.2536, DMF)
Chiral SFC (method SFC-A): $R_t$ 5.12 min, MH$^+$ 531, chiral purity 99.53%,
or a pharmaceutically acceptable salt thereof.

7. The pharmaceutical composition of claim 1, wherein said compound is Enantiomer 3A
wherein $^1$H NMR (360 MHz, DMSO-$d_6$) δ ppm 3.09 (s, 3H) 3.72 (s, 3H) 3.77 (s, 3H) 4.01 (s, 3H) 6.22 (d, J=8.1 Hz, 1H) 6.55-6.61 (m, 2H) 6.84 (dd, J=8.8, 2.2 Hz, 1H) 6.91 (t, J=1.8 Hz, 1 H) 6.94-7.00 (m, 2H) 7.07 (d, J=7.0 Hz, 1H) 7.13 (d, J=1.8 Hz, 1H) 7.35 (d, J=8.4 Hz, 1H) 8.02 (d, J=8.8 Hz, 1H) 8.32 (d, J=2.9 Hz, 1H) 11.87 (d, J=2.6 Hz, 1H)
LC/MS (method LC-A): $R_t$ 1.08 min, MH$^+$ 529
$[α]_D^{20}$: +134.9° (c 0.545, DMF)
Chiral SFC (method SFC-E): $R_t$ 4.31 min, MH$^+$ 529, chiral purity 100%,
or a pharmaceutically acceptable salt thereof.

8. The pharmaceutical composition of claim 1, wherein said compound is Enantiomer 3B
wherein $^1$H NMR (360 MHZ, DMSO-$d_6$) δ ppm 3.09 (s, 3H) 3.72 (s, 3H) 3.77 (s, 3H) 4.01 (s, 3H) 6.21 (d, J=8.1 Hz, 1H) 6.54-6.62 (m, 2H) 6.83 (dd, J=8.6, 2.4 Hz, 1H) 6.91 (t, J=1.5 Hz, 1 H) 6.94-6.99 (m, 2H) 7.07 (d, J=7.0 Hz, 1H) 7.13 (d, J=1.8 Hz, 1H) 7.35 (d, J=8.1 Hz, 1H) 8.02 (d, J=8.8 Hz, 1H) 8.32 (d, J=2.9 Hz, 1H) 11.87 (br d, J=2.2 Hz, 1H)
LC/MS (method LC-A): $R_t$ 1.08 min, MH$^+$ 529
$[α]_D^{20}$: −116.7° (c 0.51, DMF)
Chiral SFC (method SFC-E): $R_t$ 4.63 min, MH$^+$ 529, chiral purity 94.7%,
or a pharmaceutically acceptable salt thereof.

9. The pharmaceutical composition of claim 1, wherein said compound is Enantiomer 4A
wherein $^1$H NMR (500 MHZ, DMSO-$d_6$) δ ppm 2.21 (s, 3H) 3.09 (s, 3H) 3.72 (s, 3H) 3.79 (s, 3H) 4.01 (s, 3H) 6.20 (d, J=7.6 Hz, 1H) 6.58 (d, J=1.6 Hz, 2H) 6.87-6.93 (m, 2H) 6.96 (dd, J=8.2, 1.9 Hz, 1H) 7.02 (d, J=7.6 Hz, 1H) 7.12 (d, J=1.9 Hz, 1H) 7.34 (d, J=8.2 Hz, 1H) 7.89 (s, 1H) 8.25 (s, 1H) 11.78 (br. s., 1H)
LC/MS (method LC-C): $R_t$ 3.15 min, MH$^+$ 543
$[α]_D^{20}$: +141.8° (c 0.3936, DMF)
Chiral SFC (method SFC-C): $R_t$ 4.95 min, MH$^+$ 543, chiral purity 100%,
or a pharmaceutically acceptable salt thereof.

10. The pharmaceutical composition of claim 1, wherein said compound is Enantiomer 4B
wherein $^1$H NMR (500 MHZ, DMSO-$d_6$) δ ppm 2.21 (s, 3H) 3.09 (s, 3H) 3.72 (s, 3H) 3.79 (s, 3H) 4.01 (s, 3H) 6.20 (d, J=7.9 Hz, 1H) 6.58 (s, 2H) 6.88-6.93 (m, 2H) 6.96 (dd, J=8.2, 1.9 Hz, 1H) 7.02 (d, J=7.9 Hz, 1H) 7.12 (d, J=1.9 Hz, 1H) 7.34 (d, J=8.2 Hz, 1H) 7.90 (s, 1H) 8.25 (s, 1H) 11.79 (br. s., 1H)
LC/MS (method LC-C): $R_t$ 3.15 min, MH$^+$ 543
$[α]_D^{20}$: −142.2° (c 0.3909, DMF)
Chiral SFC (method SFC-C): $R_t$ 6.84 min, MH$^+$ 543, chiral purity 100%,
or a pharmaceutically acceptable salt thereof.

11. The pharmaceutical composition of claim 1, wherein said compound is Enantiomer 5A
wherein $^1$H NMR (500 MHz, DMSO-$d_6$) δ ppm 3.09 (s, 3H) 3.72 (s, 3H) 3.85 (s, 3H) 4.00 (s, 3H) 6.21 (d, J=7.9 Hz, 1H) 6.58 (d, J=1.3 Hz, 2H) 6.90 (s, 1H) 6.97 (dd, J=8.2, 2.0 Hz, 1H) 7.07 (d, J=7.9 Hz, 1H) 7.11-7.17 (m, 2H) 7.34 (d, J=8.2 Hz, 1H) 7.82 (d, J=11.7 Hz, 1H) 8.35 (s, 1H) 11.98 (br. s., 1H)
LC/MS (method LC-C): $R_t$ 3.00 min, MH$^+$ 547
$[α]_D^{20}$: +136.4° (c 0.28, DMF)

Chiral SFC (method SFC-B): R$_t$ 3.43 min, MH$^+$ 547, chiral purity 100%,
or a pharmaceutically acceptable salt thereof.

12. The pharmaceutical composition of claim 1, wherein said compound is Enantiomer 5B
wherein $^1$H NMR (500 MHZ, DMSO-d$_6$) δ ppm 3.09 (s, 3H) 3.72 (s, 3H) 3.85 (s, 3H) 4.00 (s, 3H) 6.21 (d, J=7.9 Hz, 1H) 6.58 (d, J=1.3 Hz, 2H) 6.90 (s, 1H) 6.97 (dd, J=8.2, 2.0 Hz, 1H) 7.07 (d, J=7.9 Hz, 1H) 7.11-7.19 (m, 2H) 7.34 (d, J=8.2 Hz, 1H) 7.82 (d, J=11.7 Hz, 1H) 8.35 (s, 1H) 11.95 (br. s., 1H)
LC/MS (method LC-C): R$_t$ 3.00 min, MH$^+$ 547
[α]$_D^{20}$: −126.3° (c 0.2755, DMF)
Chiral SFC (method SFC-B): R$_t$ 4.80 min, MH$^+$ 547, chiral purity 98.06%,
or a pharmaceutically acceptable salt thereof.

13. The pharmaceutical composition of claim 9, wherein said compound is Enantiomer 6A
wherein $^1$H NMR (360 MHZ, DMSO-d$_6$) δ ppm 2.29 (s, 3H) 3.10 (s, 3H) 3.72 (s, 3H) 3.80 (s, 3H) 4.02 (s, 3H) 6.24 (d, J=7.7 Hz, 1H) 6.56-6.59 (m, 1H) 6.59-6.62 (m, 1H) 6.92 (t, J=1.6 Hz, 1H) 6.93-6.99 (m, 2H) 7.06 (d, J=7.7 Hz, 1H) 7.13 (d, J=1.8 Hz, 1H) 7.35 (d, J=8.4 Hz, 1H) 7.94 (d, J=8.4 Hz, 1H) 8.35 (s, 1H) 11.91 (br s, 1H)
LC/MS (method LC-A): R$_t$ 1.18 min, MH$^+$543
[α]$_D^{20}$: +122.9° (c 0.48, DMF)
Chiral SFC (method SFC-E): R$_t$ 4.15 min MH$^+$ 543, chiral purity 100%,
or a pharmaceutically acceptable salt thereof.

14. The pharmaceutical composition of claim 1, wherein said compound is Enantiomer 6B
wherein $^1$H NMR (360 MHz, DMSO-d$_6$) δ ppm 2.29 (s, 3H) 3.10 (s, 3H) 3.72 (s, 3H) 3.80 (s, 3H) 4.02 (s, 3H) 6.24 (d, J=7.7 Hz, 1H) 6.57-6.59 (m, 1H) 6.59-6.62 (m, 1H) 6.92 (t, J=1.8 Hz, 1H) 6.93-7.00 (m, 2H) 7.06 (d, J=7.7 Hz, 1H) 7.13 (d, J=1.8 Hz, 1H) 7.35 (d, J=8.1 Hz, 1H) 7.94 (d, J=8.8 Hz, 1H) 8.35 (d, J=2.2 Hz, 1H) 11.91 (br s, 1H)
LC/MS (method LC-A): R$_t$ 1.22 min, MH$^+$543
[α]$_D^{20}$: −120.6° (c 0.2755, DMF)
Chiral SFC (method SFC-E): R$_t$ 4.50 min, MH$^+$ 543, chiral purity 99.35%,
or a pharmaceutically acceptable salt thereof.

15. The pharmaceutical composition of claim 1, wherein said compound is Enantiomer 7A
wherein $^1$H NMR (400 MHZ, DMSO-d$_6$) δ ppm 2.30 (d, J=1.5 Hz, 3H) 3.09 (s, 3H) 3.72 (s, 3H) 4.00 (s, 3H) 6.22 (d, J=7.9 Hz, 1H) 6.56-6.60 (m, 2H) 6.91 (t, J=1.7 Hz, 1H) 6.97 (dd, J=8.3, 2.1 Hz, 1H) 7.01 (d, J=7.7 Hz, 1H) 7.12 (d, J=2.0 Hz, 1H) 7.22 (d, J=10.1 Hz, 1H) 7.34 (d, J=8.1 Hz, 1H) 8.02 (d, J=7.7 Hz, 1H) 8.37 (s, 1H) 11.96 (s, 1H)
LC/MS (method LC-A): R$_t$ 1.15 min, MH$^+$ 531
[α]$_D^{20}$: −163.2° (c 0.435, DMF)
Chiral SFC (method SFC-E): R$_t$ 4.26 min, MH$^+$ 531, chiral purity 100%,
or a pharmaceutically acceptable salt thereof.

16. The pharmaceutical composition of claim 1, wherein said compound is Enantiomer 7B
wherein $^1$H NMR (400 MHZ, DMSO-d$_6$) δ ppm 2.30 (d, J=1.5 Hz, 3H) 3.09 (s, 3H) 3.72 (s, 3H) 4.00 (s, 3H) 6.22 (d, J=7.7 Hz, 1H) 6.57-6.61 (m, 2H) 6.92 (t, J=1.8 Hz, 1H) 6.97 (dd, J=8.1, 2.0 Hz, 1H) 7.01 (d, J=7.7 Hz, 1H) 7.12 (d, J=2.0 Hz, 1H) 7.22 (d, J=10.0 Hz, 1H) 7.35 (d, J=8.4 Hz, 1H) 8.02 (d, J=7.9 Hz, 1H) 8.37 (d, J=2.4 Hz, 1H) 11.97 (s, 1H)
LC/MS (method LC-A): R$_t$ 1.15 min, MH$^+$ 531
[α]$_D^{20}$: +166.6° (c 0.5, DMF)
Chiral SFC (method SFC-E): R$_t$ 3.78 min, MH$^+$ 531, chiral purity 100%,
or a pharmaceutically acceptable salt thereof.

17. The pharmaceutical composition of claim 1, wherein said compound is Enantiomer 8A
wherein $^1$H NMR (400 MHZ, DMSO-d$_6$) δ ppm 3.09 (s, 3H) 3.73 (s, 3H) 3.99 (s, 3H) 6.29 (d, J=7.6 Hz, 1H) 6.60 (br s, 2H) 6.92 (s, 1H) 6.98 (dd, J=8.3, 1.8 Hz, 1H) 7.07 (d, J=8.1 Hz, 1H) 7.13 (d, J=1.5 Hz, 1H) 7.36 (d, J=8.1 Hz, 1H) 7.54 (d, J=8.1 Hz, 1H) 7.69 (d, J=8.6 Hz, 1H) 8.49 (s, 1H) 8.60 (s, 1H) 12.41 (br s, 1H)
LC/MS (method LC-C): R$_t$ 3.25 min, MH$^+$567
[α]$_D^{20}$: −119.2° (c 0.2727, DMF)
Chiral SFC (method SFC-F): R$_t$ 2.64 min, MH$^+$ 567, chiral purity 100%,
or a pharmaceutically acceptable salt thereof.

18. The pharmaceutical composition of claim 1, wherein said compound is Enantiomer 8B
wherein 1H NMR (400 MHZ, DMSO-d$_6$) δ ppm 3.09 (s, 3H) 3.73 (s, 3H) 3.99 (s, 3H) 6.29 (d, J=8.1 Hz, 1H) 6.60 (s, 2H) 6.92 (s, 1H) 6.98 (dd, J=8.6, 2.0 Hz, 1H) 7.07 (d, J=8.1 Hz, 1H) 7.13 (d, J=2.0 Hz, 1H) 7.36 (d, J=8.6 Hz, 1H) 7.54 (dd, J=8.6, 1.5 Hz, 1H) 7.69 (d, J=8.6 Hz, 1H) 8.49 (s, 1H) 8.60 (s, 1H) 12.40 (br s, 1H)
LC/MS (method LC-C): R$_t$ 3.25 min, MH$^+$ 567
[α]$_D^{20}$: +125.1° (c 0.2455, DMF)
Chiral SFC (method SFC-F): R$_t$ 3.44 min, MH$^+$ 567, chiral purity 100%,
or a pharmaceutically acceptable salt thereof.

19. The pharmaceutical composition of claim 9, wherein said compound is Enantiomer 10A
wherein $^1$H NMR (360 MHz, DMSO-d$_6$) δ ppm 3.09 (s, 3H) 3.72 (s, 3H) 3.87 (s, 3H) 3.99 (s, 3H) 6.22 (d, J=7.7 Hz, 1H) 6.55-6.59 (m, 2H) 6.88-6.91 (m, 1H) 6.98 (dd, J=8.1, 1.8 Hz, 1H) 7.08 (d, J=7.7 Hz, 1H) 7.13 (d, J=2.2 Hz, 1H) 7.21 (s, 1H) 7.34 (d, J=8.1 Hz, 1H) 8.02 (d, J=1.5 Hz, 1H) 8.41 (s, 1H) 12.05 (br s, 1H)
LC/MS (method LC-A): R$_t$ 1.20 min, MH$^+$ 613
[α]$_D^{20}$: +81.4° (c 0.29, DMF)
Chiral SFC (method SFC-E): R$_t$ 3.34 min, MH$^+$ 613, chiral purity 100%,
or a pharmaceutically acceptable salt thereof.

20. The pharmaceutical composition of claim 1, wherein said compound is Enantiomer 10B
wherein $^1$H NMR (360 MHz, DMSO-d$_6$) δ ppm 3.09 (s, 3H) 3.72 (s, 3H) 3.87 (s, 3H) 3.99 (s, 3H) 6.22 (d, J=7.7 Hz, 1H) 6.55-6.60 (m, 2H) 6.90 (t, J=1.6 Hz, 1H) 6.98 (dd, J=8.2, 2.0 Hz, 1H) 7.08 (d, J=7.8 Hz, 1H) 7.13 (d, J=2.2 Hz, 1H) 7.21 (s, 1H) 7.34 (d, J=8.4 Hz, 1H) 8.01 (d, J=1.1 Hz, 1H) 8.41 (s, 1H) 12.08 (br s, 1H)
LC/MS (method LC-A): R$_t$ 1.20 min, MH$^+$ 613
[α]$_D^{20}$: −99.6° (c 0.261, DMF)
Chiral SFC (method SFC-E): R$_t$ 3.69 min, MH$^+$ 613, chiral purity 100%,
or a pharmaceutically acceptable salt thereof.

21. The pharmaceutical composition of claim 1, wherein said compound is Enantiomer 11A
wherein $^1$H NMR (600 MHZ, DMSO-d$_6$) δ ppm 2.50 (s, 3H) 3.09 (s, 3H) 3.72 (s, 3H) 4.00 (s, 3H) 6.28 (d, J=7.8 Hz, 1H) 6.56-6.63 (m, 2H) 6.92 (br s, 1H) 6.97 (dd, J=8.4, 1.9 Hz, 1H) 7.05 (br s, 1H) 7.07 (d, J=7.9 Hz, 1H) 7.13 (d, J=1.9 Hz, 1H) 7.35 (d, J=8.4 Hz, 1H) 7.90 (br s, 1H) 8.53 (s, 1H) 12.41 (br s, 1H)
LC/MS (method LC-A): R$_t$ 1.26 min, MH$^+$ 597
[α]$_D^{20}$: +81.3° (c 0.3455, DMF)

Chiral SFC (method SFC-E): $R_t$ 2.96 min, MH$^+$ 597, chiral purity 100%, or a pharmaceutically acceptable salt thereof.

22. The pharmaceutical composition of claim 1, wherein said compound is Enantiomer 11B wherein $^1$H NMR (600 MHZ, DMSO-d$_6$) δ ppm 2.51 (s, 3H) 3.09 (s, 3H) 3.72 (s, 3H) 4.00 (s, 3H) 6.28 (d, J=7.9 Hz, 1H) 6.58-6.60 (m, 2H) 6.92 (t, J=1.8 Hz, 1H) 6.97 (dd, J=8.4, 1.9 Hz, 1H) 7.05 (br s, 1H) 7.06 (d, J=7.9 Hz, 1H) 7.13 (d, J=2.1 Hz, 1H) 7.35 (d, J=8.2 Hz, 1H) 7.89 (br s, 1H) 8.53 (s, 1H) 12.37 (br s, 1H)

LC/MS (method LC-A): $R_t$ 1.26 min, MH$^+$ 597

$[\alpha]_D^{20}$: −87.4° (c 0.342, DMF)

Chiral SFC (method SFC-E): $R_t$ 3.44 min, MH$^+$ 597, chiral purity 100%, or a pharmaceutically acceptable salt thereof.

23. A pharmaceutical composition, comprising compound:

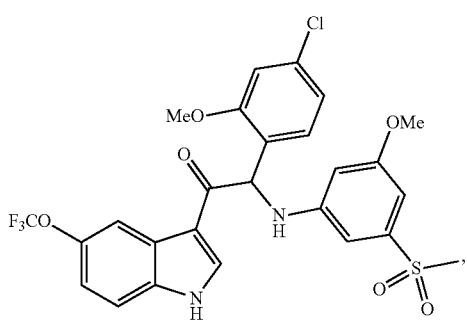

(9)

or an enantiomer thereof, and one or more pharmaceutically acceptable excipients, diluents, or carriers.

24. The pharmaceutical composition of claim 23, wherein said compound is

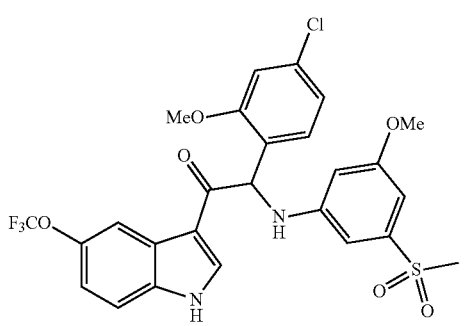

(9)

wherein $^1$H NMR (400 MHZ, DMSO-d$_6$) δ ppm 3.09 (s, 3H) 3.73 (s, 3H) 3.99 (s, 3H) 6.26 (d, J=7.9 Hz, 1H) 6.57-6.62 (m, 2H) 6.91 (t, J=1.9 Hz, 1H) 6.98 (dd, J=8.4, 2.0 Hz, 1H) 7.07 (d, J=7.9 Hz, 1H) 7.13 (d, J=2.0 Hz, 1H) 7.22 (dd, J=8.6, 2.2 Hz, 1H) 7.36 (d, J=8.4 Hz, 1H) 7.59 (d, J=8.8 Hz, 1H) 8.06 (d, J=0.9 Hz, 1H) 8.55 (s, 1H) 12.28 (br s, 1H)

LC/MS (method LC-A): $R_t$ 1.31 min, MH$^+$ 583, and one or more pharmaceutically acceptable excipients, diluents, or carriers.

25. The pharmaceutical composition of claim 23, wherein said enantiomer of said compound is Enantiomer 9A wherein $^1$H NMR (400 MHZ, DMSO-d$_6$) δ ppm 3.09 (s, 3H) 3.73 (s, 3H) 3.99 (s, 3H) 6.26 (d, J=7.9 Hz, 1H) 6.55-6.62 (m, 2H) 6.91 (t, J=1.5 Hz, 1H) 6.98 (dd, J=8.4, 2.0 Hz, 1H) 7.07 (d, J=7.9 Hz, 1H) 7.13 (d, J=2.0 Hz, 1H) 7.21 (dd, J=8.8, 1.8 Hz, 1H) 7.36 (d, J=8.4 Hz, 1H) 7.59 (d, J=8.8 Hz, 1H) 8.07 (d, J=0.9 Hz, 1H) 8.55 (s, 1H) 12.29 (br s, 1H)

LC/MS (method LC-A): $R_t$ 1.20 min, MH$^+$ 583

$[\alpha]_D^{20}$: +130.3° (c 0.555, DMF)

Chiral SFC (method SFC-E): $R_t$ 3.10 min, MH$^+$ 583, chiral purity 100%, and one or more pharmaceutically acceptable excipients, diluents, or carriers.

26. The pharmaceutical composition of claim 23, wherein said enantiomer of said compound is Enantiomer 9B wherein $^1$H NMR (400 MHZ, DMSO-d$_6$) δ ppm 3.09 (s, 3H) 3.73 (s, 3H) 3.99 (s, 3H) 6.26 (d, J=7.9 Hz, 1H) 6.56-6.62 (m, 2H) 6.92 (t, J=2.0 Hz, 1H) 6.98 (dd, J=8.1, 2.0 Hz, 1H) 7.07 (d, J=7.9 Hz, 1H) 7.13 (d, J=2.0 Hz, 1H) 7.22 (dd, J=8.8, 1.8 Hz, 1H) 7.36 (d, J=8.4 Hz, 1H) 7.59 (d, J=8.8 Hz, 1H) 8.07 (d, J=0.9 Hz, 1H) 8.55 (s, 1H) 12.30 (br s, 1H)

LC/MS (method LC-A): $R_t$ 1.20 min, MH$^+$ 583

$[\alpha]_D^{20}$: −133.2° (c 0.5, DMF)

Chiral SFC (method SFC-E): $R_t$ 3.50 min, MH$^+$ 583, chiral purity 100%, and one or more pharmaceutically acceptable excipients, diluents, or carriers.

27. The pharmaceutical composition of claim 9, wherein the compound is in the form of a pharmaceutically acceptable salt.

\* \* \* \* \*

```
                          SEQUENCE LISTING

Sequence total quantity: 14
SEQ ID NO: 1             moltype = DNA  length = 20
FEATURE                  Location/Qualifiers
misc_feature             1..20
                         note = source = /organism="Dengue virus"
                          /mol_type="unassigned DNA"
source                   1..20
                         mol_type = unassigned DNA
                         organism = Dengue virus
SEQUENCE: 1
tcggagccgg agtttacaaa                                                 20

SEQ ID NO: 2             moltype = DNA  length = 20
FEATURE                  Location/Qualifiers
misc_feature             1..20
                         note = source = /organism="Dengue virus"
                          /mol_type="unassigned DNA"
source                   1..20
                         mol_type = unassigned DNA
                         organism = Dengue virus
SEQUENCE: 2
tcttaacgtc cgcccatgat                                                 20

SEQ ID NO: 3             moltype = DNA  length = 19
FEATURE                  Location/Qualifiers
misc_feature             1..19
                         note = source = /organism="Dengue virus"
                          /mol_type="unassigned DNA"
source                   1..19
                         mol_type = unassigned DNA
                         organism = Dengue virus
SEQUENCE: 3
attccacaca atgtggcat                                                  19

SEQ ID NO: 4             moltype = DNA  length = 23
FEATURE                  Location/Qualifiers
misc_feature             1..23
                         note = source = /organism="Dengue virus"
                          /mol_type="unassigned DNA"
source                   1..23
                         mol_type = unassigned DNA
                         organism = Dengue virus
SEQUENCE: 4
ggatagacca gagatcctgc tgt                                             23

SEQ ID NO: 5             moltype = DNA  length = 20
FEATURE                  Location/Qualifiers
misc_feature             1..20
                         note = source = /organism="Dengue virus"
                          /mol_type="unassigned DNA"
source                   1..20
                         mol_type = unassigned DNA
```

```
                                organism = Dengue virus
SEQUENCE: 5
cattccattt tctggcgttc                                                    20

SEQ ID NO: 6               moltype = DNA  length = 20
FEATURE                    Location/Qualifiers
misc_feature               1..20
                           note = source = /organism="Dengue virus"
                           /mol_type="unassigned DNA"
source                     1..20
                           mol_type = unassigned DNA
                           organism = Dengue virus
SEQUENCE: 6
caatccatct tgcggcgctc                                                    20

SEQ ID NO: 7               moltype = DNA  length = 20
FEATURE                    Location/Qualifiers
misc_feature               1..20
                           note = source = /organism="Dengue virus"
                           /mol_type="unassigned DNA"
source                     1..20
                           mol_type = unassigned DNA
                           organism = Dengue virus
SEQUENCE: 7
cagcatcatt ccaggcacag                                                    20

SEQ ID NO: 8               moltype = DNA  length = 20
FEATURE                    Location/Qualifiers
misc_feature               1..20
                           note = source = /organism="Dengue virus"
                           /mol_type="unassigned DNA"
source                     1..20
                           mol_type = unassigned DNA
                           organism = Dengue virus
SEQUENCE: 8
caacatcaat ccaggcacag                                                    20

SEQ ID NO: 9               moltype = DNA  length = 19
FEATURE                    Location/Qualifiers
misc_feature               1..19
                           note = source = /organism="Dengue virus"
                           /mol_type="unassigned DNA"
source                     1..19
                           mol_type = unassigned DNA
                           organism = Dengue virus
SEQUENCE: 9
cggttagagg agacccctc                                                     19

SEQ ID NO: 10              moltype = DNA  length = 21
FEATURE                    Location/Qualifiers
misc_feature               1..21
                           note = source = /organism="Dengue virus"
                           /mol_type="unassigned DNA"
source                     1..21
                           mol_type = unassigned DNA
                           organism = Dengue virus
SEQUENCE: 10
gagacagcag gatctctggt c                                                  21

SEQ ID NO: 11              moltype = DNA  length = 28
FEATURE                    Location/Qualifiers
misc_feature               1..28
                           note = source = /organism="Dengue virus"
                           /mol_type="unassigned DNA"
source                     1..28
                           mol_type = unassigned DNA
                           organism = Dengue virus
SEQUENCE: 11
aaggactaga ggttagagga gacccccc                                           28

SEQ ID NO: 12              moltype = DNA  length = 18
FEATURE                    Location/Qualifiers
misc_feature               1..18
                           note = source = /organism="Dengue virus"
                           /mol_type="unassigned DNA"
source                     1..18
                           mol_type = unassigned DNA
                           organism = Dengue virus
SEQUENCE: 12
```

```
ggccaggtca tcaccatt                                              18

SEQ ID NO: 13          moltype = DNA  length = 21
FEATURE                Location/Qualifiers
misc_feature           1..21
                       note = source = /organism="Dengue virus"
                       /mol_type="unassigned DNA"
source                 1..21
                       mol_type = unassigned DNA
                       organism = Dengue virus
SEQUENCE: 13
atgtccacgt cacacttcat g                                          21

SEQ ID NO: 14          moltype = DNA  length = 21
FEATURE                Location/Qualifiers
misc_feature           1..21
                       note = source = /organism="Dengue virus"
                       /mol_type="unassigned DNA"
source                 1..21
                       mol_type = unassigned DNA
                       organism = Dengue virus
SEQUENCE: 14
ttccgctgcc ctgaggctct c                                          21
```